US010519119B2

United States Patent
Yong et al.

(10) Patent No.: US 10,519,119 B2
(45) Date of Patent: Dec. 31, 2019

(54) NICOTINIC ACID DERIVATIVES, THEIR PREPARATION AND THE USE THEREOF

(71) Applicant: XIAMEN INSTITUTE OF RARE EARTH MATERIALS, Xiamen, Fujian (CN)

(72) Inventors: Jianping Yong, Fujian (CN); Canzhong Lu, Fujian (CN)

(73) Assignee: XIAMEN INSTITUTE OF RARE EARTH MATERIALS, Xiamen, Fujian (CN)

( * ) Notice: Subject to any disclaimer, the term of this patent is extended or adjusted under 35 U.S.C. 154(b) by 0 days.

(21) Appl. No.: 15/816,723

(22) Filed: Nov. 17, 2017

(65) Prior Publication Data

US 2019/0077777 A1   Mar. 14, 2019

(30) Foreign Application Priority Data

Sep. 13, 2017  (CN) .......................... 2017 1 0823604

(51) Int. Cl.
| | |
|---|---|
| *A61P 35/00* | (2006.01) |
| *C07D 413/12* | (2006.01) |
| *A61P 35/04* | (2006.01) |
| *C07D 261/08* | (2006.01) |

(52) U.S. Cl.
CPC ............ *C07D 261/08* (2013.01); *A61P 35/00* (2018.01); *A61P 35/04* (2018.01); *C07D 413/12* (2013.01)

(58) Field of Classification Search
CPC .................................................. C07D 413/12
See application file for complete search history.

(56) References Cited

U.S. PATENT DOCUMENTS

2005/0171358 A1* 8/2005 Shimozono ............ A01N 43/80
548/247

FOREIGN PATENT DOCUMENTS

| CN | 103360382 A | 10/2013 |
|---|---|---|
| CN | 103601762 A | 2/2014 |
| CN | 103664991 A | 3/2014 |

OTHER PUBLICATIONS

Yinxing Sun et al., "Synthesis and biological evaluation of novel hydrogen sulfide releasing nicotinic acid derivatives", Bioorganic & Medicinal Chemistry, vol. 24, 2016, pp. 5368-5373.
Yu Qu et al., "Permeability of novel 4'-N-substituted (aminomethyl) benzoate-7-substituted nicotinic acid ester derivatives of scutellarein in Caco-2 cells and in an in vitro model of the blood-brain barrier", Med Chem Res, 2016, vol. 25, pp. 2205-2213.
Rana Abu Farha et al., "Lipid lowering activity of novel N-(benzoylphenyl)pyridine-3-carboxamide derivatives in Triton WR-1339-induced hyperlipidemic rats", Journal of Enzyme Inhibition and Medicinal Chemistry, ISSN: 1475-6366, 2016, vol. 31(S4), pp. 138-144.
Wagdy M. Eldehna et al., "Design, Synthesis and Antitubercular Activity of Certain Nicotinic Acid Hydrazides", Molecules, ISSN 1420-3049, 2015, vol. 20, pp. 8800-8815.

* cited by examiner

*Primary Examiner* — Susanna Moore
(74) *Attorney, Agent, or Firm* — Novick, Kim & Lee, PLLC; Allen Xue

(57) ABSTRACT

A nicotinic acid derivative is represented by formula (I), and a pharmaceutically acceptable salt or solvate thereof.

(I)

In formula (I), Z is selected from O, S, $NR_3$, wherein $R_3$ is hydrogen or $C_{1-6}$ alkyl. $R_1$ or $R_2$ is independently selected from the group consisting of hydrogen, $C_{1-6}$ alkyl, $C_{1-6}$ alkoxy, halo $C_{1-6}$ alkyl, halogen, cyano, nitro, aryl, aryloxy, heteroaryl, heteroaryloxy, heterocyclyl, and heterocycyloxy. Such $C_{1-6}$ alkyl, $C_{1-6}$ alkoxy, halo $C_{1-6}$ alkyl, aryl, heteroaryl, and heterocyclyl may be optionally substituted with a substituent selected from the group consisting of $C_{1-6}$ alkyl, $C_{1-6}$ alkoxy, halo $C_{1-6}$ alkyl, halogen, cyano, nitro, and aryl. These compounds or salts thereof have a strong inhibitory activity on colorectal cancer cell line HCT-116, human lung cancer cell line A549, and breast cancer cell line MCF-7.

6 Claims, No Drawings

NICOTINIC ACID DERIVATIVES, THEIR PREPARATION AND THE USE THEREOF

TECHNICAL FIELD

The present invention belongs to the field of pharmaceutical chemistry, relates to a type of nicotinic acid derivatives, more specifically to nicotinic acid derivatives containing isoxazole heterocycles, their preparation processes and uses.

BACKGROUND TECHNOLOGY

Cancer is a kind of diseases with abnormal proliferation and metastasis of cells, and is the second most common cause of death for human, only after cardiovascular and cerebrovascular diseases. Cancer can occur at all ages in various organs and tissues. The types of cancers leading to death are mainly: lung cancer, stomach cancer, liver cancer, colon cancer, breast cancer, etc. Especially in recent years, lung cancer has become the tumor of the highest incidence. According to the statistics reported by World Health Organization, in year 2017, up to now, 1,688,780 new cancer patients have been diagnosed globally, and 600,920 cancer patients will die in the United States. Cancer facts and figure 2017: (https://www.cancer.org/research/cancer-facts-statistics/allcancer-facts-figures/cancer-facts-figures-2017.html). However, most of the cancers are found to be in middle stage or advanced stage while treatment in clinical and the overall therapeutic effect is poor. Cancer has caused a great threat to human survival.

Methods for cancer treatment include: surgery, radiation treatment, chemical treatment, etc. Sometimes, surgical treatment cannot eradicate cancer cells, and cancer may recur. Additionally, surgical treatment may also lead to bad results, for example, surgery for cervical cancer and bladder cancer may lead to infertility, sexual dysfunction, etc. Radiation treatment will injure normal cells. Hence, drug treatment is a better choice. However, the treatment of cancer becomes rather difficult due to the continuous emergence of multidrug resistance. In addition, the anti-cancer drugs currently applied in clinical still cannot achieve a satisfactory specificity. When patients receive chemotherapy, the body's normal cells are often killed together, thus chemotherapy seriously affects the normal physiological function together with many side effects. Therefore, the development of specific anti-cancer drugs with high activity and less side effects is an urgent demand in the field of cancer treatment.

Nicotinic acid derivatives have broad-spectrum biological activity [(1) Bioorg. Med. Chem., 2016, 24:5368-5373; (2) Med. Chem. Res., 2016, 25: 2205-2213; (3) J. Enzyme Inhib. Med. Chem., 2016, 31(S4): 138-144; (4) Molecules, 2015, 20, 8800-8815]. Isoxazole heterocycles are commonly introduced into drug molecules as pharmacophore to enhance pharmacological activity. Patent application with publication No. CN103360382A discloses that quinazoline derivatives containing an isoxazole heterocycle substituent have a significant inhibitory activity on lung cancer cell A549, colorectal cancer cell HCT-116 and breast cancer cell MCF-7. Patent application with publication No. CN103664991A discloses that thiophene [2,3-d] pyrimidine derivatives containing an isoxazole heterocycle substituent have a significant inhibitory activity on lung cancer cell A549, colorectal cancer cell HCT-116 and breast cancer cell MCF-7. Patent application with publication No. CN103601762A discloses that ferrocene derivatives containing an isoxazole heterocycle have a significant inhibitory activity on lung cancer cell A549, colorectal cancer cell HCT-116 and breast cancer cell MCF-7.

Contents of the Invention

In order to solve the above problems, the present invention provides isoxazole heterocycle-containing nicotinic acid derivatives represented by the following formula (I). The biological results indicate that these compounds exhibited a strong inhibitory activity toward human lung cancer cell line A549, colorectal cancer cell line HCT-116 and breast cancer cell line MCF-7, and which can be used as candidate compounds or leading compounds for development of the anti-cancer drugs.

The invention is achieved by the following technical solution:

a nicotinic acid derivative represented by formula (I), or pharmaceutically acceptable salt or solvate thereof,

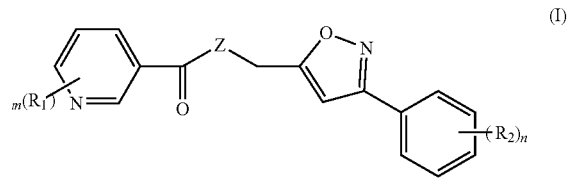

(I)

wherein Z is selected from O, S, $NR_3$, wherein $R_3$ is hydrogen or $C_{1-6}$ alkyl;

$R_1$ or $R_2$ is independently selected from the group consisting of hydrogen, $C_{1-6}$ alkyl, $C_{1-6}$ alkoxy, halo $C_{1-6}$ alkyl, halogen, cyano, nitro, aryl, aryloxy, heteroaryl, heteroaryloxy, heterocyclyl, and heterocyclyloxy; the $C_{1-6}$ alkyl, $C_{1-6}$ alkoxy, halo $C_{1-6}$ alkyl, aryl, heteroaryl, and heterocyclyl may be optionally substituted with a substituent selected from the group consisting of $C_{1-6}$ alkyl, $C_{1-6}$ alkoxy, halo $C_{1-6}$ alkyl, halogen, cyano, nitro, and aryl;

m is an integer ranging from 0 to 4; and n is an integer ranging from 0 to 5.

According to the present invention, the $C_{1-6}$ alkyl refers to a straight or branched chain alkyl group having 1 to 6 carbon atoms such as methyl, ethyl, propyl, isopropyl, butyl, isobutyl, tert-butyl, sec-butyl, pentyl, and neopentyl.

According to the present invention, the aryl refers to a monocyclic or polycyclic aromatic group having 6 to 20 (preferably 6 to 14) carbon atoms, and representative aryl groups include phenyl, naphthyl, anthryl, pyrenyl, etc.

According to the present invention, the heteroaryl refers to a monocyclic or polycyclic aromatic group having 1 to 20 carbon atoms and 1 to 4 heteroatoms selected from N, S and O, and representative heteroaryl groups include: thienyl, furyl, pyrrolyl, pyridyl, pyrimidyl, imidazolyl, thiazolyl, indolyl, azanaphthyl, azaanthryl, azapyrenyl and the like.

According to the present invention, the heterocyclyl refers to a monocyclic or polycyclic non-aromatic group having 1 to 20 carbon atoms and 1 to 4 heteroatoms selected from N, S and O. In particular, the heterocyclyl may include, but is not limited to, a 4-membered ring, such as azetidinyl, and oxetanyl; a 5-membered ring, such as tetrahydrofuranyl, dioxolyl, pyrrolidinyl, imidazolidinyl, pyrazolidinyl, and pyrrolidinyl; or a 6-membered ring, such as tetrahydropyranyl, piperidinyl, morpholinyl, dithianyl, thiomorpholinyl, piperazinyl or trithianyl; or a 7-membered ring, such as diazepanyl. Optionally, the heterocyclyl may be benzo-fused. The heterocyclyl may be bicyclic, for example, but not limited to, a 5,5 membered ring, such as a hexahydrocyclopenta [c] pyrrol-2 (1H)-yl ring, or a 5,6 membered bicyclic ring, such as hexahydropyrrolo[1,2-a] pyrazin-2 (1H)-yl ring.

According to the present invention, the halogen refers to F, Cl, Br and I.

In a preferred embodiment, in the compound of formula (I), $R_1$ is selected from $C_{1-6}$ alkyl, $C_{1-6}$ alkoxy, halo $C_{1-6}$ alkyl, phenyl, phenoxy, substituted phenyl, substituted phenoxy, heterocyclyl, and halogen.

In yet another preferred embodiment, in the compound of formula (I), $R_2$ is selected from hydrogen, halogen, cyano, nitro, $C_{1-6}$ alkyl, $C_{1-6}$ alkoxy or halo $C_{1-6}$ alkyl.

More preferably, in the compound of formula (I),

Z is selected from O and NH;

$R_1$ is independently selected from hydrogen, fluoro, chloro, bromo, methyl, methoxy, trifluoromethyl, phenyl, and phenoxy;

$R_2$ is independently selected from hydrogen, fluoro, chloro, bromo, methyl, ethyl, t-butyl, methoxy, nitro or trifluoromethyl;

m is an integer of 0, 1, 2, and when m is greater than 1, $R_1$ may be the same or different groups;

n is an integer of 0, 1, 2, and 3; and when n is greater than 1, $R_2$ may be the same or different groups;

As an example, the compound of formula (I) may be selected from the following exemplified compounds and pharmaceutically acceptable salts thereof:

YP-1

![YP-1 structure]

YP-2

![YP-2 structure]

YP-3

![YP-3 structure]

YP-4

![YP-4 structure]

-continued

YP-5

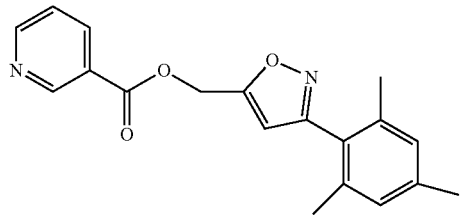

YP-6

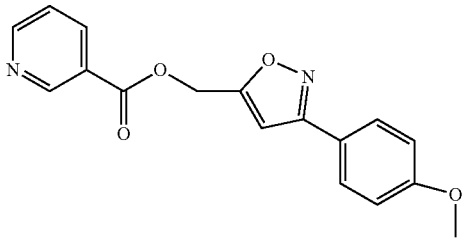

YP-7

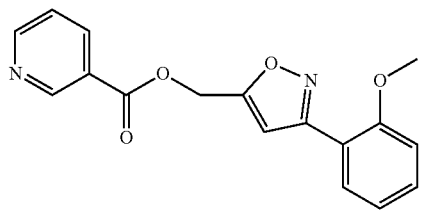

YP-8

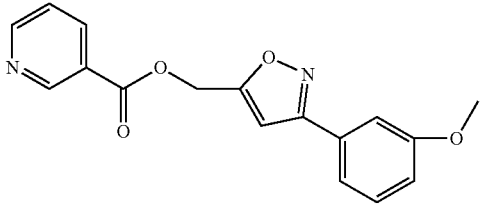

YP-9

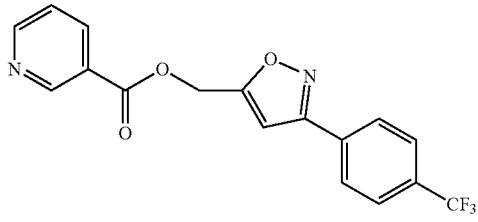

YP-10

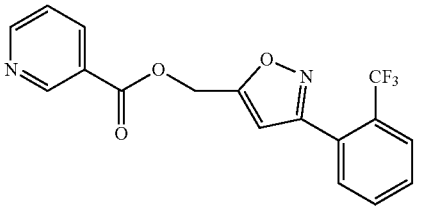

YP-11

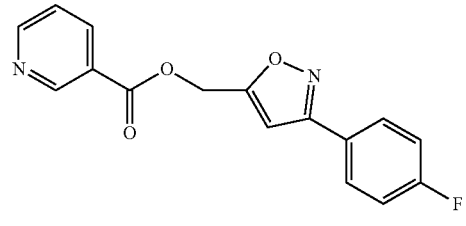

YP-12 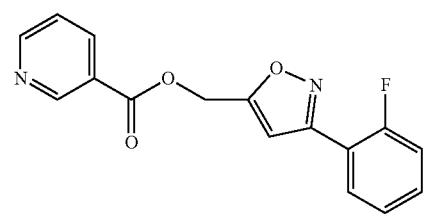
YP-13 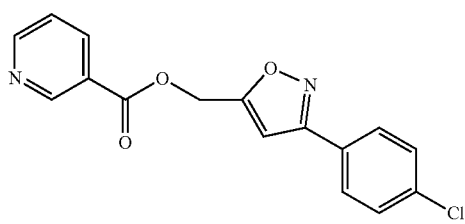
YP-14 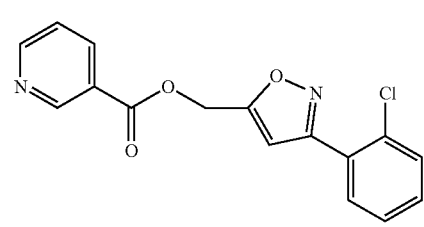
YP-15 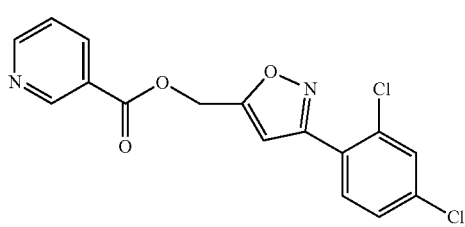
YP-16 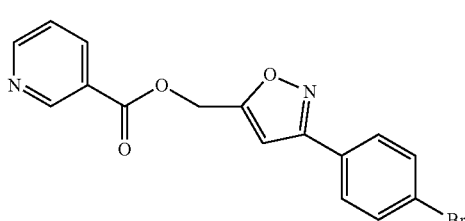
YP-17 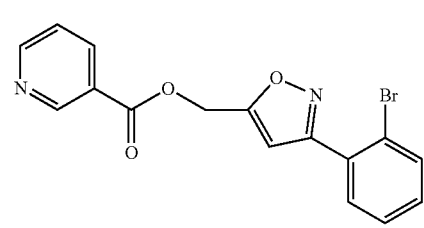
YP-18 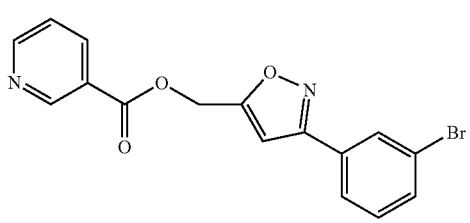
YP-19 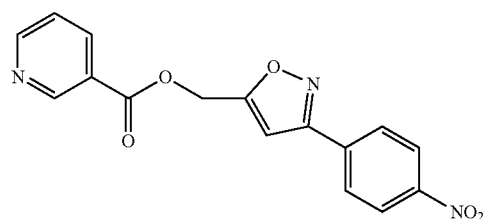
YP-20 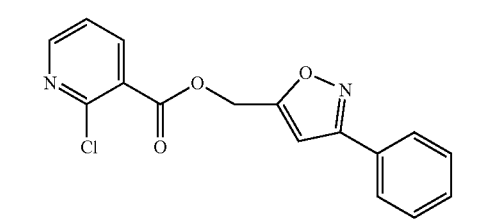
YP-21 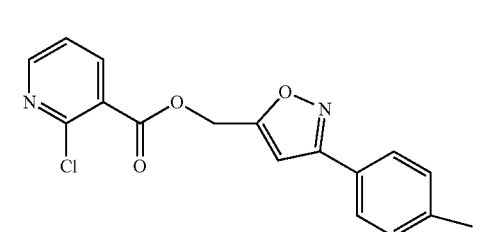
YP-22 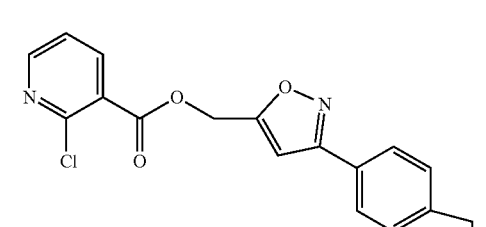
YP-23 
YP-24 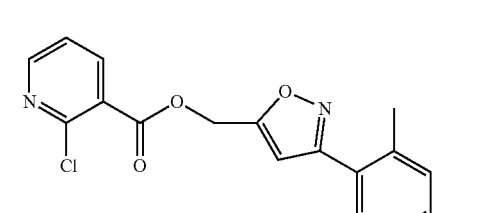

YP-25
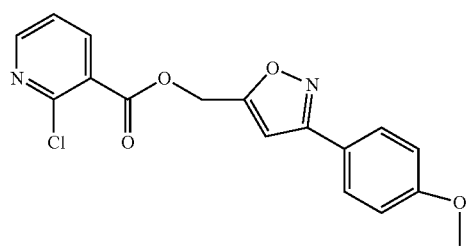
YP-26
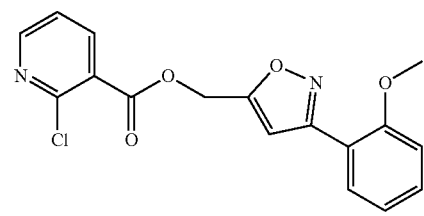
YP-27
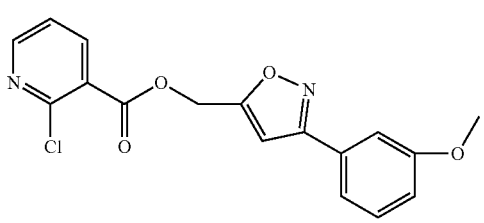
YP-28
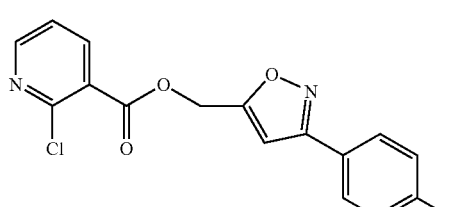
YP-29
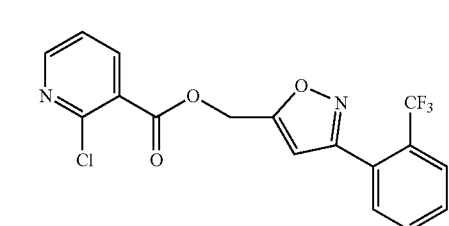
YP-30
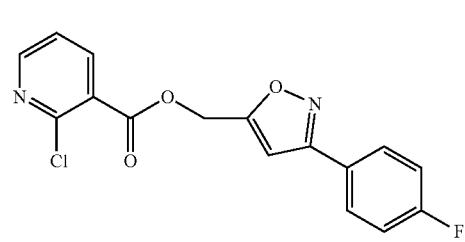
YP-31
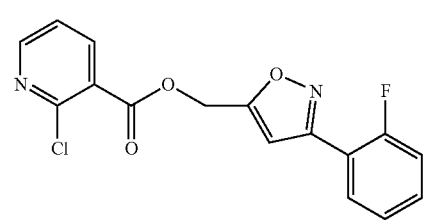
YP-32
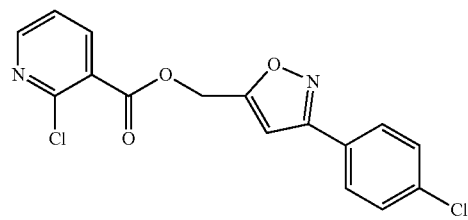
YP-33
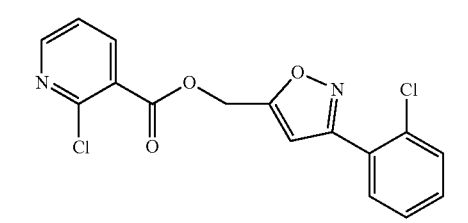
YP-34
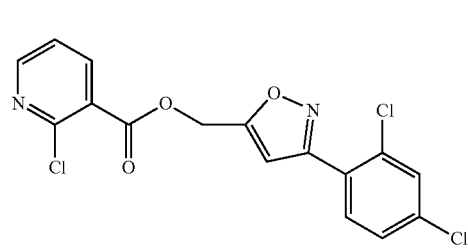
YP-35
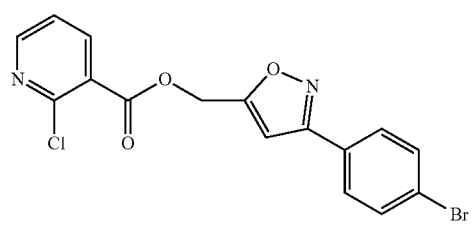
YP-36
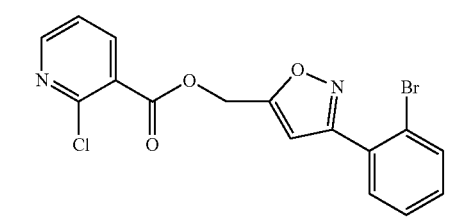
YP-37
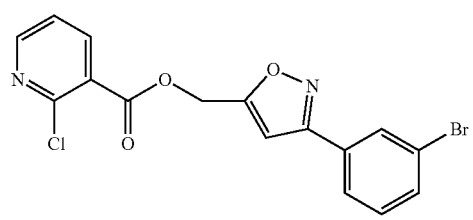
YP-38
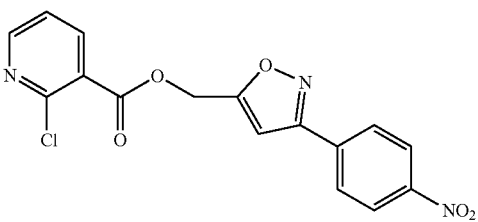

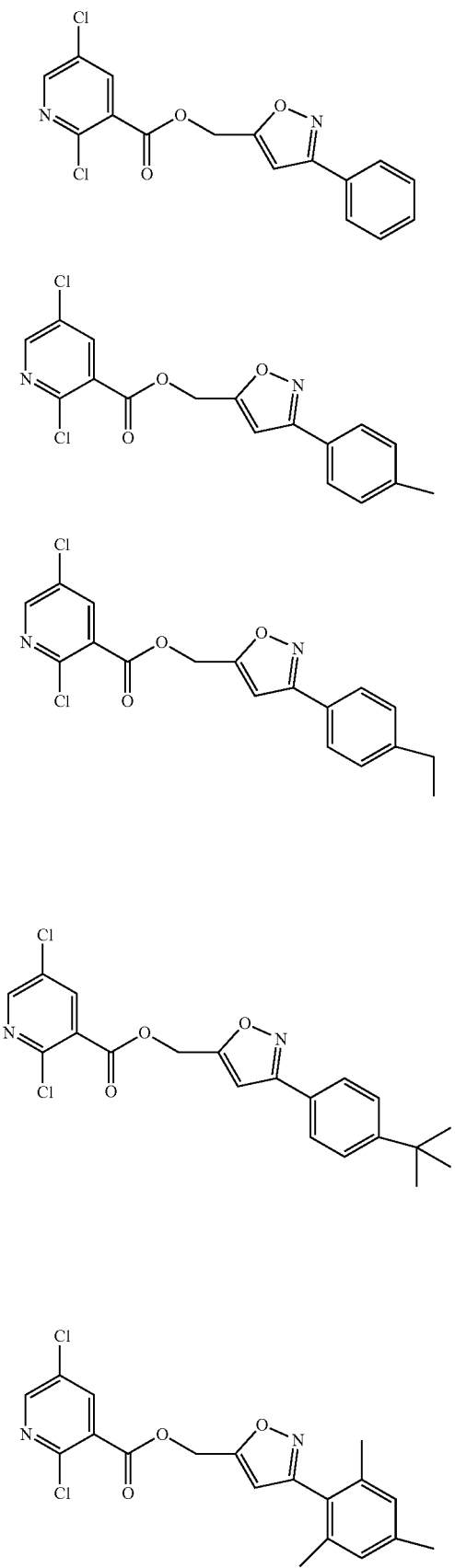

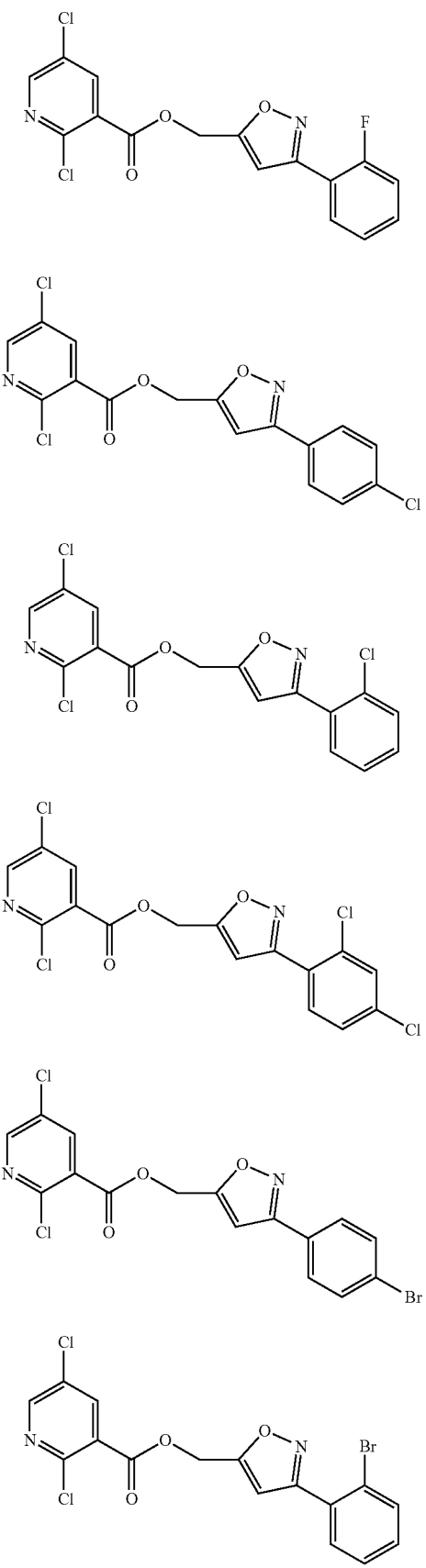
YP-50
YP-51
YP-52
YP-53
YP-54
YP-55
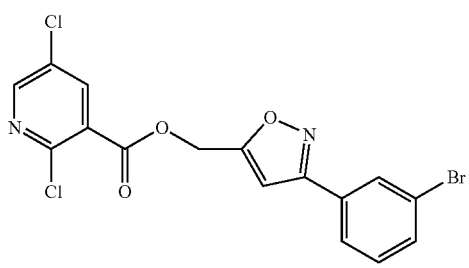
YP-56
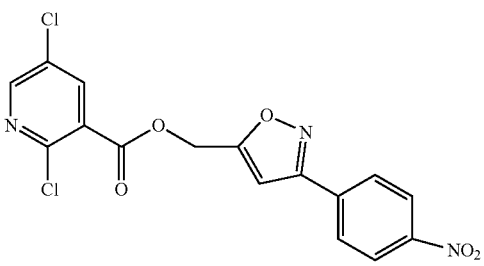
YP-57
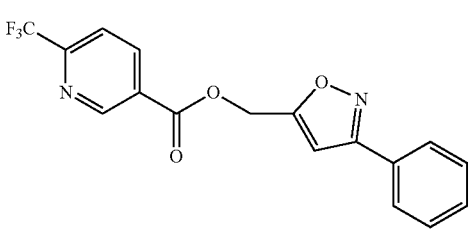
YP-58
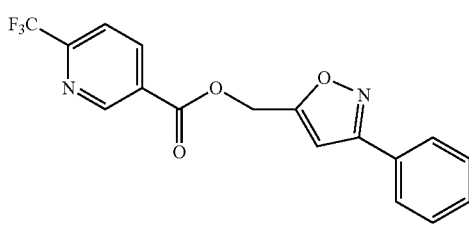
YP-59
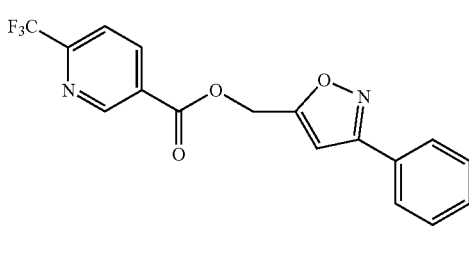
YP-60
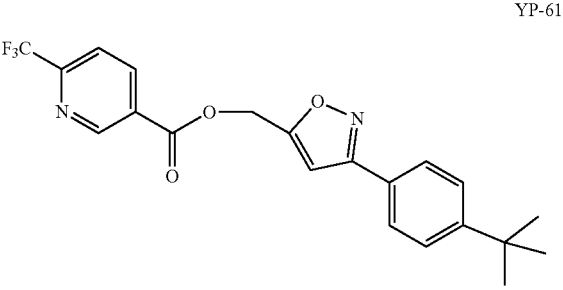
YP-61

-continued
YP-62
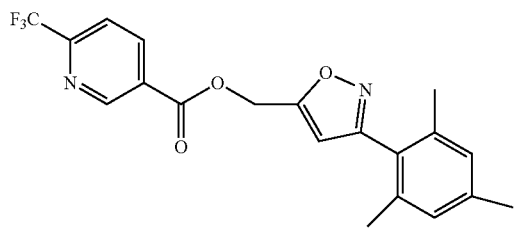
YP-68
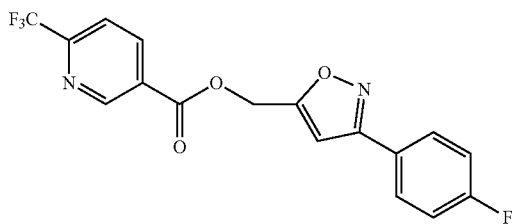
YP-63
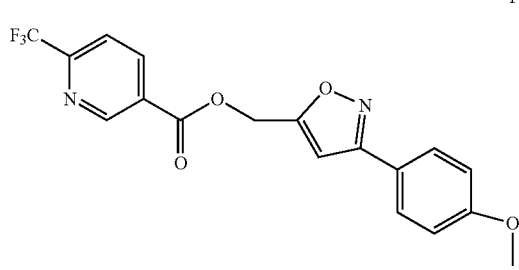
YP-69
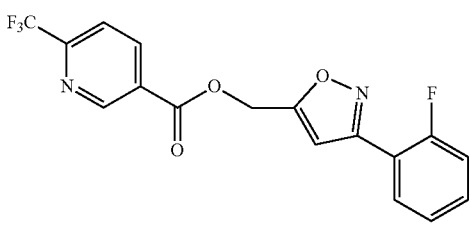
YP-64
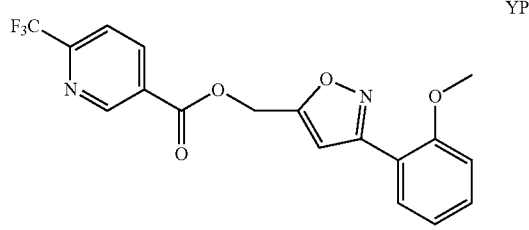
YP-70
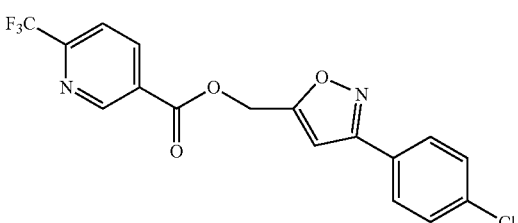
YP-65
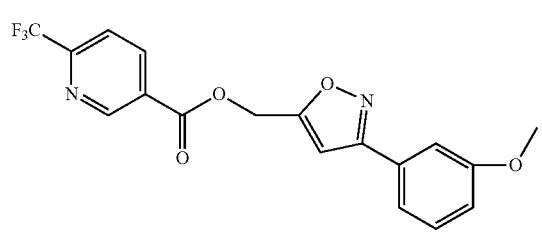
YP-71
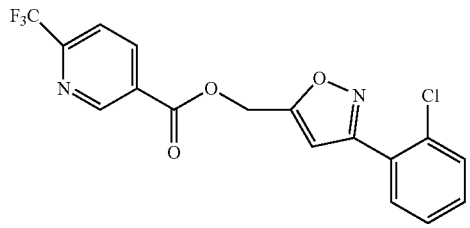
YP-66
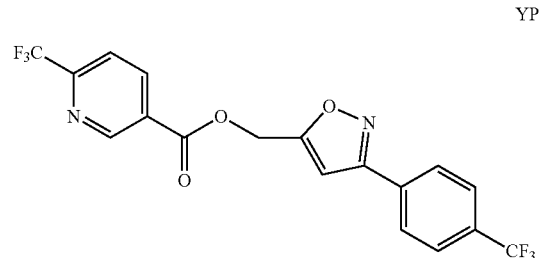
YP-72
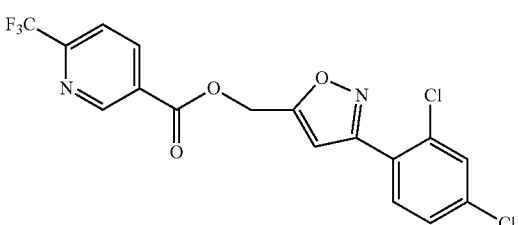
YP-67
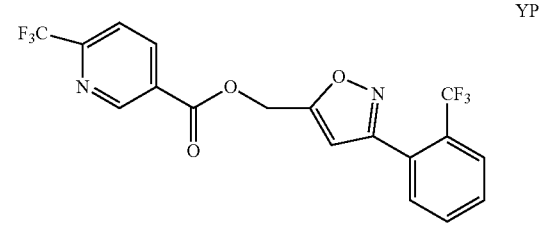
YP-73
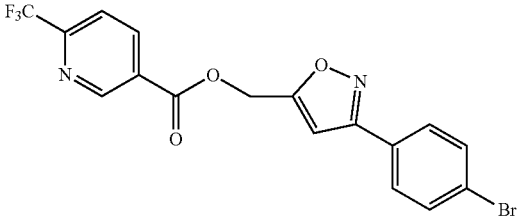

YP-74
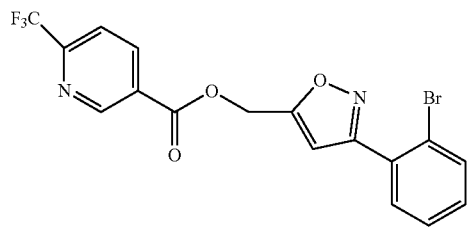
YP-80
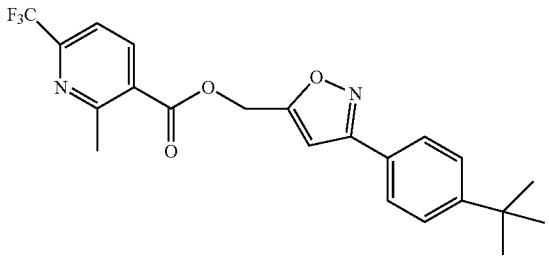
YP-75
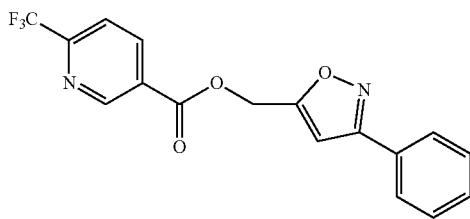
YP-81
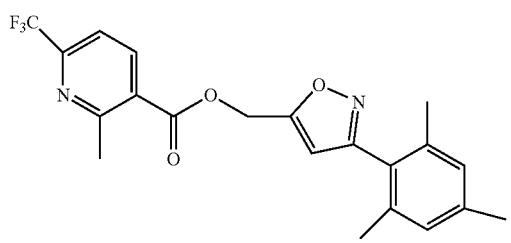
YP-76
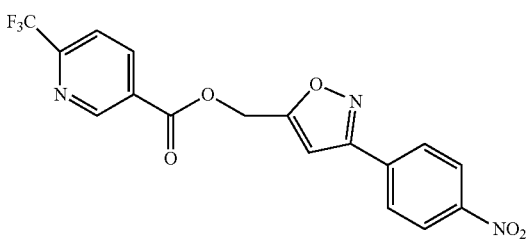
YP-82
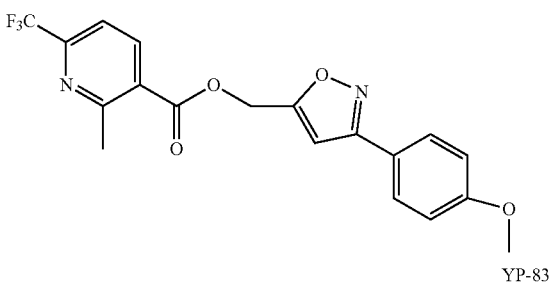
YP-77
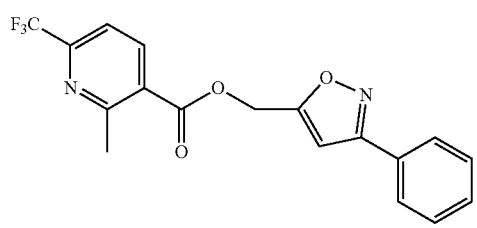
YP-83
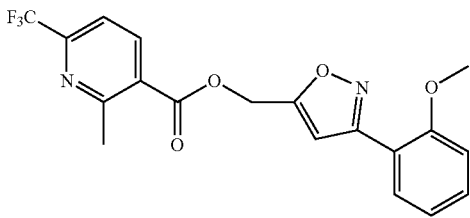
YP-78
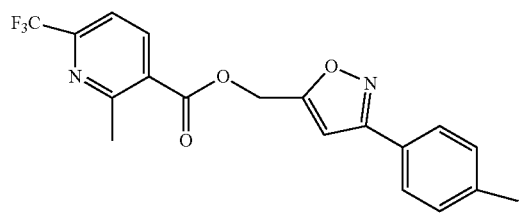
YP-84
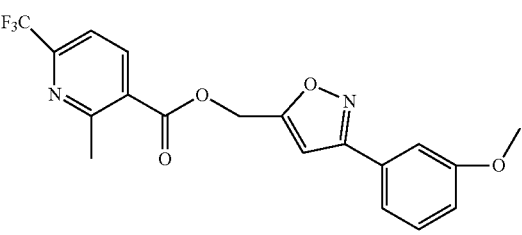
YP-79
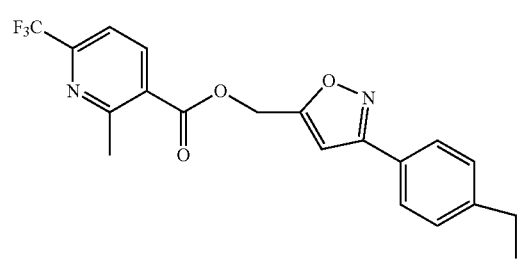
YP-85
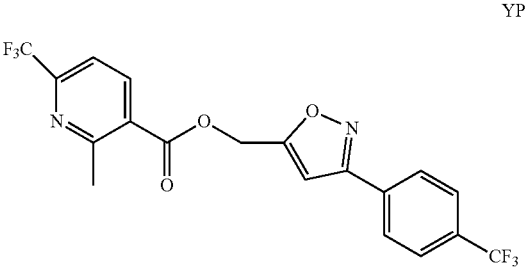

YP-86
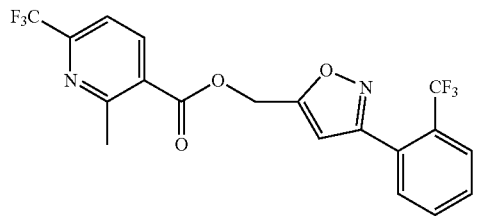
YP-87
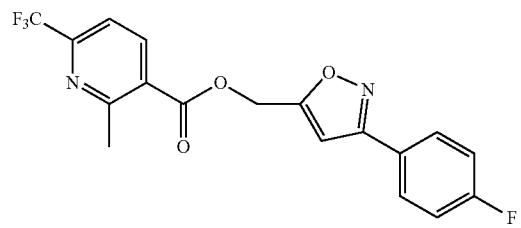
YP-88
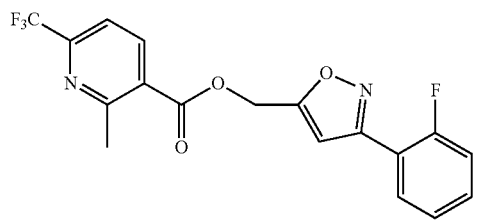
YP-89
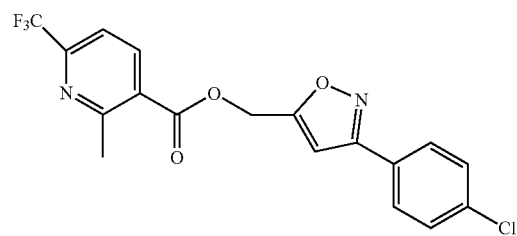
YP-90
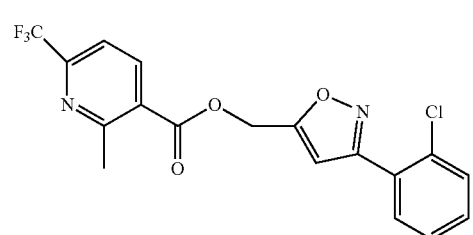
YP-91
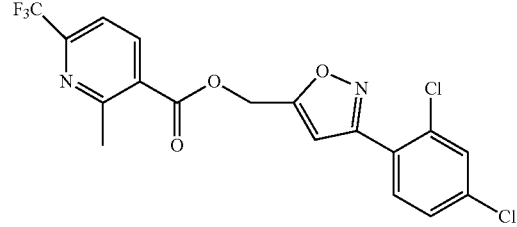
YP-92
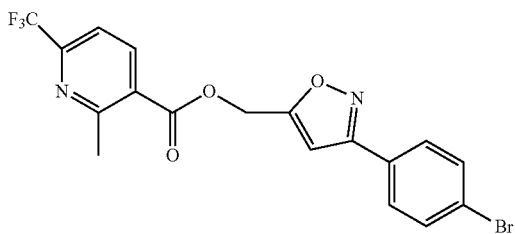
YP-93
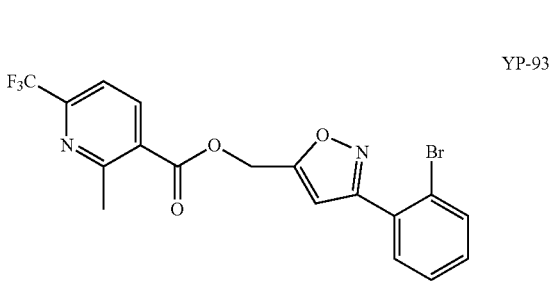
YP-94
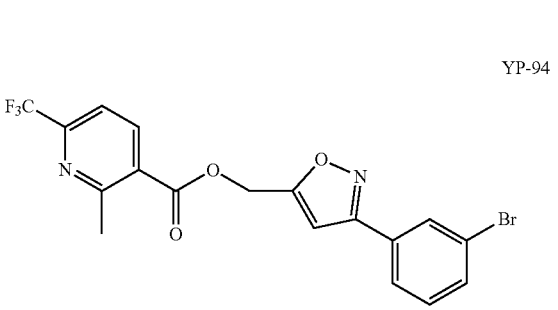
YP-95
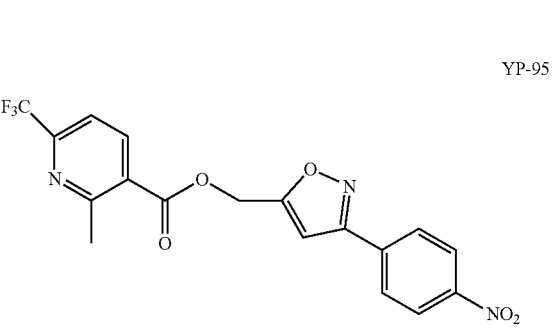
YP-96
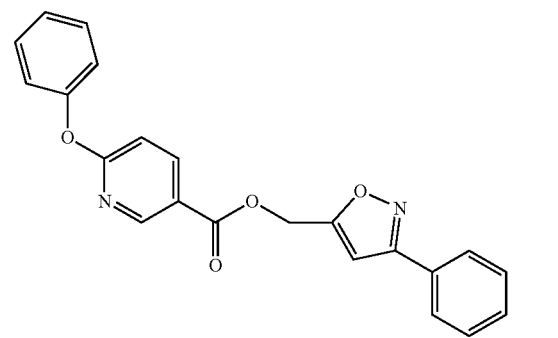

-continued
YP-97
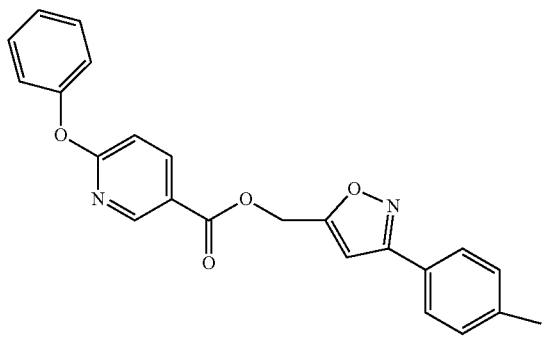
YP-98
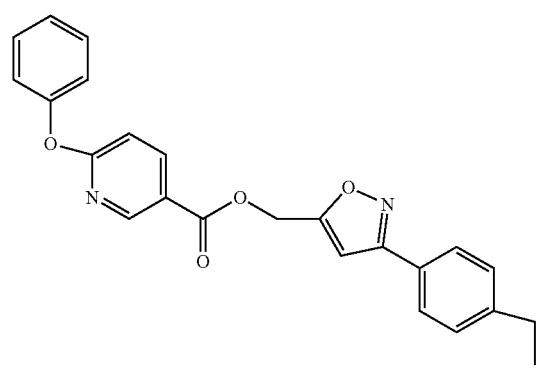
YP-99
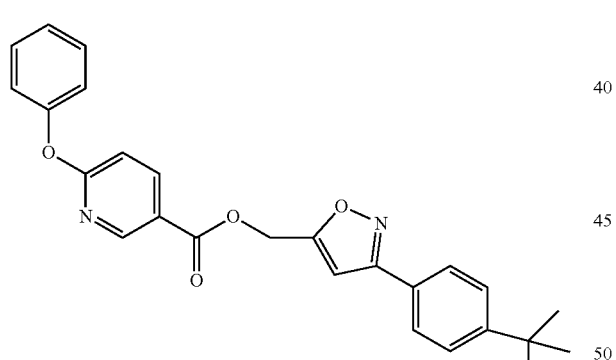
YP-100
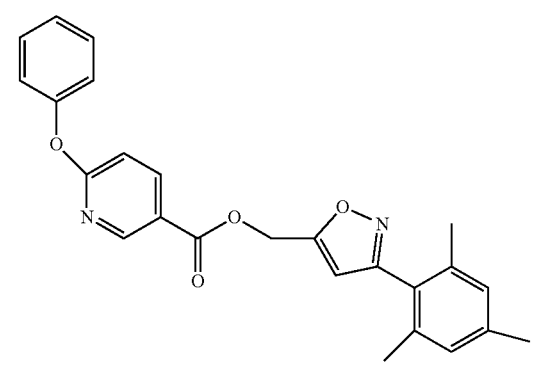
-continued
YP-101
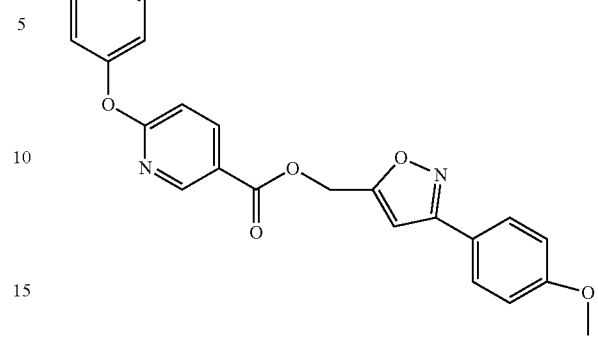
YP-102
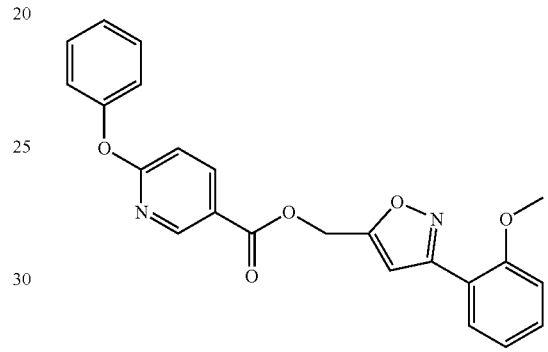
YP-103
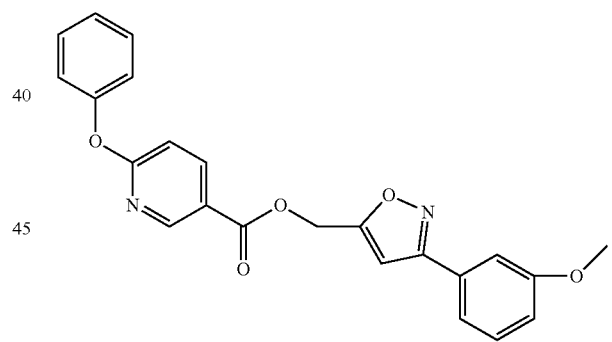
YP-104
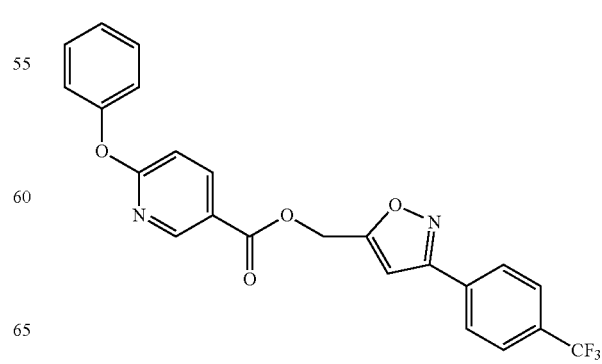

YP-105
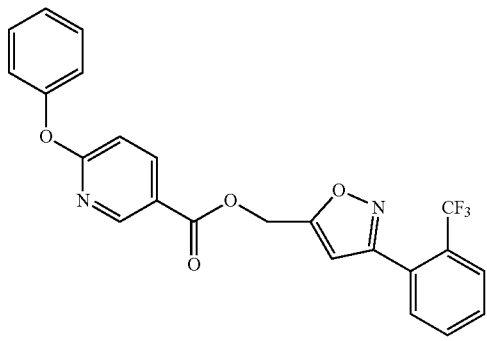
YP-109
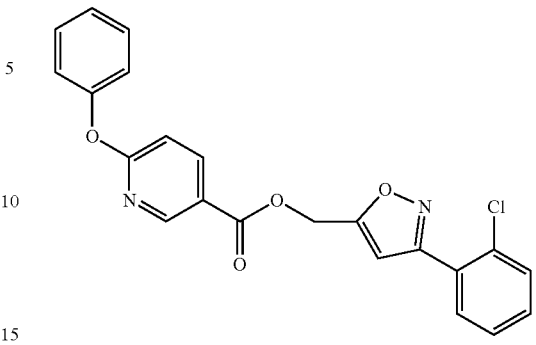
YP-106
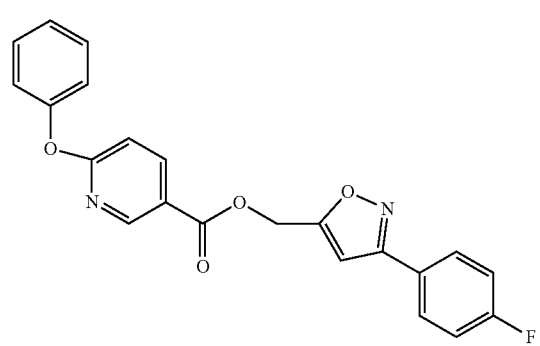
YP-110
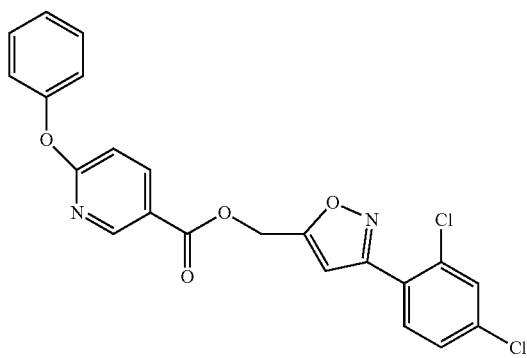
YP-107
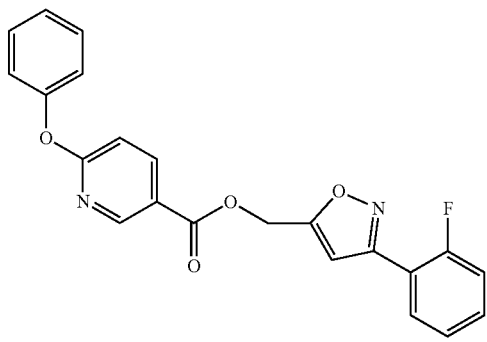
YP-111
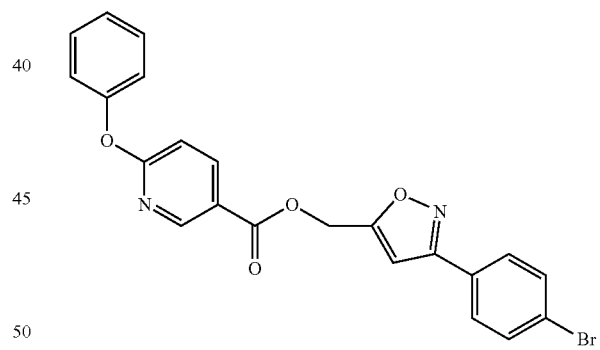
YP-108
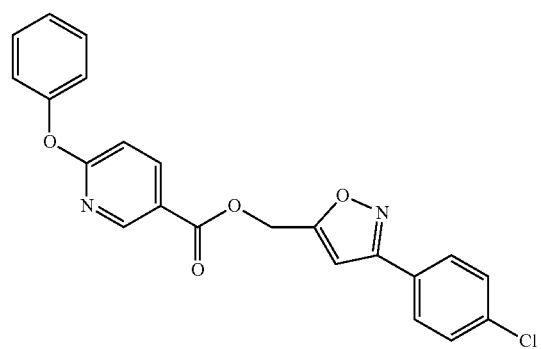
YP-112
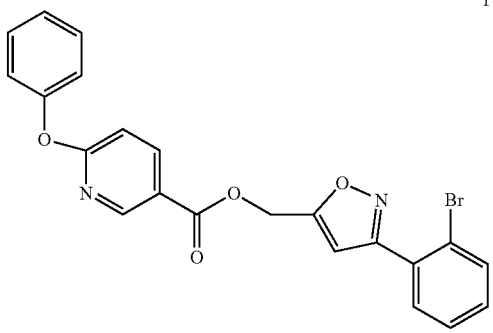

YP-113
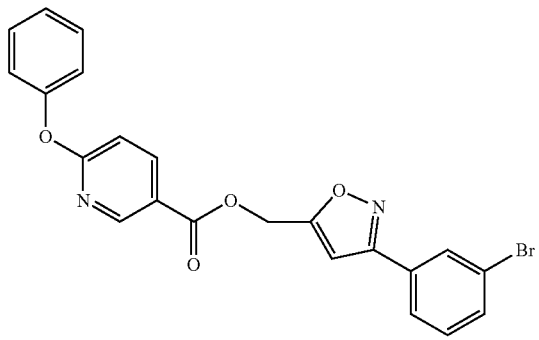
YP-114
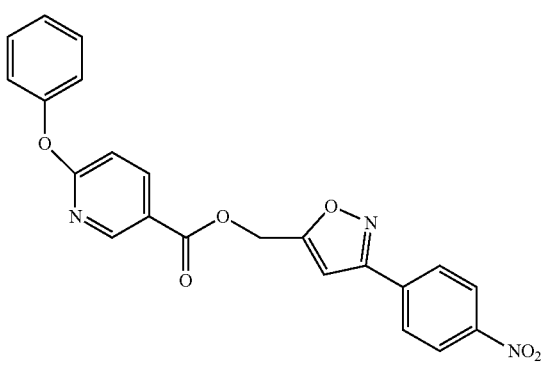
YP-115
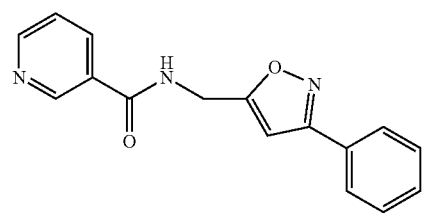
YP-116
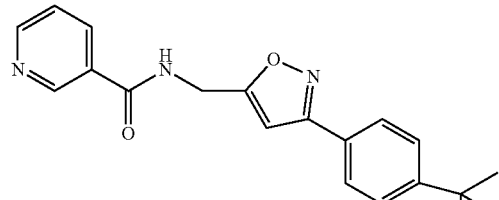
YP-117
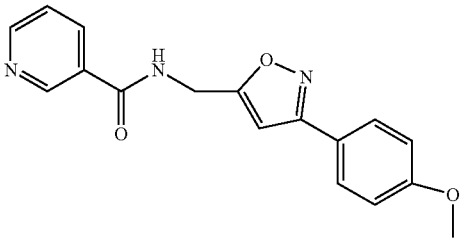
YP-118
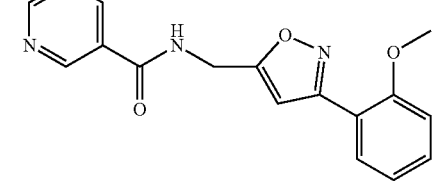
YP-119
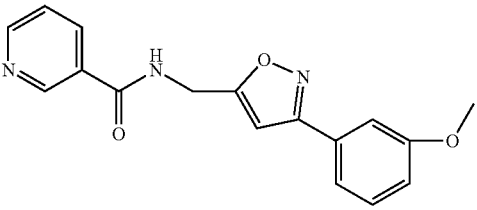
YP-120
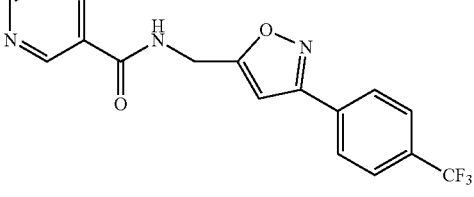
YP-121
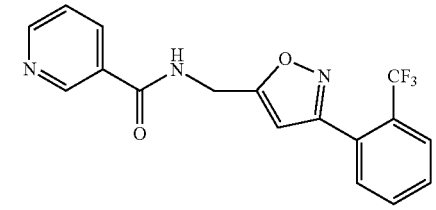
YP-122
YP-123
YP-124

YP-125
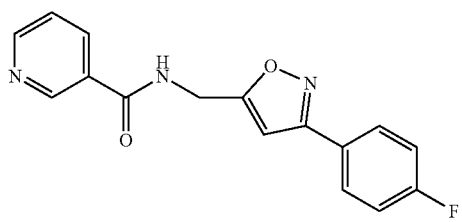
YP-126
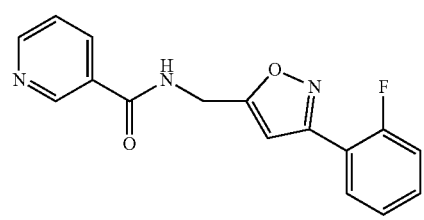
YP-127
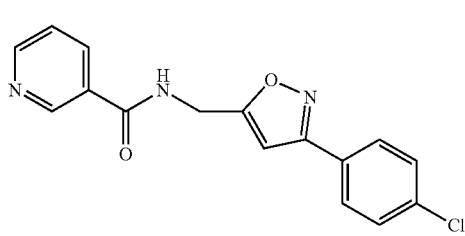
YP-128
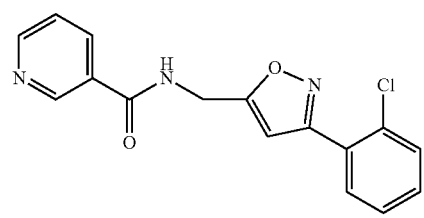
YP-129
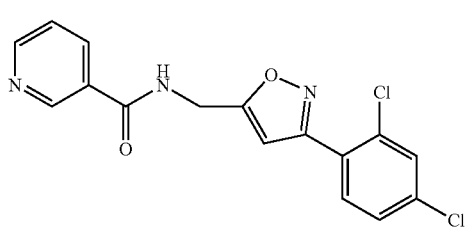
YP-130
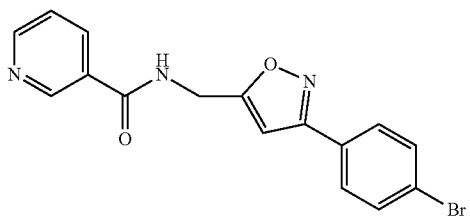
YP-131
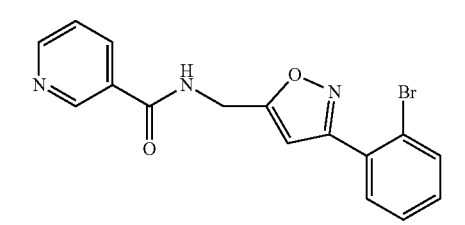
YP-132
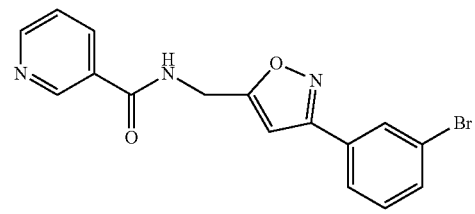
YP-133
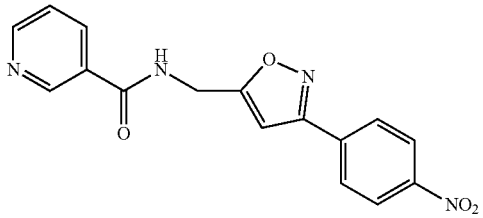
YP-134
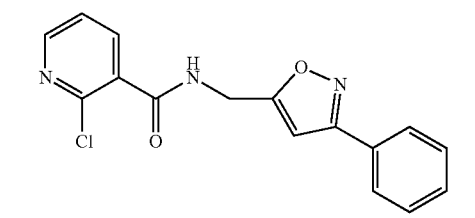
YP-135
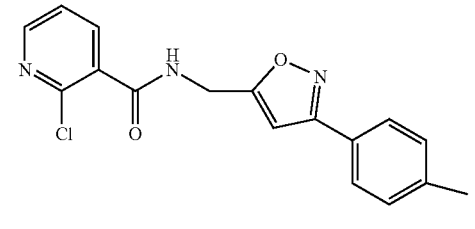
YP-136
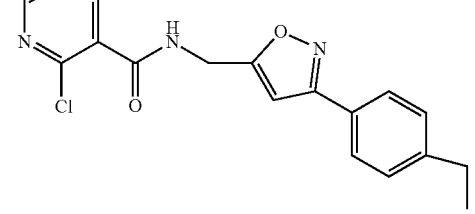
YP-137
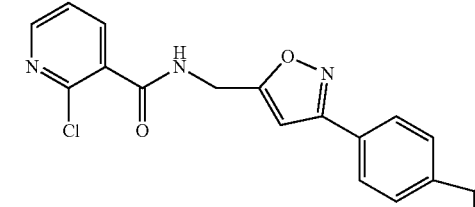
YP-138
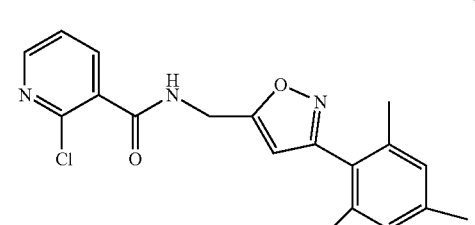

YP-139
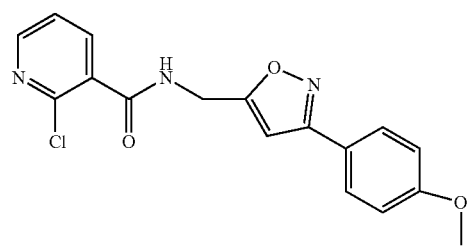
YP-140
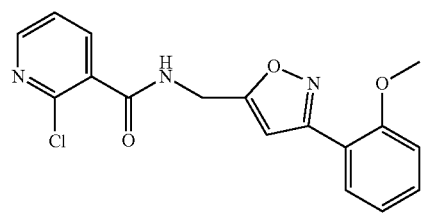
YP-141
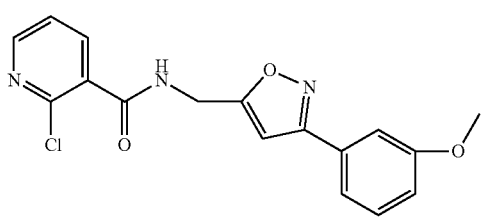
YP-142
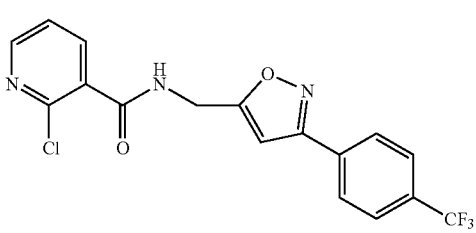
YP-143
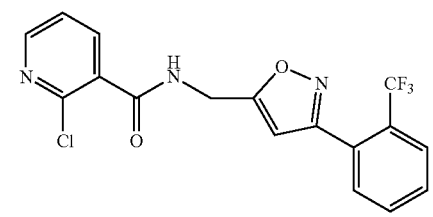
YP-144
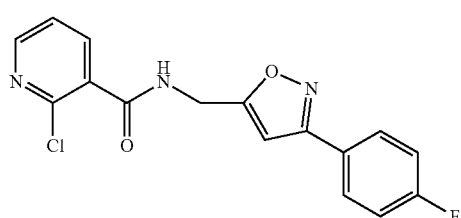
YP-145
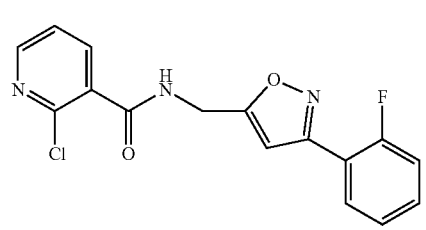
YP-146
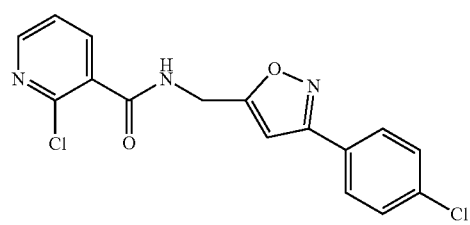
YP-147
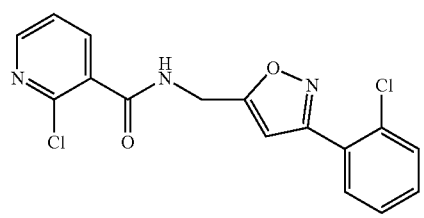
YP-148
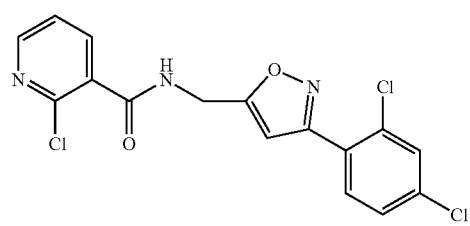
YP-149
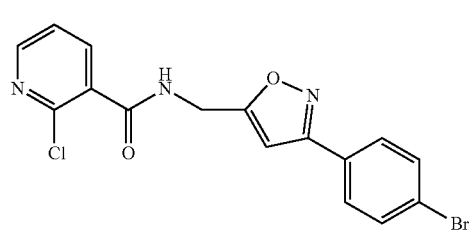
YP-150
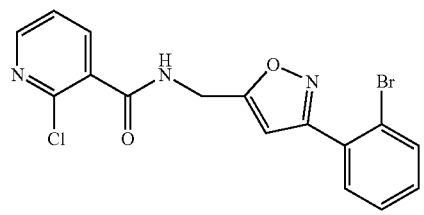
YP-151
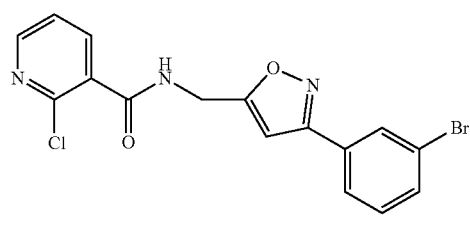
YP-152
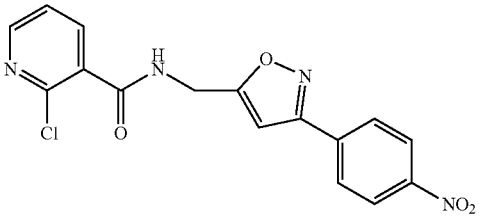

YP-153
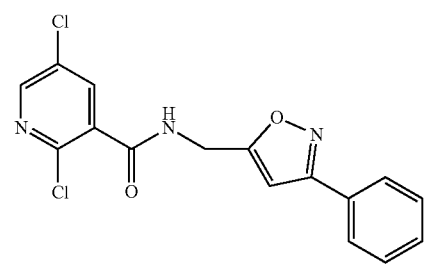
YP-154
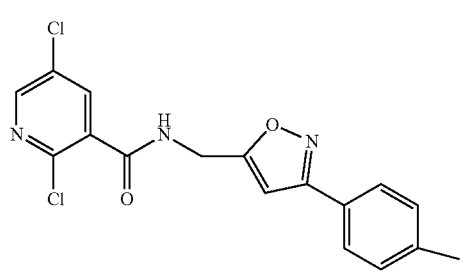
YP-155
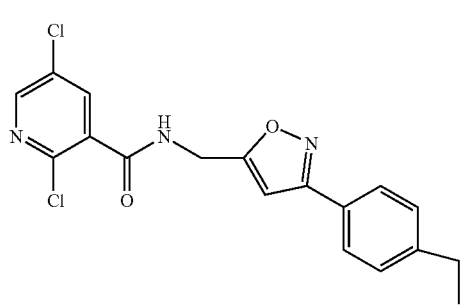
YP-156
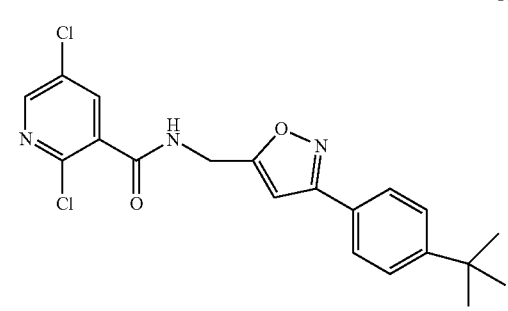
YP-157
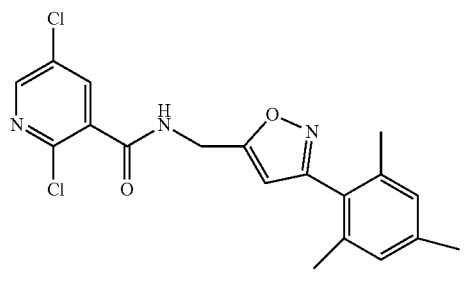
YP-158
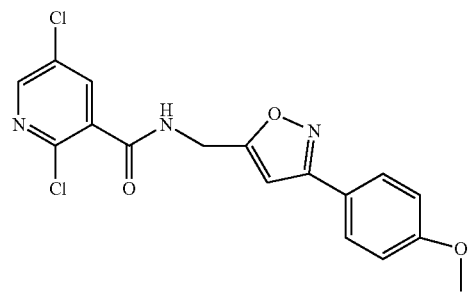
YP-159
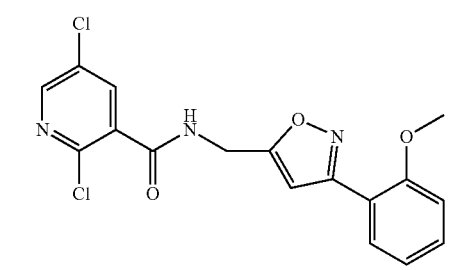
YP-160
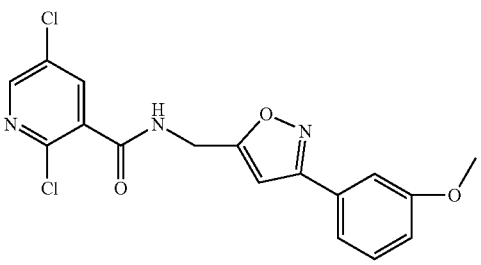
YP-161
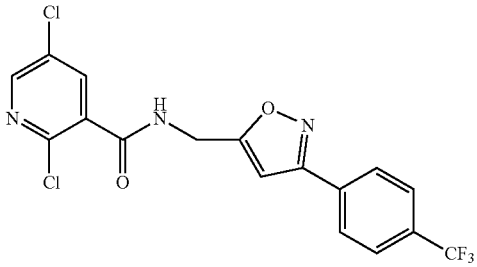
YP-162
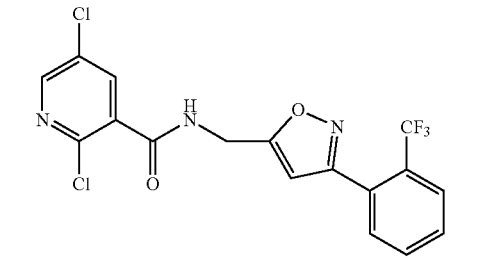
YP-163
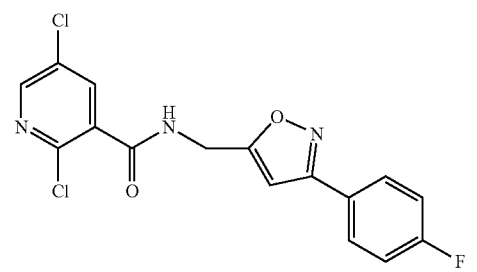

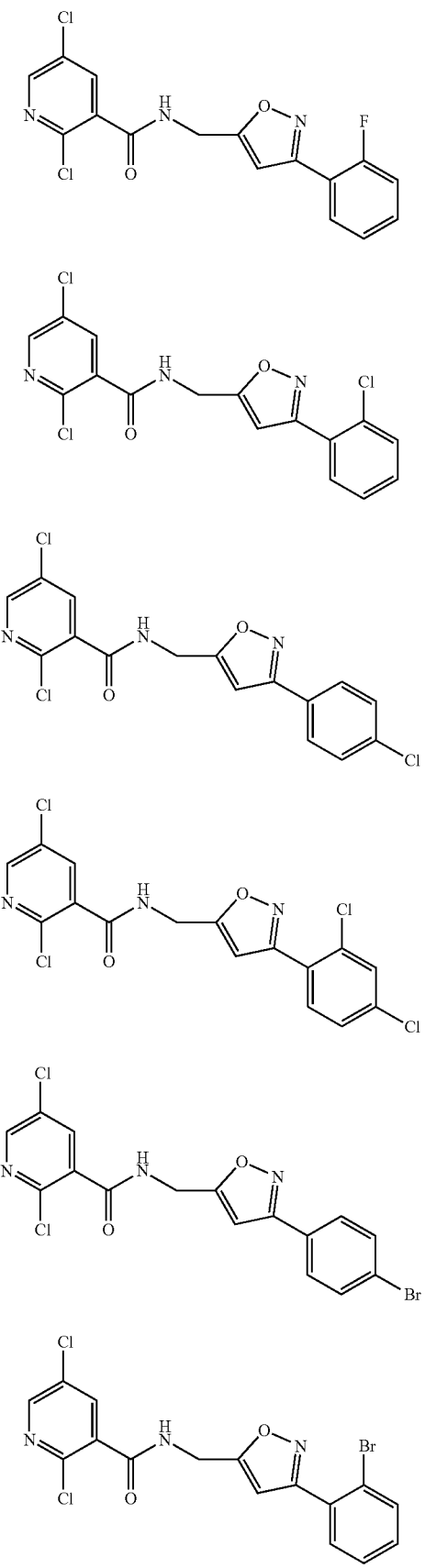
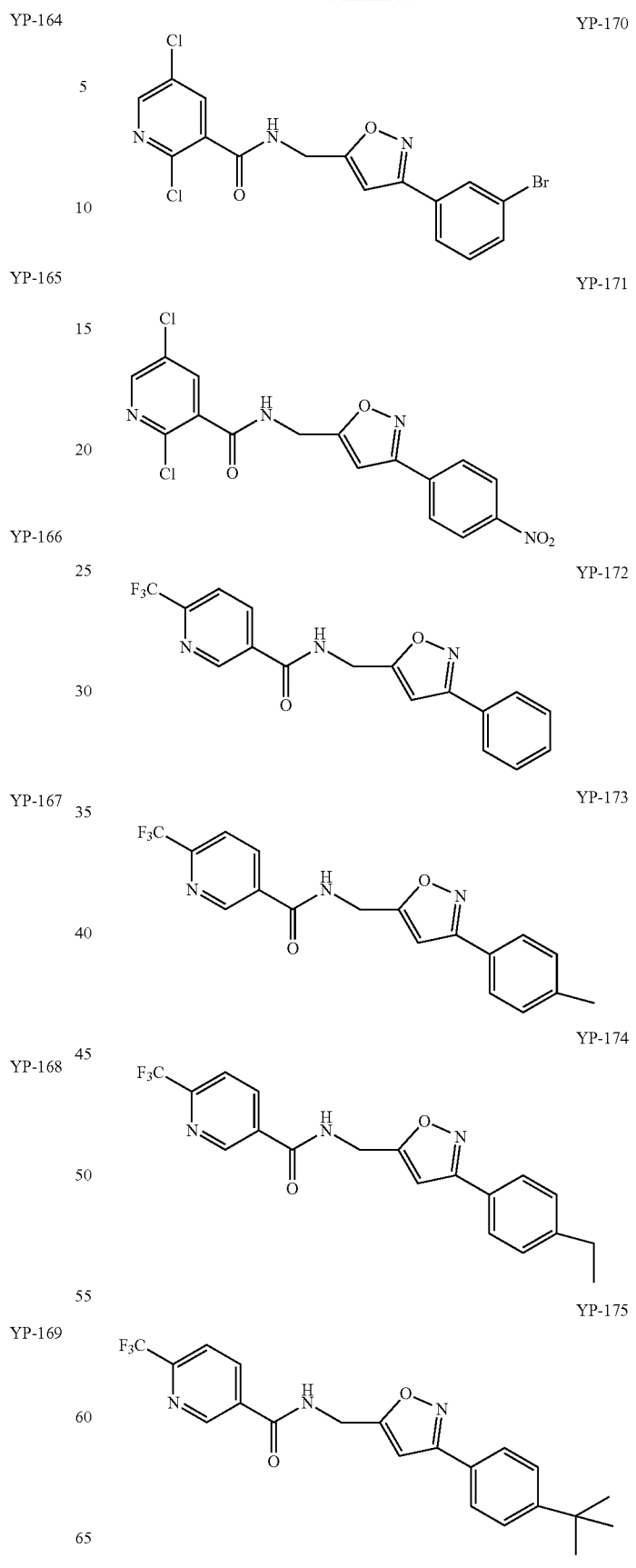

-continued
YP-176
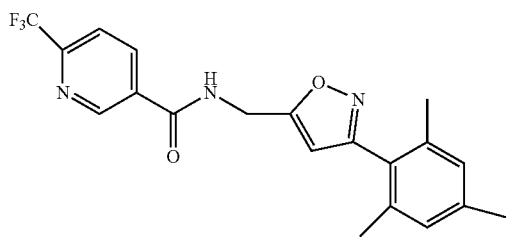
YP-182
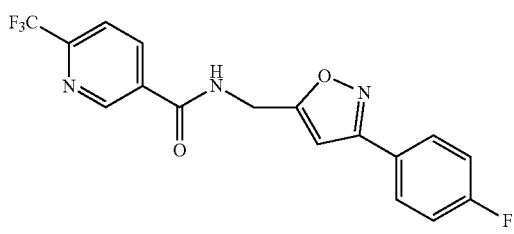
YP-177
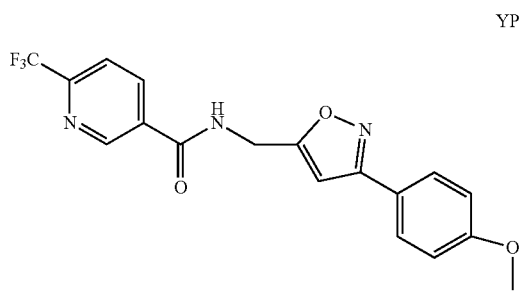
YP-183
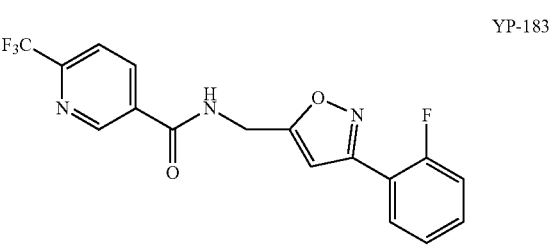
YP-178
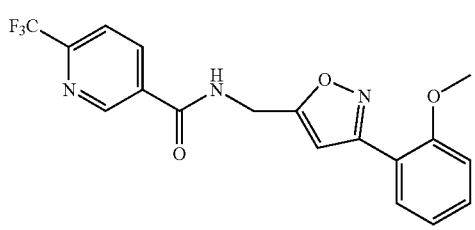
YP-184
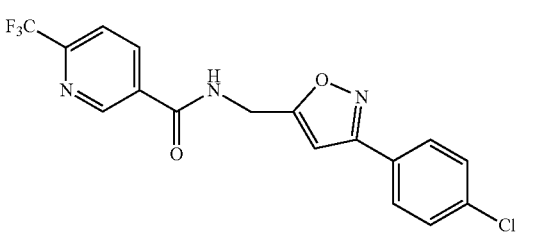
YP-179
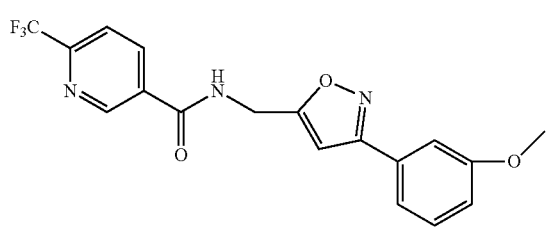
YP-185
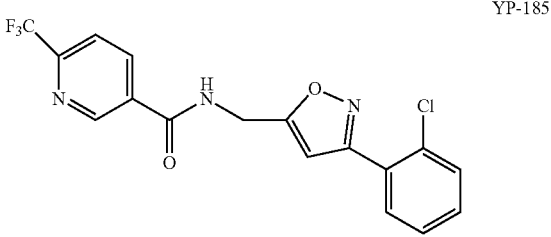
YP-180
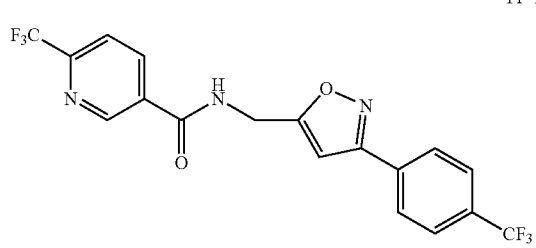
YP-186
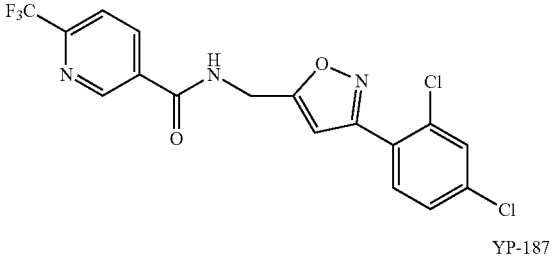
YP-181
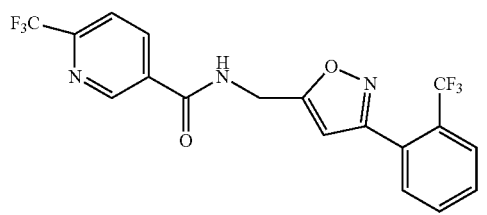
YP-187
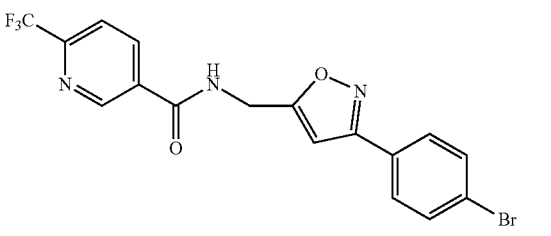

YP-188
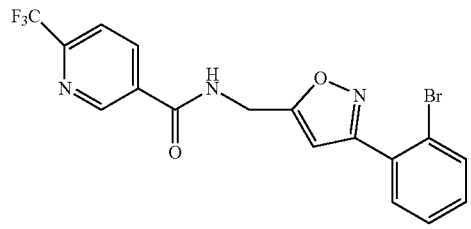
YP-194
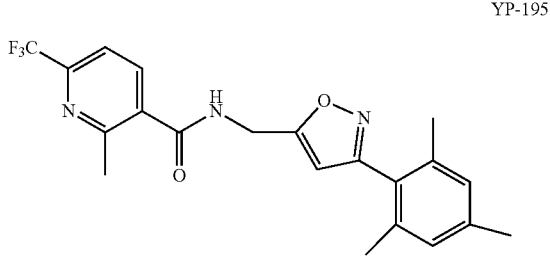
YP-189
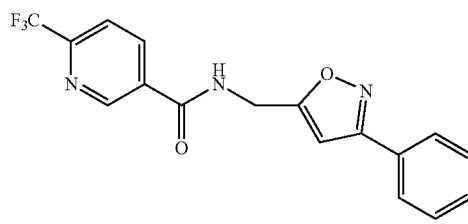
YP-195
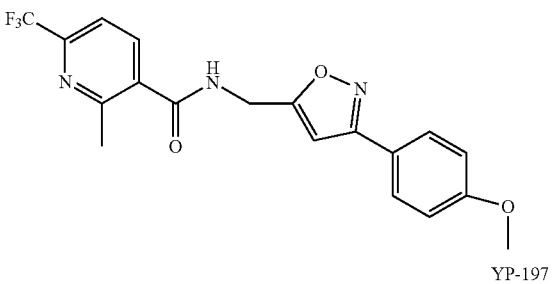
YP-190
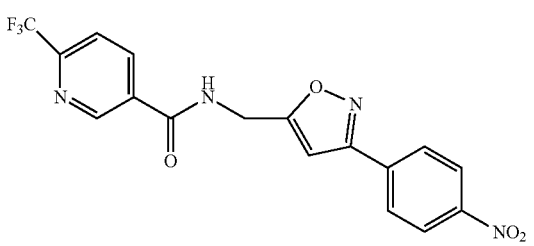
YP-196
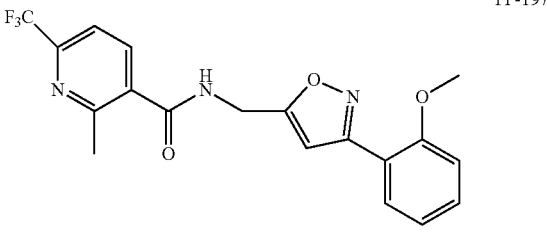
YP-191
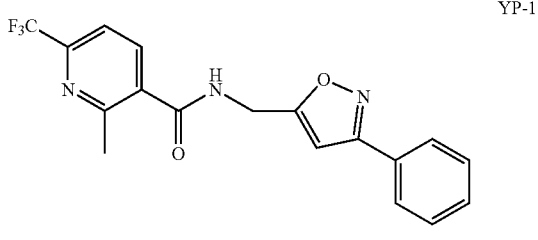
YP-197
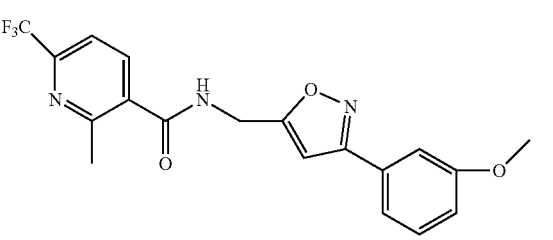
YP-192
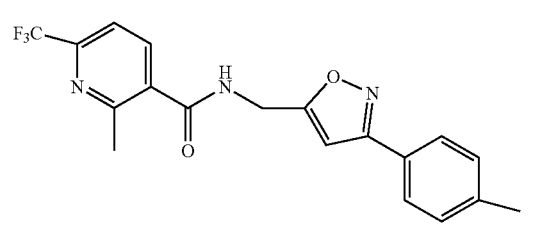
YP-198
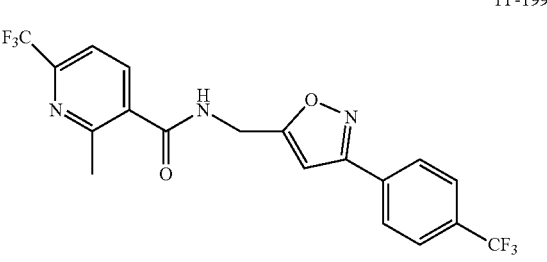
YP-193
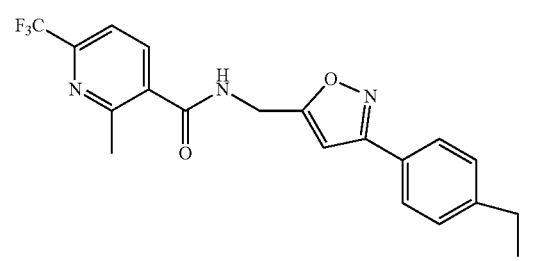
YP-199

YP-200
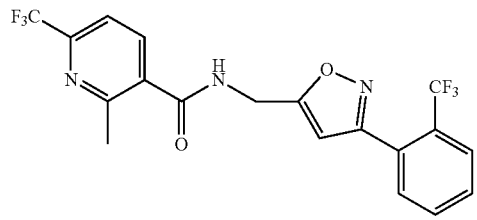
YP-201
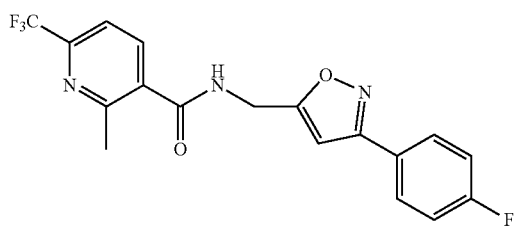
YP-202
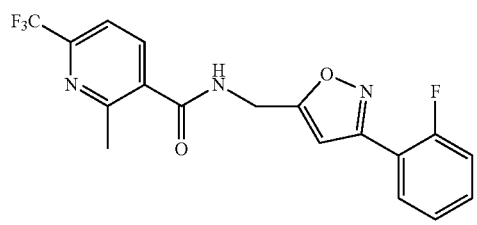
YP-203
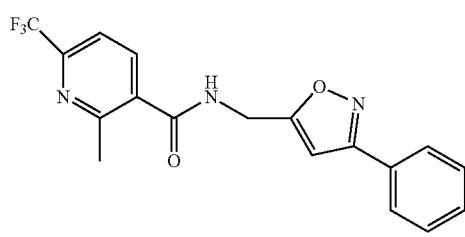
YP-204
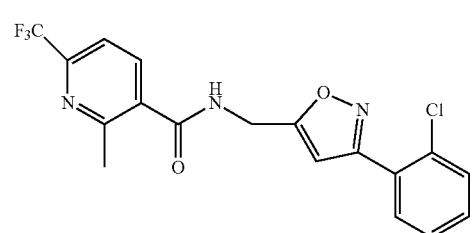
YP-205
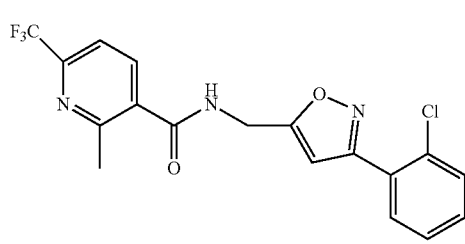
YP-206
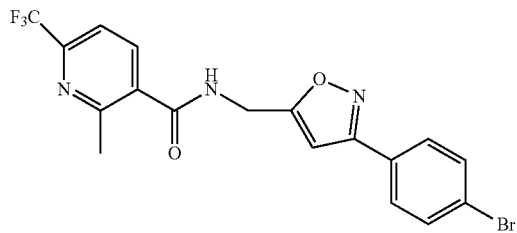
YP-207
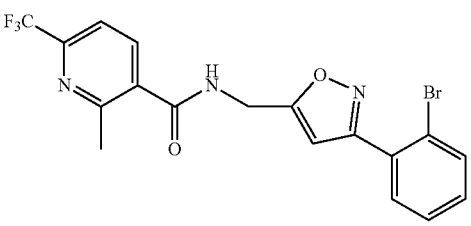
YP-208
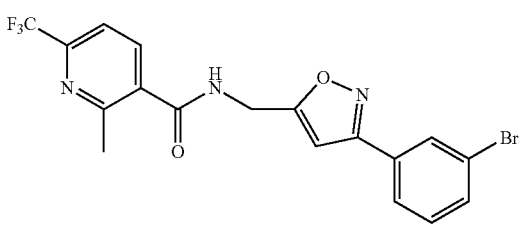
YP-209
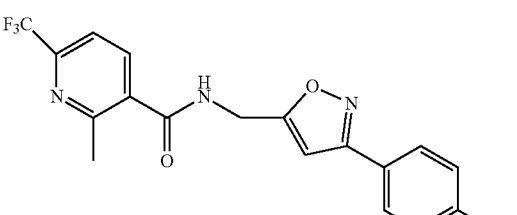
YP-210
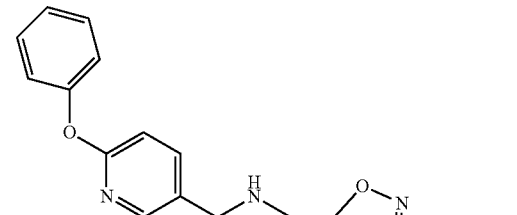

YP-211
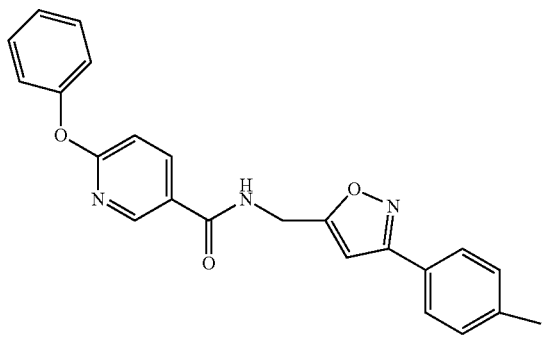
YP-215
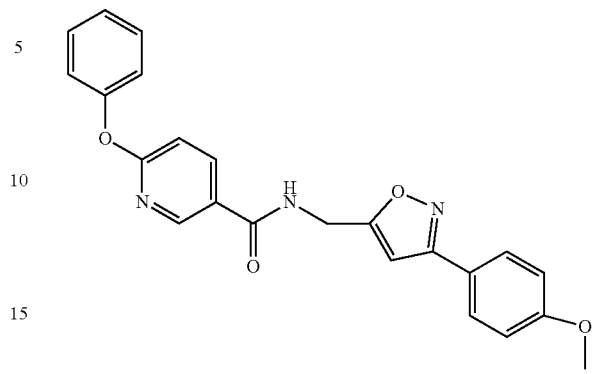
YP-212
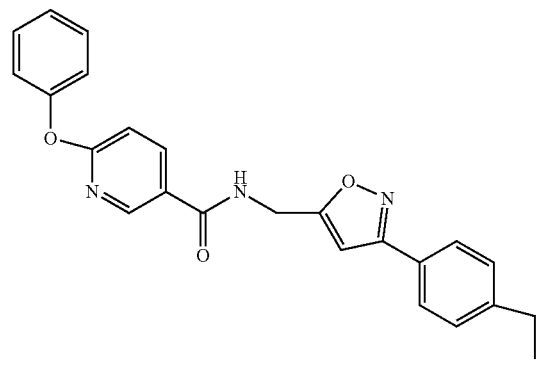
YP-216
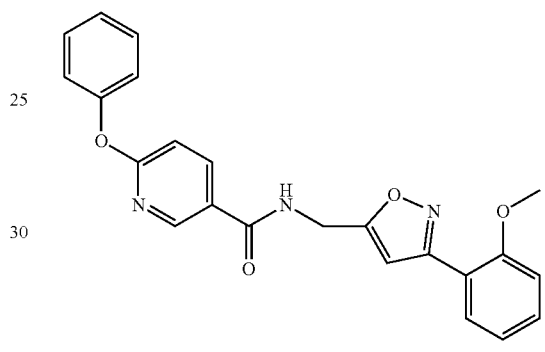
YP-213
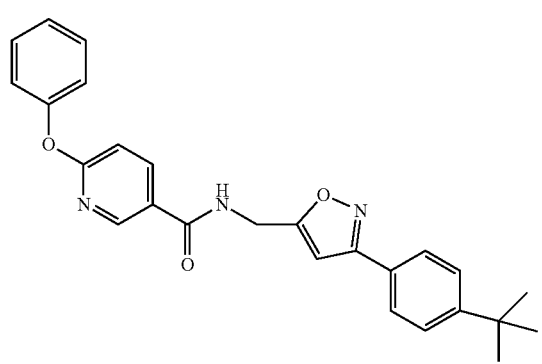
YP-217
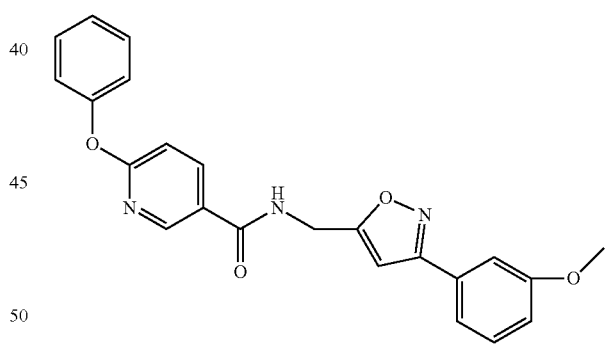
YP-214
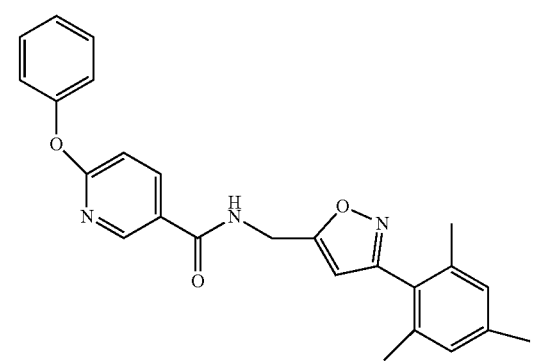
YP-218
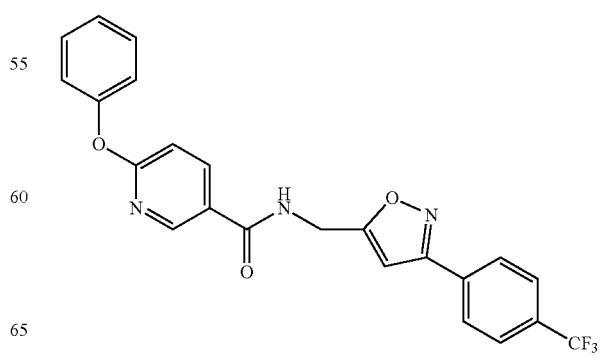

-continued
YP-219
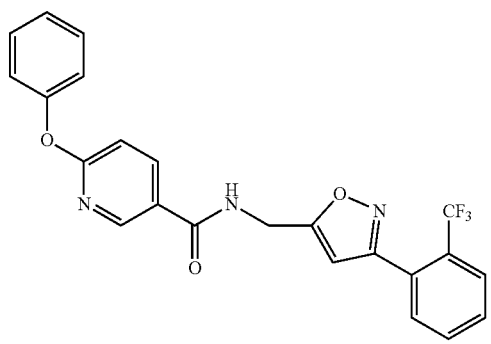
YP-220
YP-221
YP-222
-continued
YP-223
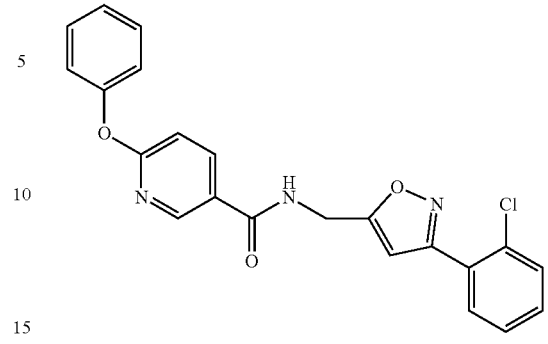
YP-224
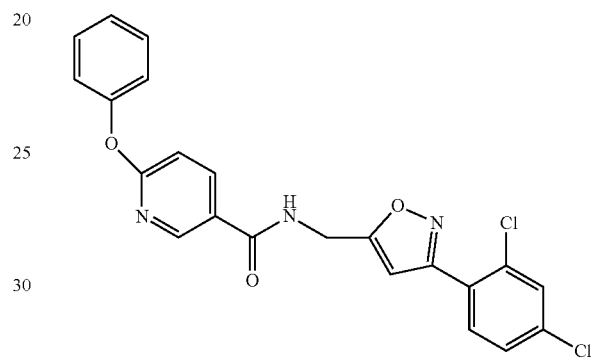
YP-225
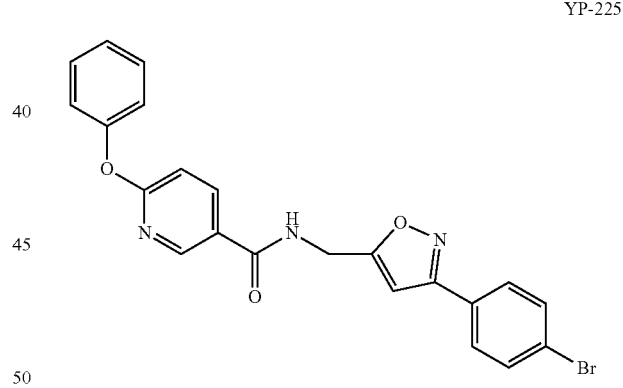
YP-226
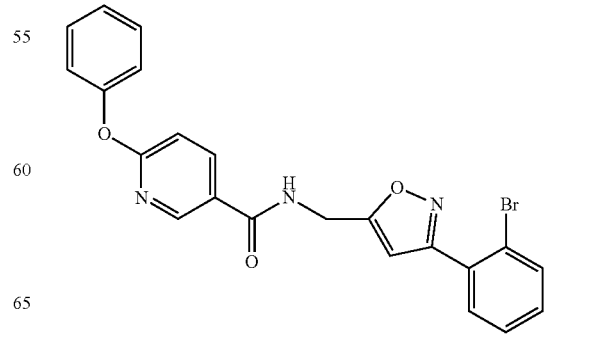

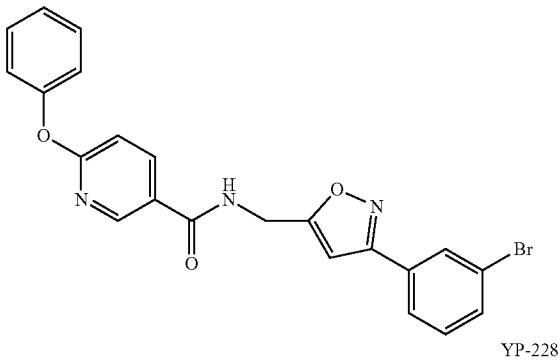

YP-227

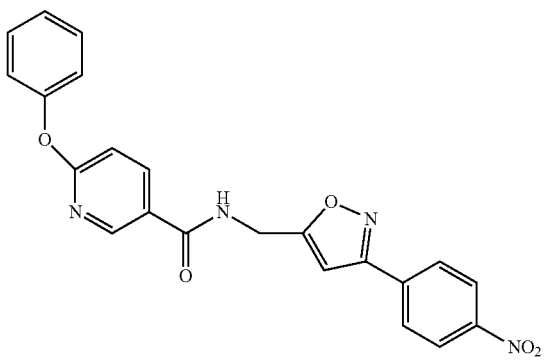

YP-228

The nicotinic acid derivatives represented by formula (I) may respectively form a pharmaceutically acceptable salt with a pharmaceutically acceptable acid. The term "pharmaceutically acceptable salt" includes, but is not limited to, salts formed with inorganic acids, for example, hydrochlorides, phosphates, diphosphates, hydrobromides, sulfates, sulfinates, nitrates, and similar salts; and salts formed with organic acids, for example, lactic acid, oxalate, malate, maleate, fumarate, tartrate, succinate, citrate, lactate, sulfonate, p-toluenesulfonate, 2-hydroxyethylsulfonate, benzoate, salicylate, stearate, trifluoroacetic acid, amino acid salt, or alkanoate such as acetate, salt of HOOC—$(CH_2)_n$—COOH (where n is 1-4), and similar salts. Similarly, pharmaceutically acceptable cations include, but are not limited to, sodium, potassium, calcium, aluminum, lithium and ammonium.

The term "solvate" includes hydrates and alcoholates.

The present invention also provides a pharmaceutical composition, comprising a therapeutically effective amount of one or more of a compound of formula (I), a pharmaceutically acceptable salt thereof, or a solvate thereof.

The pharmaceutical composition further comprises at least one pharmaceutically acceptable adjuvant. The adjuvant may be inert, non-toxic excipients, carriers or diluents. For example, the adjuvant may be one or more selected from the following: disintegrating agents, glidants, lubricants, fillers, adhesives, colorants, effervescents, corrective agents, preservatives, coating materials and the like.

The present invention also provides a pharmaceutical preparation, characterized in that the preparation comprises a therapeutically effective amount of one or more of a compound of formula (I), and a pharmaceutically acceptable salt and solvate thereof.

According to the present invention, the preparation is preferably a solid oral preparation, a liquid oral preparation or an injection.

According to the present invention, the preparation is selected from tablets (dispersible tablets, enteric-coated tablets, chewable tablets, orally disintegrating tablets), capsules, granules, oral solutions, water injection, lyophilized powder injection, large volume parenteral or small infusion solution.

The present invention also provides the use of one or more of a nicotinic acid derivative of formula (I) or a pharmaceutically acceptable salt or a solvate thereof for the preparation of anti-tumor or anti-cancer medicament.

According to the present invention, the tumor or cancer is a cancer caused by overexpression and/or hyperactivity of EGFR. Preferably, the tumor or cancer is selected from bladder cancer, non-small cell lung cancer (NSCLC), ovarian cancer, breast cancer, stomach cancer, esophageal cancer, lung cancer, head and neck cancer, colon cancer, pharyngeal cancer or pancreatic cancer, etc.; and further is preferably non-small cell lung cancer (NSCLC).

The present invention also provides a method of treating a tumor or a cancer by administering an effective amount of one or more of a compound of formula (I), a pharmaceutically acceptable salt thereof, or a solvate thereof to an individual in need thereof.

According to the present invention, the individual in need may be a human or other mammals.

According to the present invention, the tumor or cancer has the definition as described above.

The present invention also provides a process for the preparation of a nicotinic acid derivative as shown in the above formula (I), comprising reacting a compound of formula (III) with a compound of formula (II) to obtain a compound of formula (I):

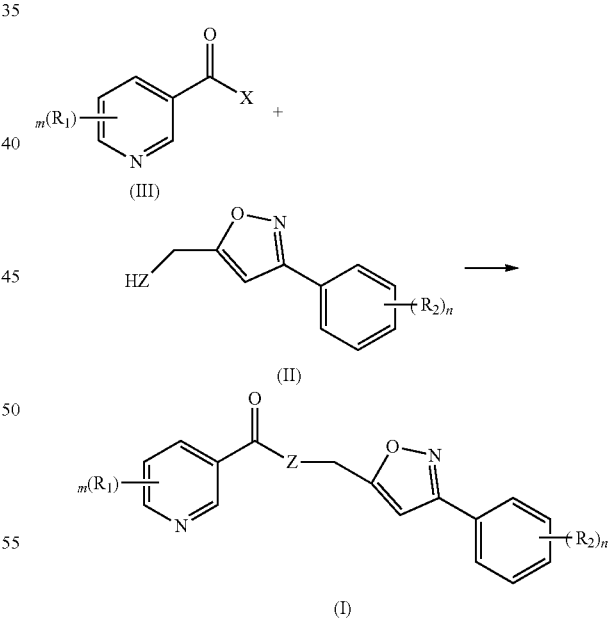

wherein $R_1$, $R_2$, Z, m, and n independently of each other have the definitions described above;

X is selected from a leaving group such as hydroxyl or Cl.

If any protection is desired, any functional group in formula (II) and formula (III) may be protected, and then if necessary, the protecting group may be removed.

If necessary, a pharmaceutically acceptable salt of the compound of formula (I) may be formed.

According to the present invention, the reaction is preferably carried out in an organic solvent, wherein the organic solvent is one or more selected from benzene, toluene, xylene, dichloromethane, chloroform, acetonitrile, dioxane, tetrahydrofuran (THF) or N,N-dimethyl formamide (DMF), and is preferably tetrahydrofuran.

According to the present invention, the temperature of the reaction is from −20 to 120° C., preferably from 0 to 30° C.

According to the present invention, the reaction is preferably carried out under the action of a basic catalyst, wherein the basic catalyst is selected from organic bases or inorganic bases; the organic base is preferably one or more selected from triethylamine, tripropylamine, N,N-Diisopropylethylamine, DMAP, potassium tert-butoxide, sodium tert-butoxide and the like; and the inorganic base is preferably one or more selected from potassium carbonate, cesium carbonate, sodium hydride, sodium carbonate and the like.

According to the present invention, the reaction can also be carried out under the action of a condensation agent, wherein the condensation agent can be for example dicyclohexylcarbodiimide (DCC), carbonyl diimidazole (CDI) or 1-(3-dimethylaminopropyl)-3-ethylcarbodiimide hydrochloride (EDCI.HCl).

According to the present invention, an activator may be further added to the condensation agent, wherein the activation agent can be for example 1-hydroxybenzotriazole (HOBT), N,N-diisopropylethylamine or 4-dimethylaminopyridine (DMAP).

The term "effective amount" refers to an amount of the at least one compound and/or at least one pharmaceutically acceptable salt effective to "treat" one disease or discomfort of an individual. In the case of cancer, an effective amount can reduce the number of cancer or tumor cells; reduce the size of the tumor; inhibit or prevent the invasion of tumor cells into peripheral organs, for example, the spreading of the tumor into soft tissue or bones; inhibit or prevent tumor metastasis; inhibit or prevent tumor growth; alleviate one or more cancer-related symptoms to some extent; reduce morbidity and mortality; improve quality of life; or can achieve the combination of the above effects. An effective amount may be an amount to reduce the disease symptoms by inhibiting EGFR activity. For cancer treatment, the effect of in vivo experiments can be measured by assessing for example survival time, time to disease progression (TDP), response rate (RR), sustained response period and/or quality of life.

A person skilled in the art has realized that an effective amount may vary depending on the route of administration, the dose of the excipient, and the combination with other drugs.

The term "effective amount" also refers to a dosage of the at least one compound and/or at least one pharmaceutically acceptable salt thereof effective to inhibit overexpression and/or hyperactivity of EGFR.

Beneficial Effects

The compounds of the present invention have anti-tumor and anti-cancer activity, particularly have a strong inhibitory activity on human lung cancer cell line A549, colorectal cancer cell line HCT116 and breast cancer cell line MCF-7. For example, compound YP-78, compound YP-89, compound YP-108, compound YP-44, compound YP-63, compound YP-51, and compound YP-73 have a strong inhibitory activity on lung cancer cell line A549, colorectal cancer cell line HCT116 and breast cancer cell line MCF-7.

The compounds of the present invention have broad-spectrum anti-cancer and anti-tumor activity and can be used as candidate drugs or leading compounds for the treatment of tumors and cancers.

Embodiments

The present invention will now be described in further detail with reference to the following examples. It is to be understood that the following examples are not to be taken as limiting the scope of the invention, and that any improvements made on the basis of the present invention are not contrary to the spirit of the invention.

Wherein the synthesis of intermediate and target compound is described in the examples as representative, and the synthesis of the remaining intermediates and target compounds is the same as that of the representative compounds.

Instruments and Reagents:

The following instruments were used in the present invention: AVANCE III Nuclear Magnetic Resonance Spectrometer (400 MHz, DMSO-$d_6$, TMS as internal standard), ion trap LCMS analyzer (DECAX-30000 LCQ Deca XP), XT5 digital display micro melting point determinator (Beijing Keyi Electro-Optical Instrument Factory, temperature without correction), and adjustable wavelength microplate reader (Molecular Devies SPECTRAMAX190). Adjustable wavelength microplate reader (Molecular Devies SPECTRAMAX190). Chemical reagents were all commercially available analytically pure or chemically pure reagents. RPMI1640 was available from Gibco Corporation, and thiazole blue (3-(4,5-dimethylthiazol-2-yl)-2,5-diphenyltetrazolium bromide, MTT) was available from Sigma Corporation. The other reagents were all commercially available analytically pure, and were not treated prior to use unless otherwise specified. Tetrahydrofuran was treated with a dry molecular sieve prior to use.

PREPARATION EXAMPLE 1

Synthesis of Intermediate (II-1) and Intermediate (II-2)

The intermediates were prepared using substituted benzaldehyde as raw material, and through the synthesis of oxime, 1,3-dipolar cycloaddition reaction, methanesulfonyl esterification reaction, azide, and reduction reaction. See the following process:

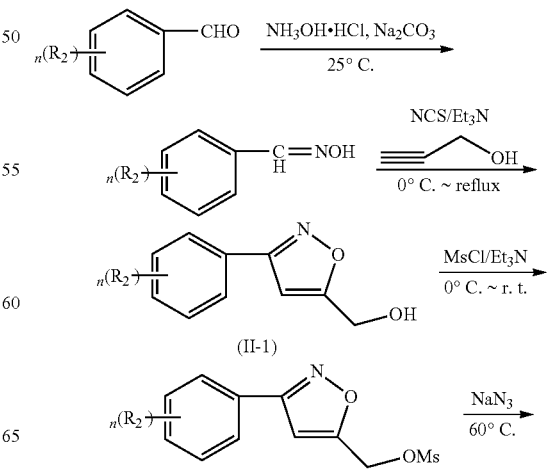

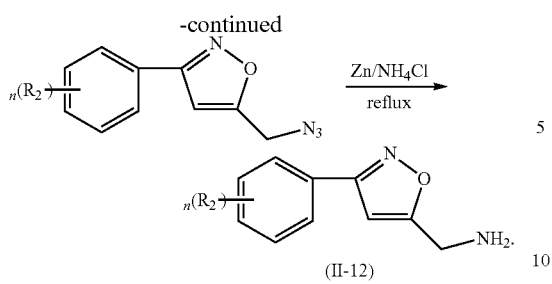

The specific synthesis of intermediate (II-1) and intermediate (II-2) can be found in Chinese patent applications CN103360382A, CN103664991A and CN103601762A, all of which are incorporated herein in full text.

According to the present invention, for compound wherein Z is other substituent, for example, NR3 or S, the corresponding substituted aminopropynyl compound or propynyl mercaptan can be used as starting material, and preparation is carried out according to the preparation process for the intermediate (II-2).

EXAMPLE 1

Synthesis of Nicotinic Acid Derivative of Formula (I)

The reaction of nicotinic acid and 3-phenyl-5-hydroxymethyl-isoxazole was taken as an example.

Synthesis of [(3-phenyl-isoxazol-5-yl)-methyl]-pyridine-3-carboxylate (YP-1)

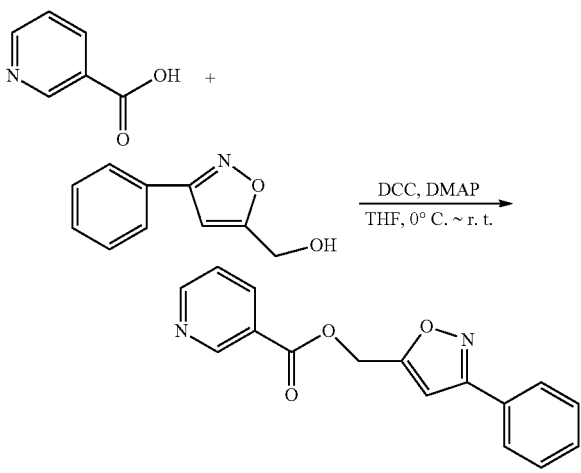

0.123 g (1 mmol) of nicotinic acid and 0.206 g (1 mmol) of DCC were added to a 50 mL round bottom flask, followed by the addition of 10 mL of dry THF, after reaction under stirring for 30 min in an ice bath, a solution of 0.175 g (1 mmol) of 3-phenyl-hydroxymethyl-isoxazole and 0.122 g (1 mmol) of DMAP in 10 mL of THF was slowly added dropwise to the reaction system, and after reaction under stirring for 30 min in an ice bath, the reaction was naturally brought to room temperature. After the reaction was completed under TLC detection, the reaction liquid was concentrated in vacuo and the residue was directly subjected to column separation (V (petroleum ether): V (ethyl acetate) =5:1 to 2:1) to obtain the target compound [(3-phenyl-isoxazol-5-yl)-methyl]-pyridine-3-carboxylate (YP-1). Other compounds having similar structure can be prepared according to the process for the synthesis of [(3-phenyl-isoxazol-5-yl)-methyl]-pyridine-3-carboxylate (YP-1).

EXAMPLE 2

Synthesis of Nicotinic Acid Amide Derivatives Represented by the Formula (I)

The reaction of nicotinic acid and 3-phenyl-5-aminomethyl-isoxazole was taken as an example.

Synthesis of N-[(3-phenyl-isoxazol-5-yl)-methyl]-pyridine-3-carboxamide (YP-115)

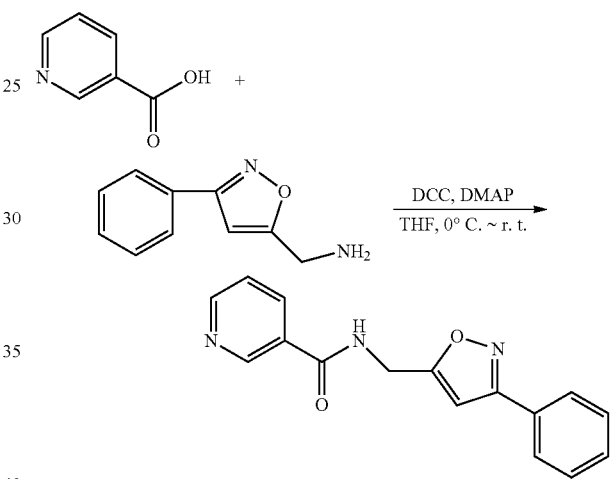

0.123 g (1 mmol) of nicotinic acid, 0.206 g (1 mmol) of DCC and 0.135 g (1 mmol) of HOBT were added to a 50 mL round bottom flask, followed by the addition of 10 mL of dry THF, after reaction under stirring for 30 min in an ice bath, a solution of 0.174 g (1 mmol) of 3-phenyl-5-aminomethyl-isoxazole and 0.122 g (1 mmol) of DMAP in 10 mL of THF was slowly added dropwise to the reaction system, and after reaction under stirring for 30 min in an ice bath, the reaction was naturally brought to room temperature. After the reaction was completed under TLC detection, the reaction liquid was concentrated in vacuo and the residue was directly subjected to column separation (V (petroleum ether): V (ethyl acetate)=5:1 to 2:1) to obtain the target compound N-[(3-phenyl-isoxazol-5-yl)-methyl]-pyridine-3-carboxamide (YP-115). Other compounds having similar structure were prepared according to the synthesis process for N-[(3-phenyl-isoxazol-5-yl)-methyl]-quinoline-2-carboxamide (YP-115).

The structure of the nicotinic acid derivatives of formula (I) was characterized by IR, $^1$H NMR, ESI-MS and other analytical methods. Spectral data of the preferred compounds were presented in tables:

The structure, number and physical constants of the preferred compounds were shown in the following tables:

TABLE 1

Structure, number and mass spectrum of preferred compounds

| No. | MS (m/z, 100%) | No. | MS (m/z, 100%) |
|---|---|---|---|
| YP-1 | 281 ([M + H]$^+$, 20) | YP-2 | 294 ([M]$^+$, 10) |
| YP-3 | 309 ([M + H]$^+$, 50) | YP-4 | 336 ([M]$^+$, 16) |
| YP-5 | 345 ([M + 23]$^+$, 48) | YP-6 | 310 ([M]$^+$, 20) |
| YP-7 | 310 ([M]$^+$, 10) | YP-8 | 310 ([M]$^+$, 50) |
| YP-9 | 348 ([M]$^+$, 20) | YP-10 | 348 ([M]$^+$, 45) |
| YP-11 | 299 ([M + H]$^+$, 80) | YP-12 | 299 ([M + H]$^+$, 60) |
| YP-13 | 315 ([M + H]$^+$, 80) | YP-14 | 315 ([M + H]$^+$, 60) |
| YP-15 | 351 ([M + 2]$^+$, 80) | YP-16 | 359 ([M]$^+$, 70) |
| YP-17 | 359 ([M]$^+$, 50) | YP-18 | 359 ([M]$^+$, 20) |
| YP-19 | 325 ([M]$^+$, 100) | YP-20 | 349 ([M]$^+$, 5) |
| YP-21 | 362 ([M − H]$^−$, 5) | YP-22 | 377 ([M]$^+$, 30) |
| YP-23 | 406 ([M + H]$^+$, 80) | YP-24 | 391 ([M]$^+$, 80) |
| YP-25 | 382 ([M + 3]$^+$, 100) | YP-26 | 380 ([M + 1]$^+$, 100) |
| YP-27 | 380 ([M + 1]$^+$, 80) | YP-28 | 418 ([M + H]$^+$, 50) |
| YP-29 | 418 ([M + H]$^+$, 76) | YP-30 | 368 ([M + 1]$^+$, 100) |
| YP-31 | 368 ([M + 1]$^+$, 80) | YP-32 | 407 ([M + H]$^+$, 10) |
| PY-33 | 385 ([M + 2]$^+$, 5) | YP-34 | 418 ([M]$^+$, 40) |
| YP-35 | 428 ([M]$^+$, 10) | YP-36 | 428 ([M]$^+$, 50) |
| YP-37 | 428 ([M]$^+$, 60) | YP-38 | 394 ([M]$^+$, 100) |
| YP-39 | 348 ([M]$^+$, 80) | YP-40 | 362 ([M + H]$^+$, 10) |
| YP-41 | 376 ([M]$^+$, 70) | YP-42 | 404 ([M]$^+$, 80) |
| YP-43 | 391 ([M + H]$^+$, 100) | YP-44 | 379 ([M + H]$^+$, 70) |
| YP-45 | 379 ([M + H]$^+$, 100) | YP-46 | 378 ([M]$^+$, 70) |
| YP-47 | 416 ([M]$^+$, 100) | YP-48 | 417 ([M + H]$^+$, 80) |
| YP-49 | 366 ([M]$^+$, 100) | YP-50 | 366 ([M]$^+$, 50) |
| YP-51 | 382 ([M]$^+$, 10) | YP-52 | 382 ([M]$^+$, 30) |
| YP-53 | 417 ([M]$^+$, 20) | YP-54 | 429 ([M + 2]$^+$, 5) |
| YP-55 | 427 ([M]$^+$, 50) | YP-56 | 427 ([M]$^+$, 15) |
| YP-57 | 394 ([M + H]$^+$, 50) | YP-58 | 349 ([M]$^+$, 50) |
| YP-59 | 363 ([M + H]$^+$, 70) | YP-60 | 377 ([M + H]$^+$, 80) |
| YP-61 | 405 ([M + H]$^+$, 70) | YP-62 | 391 ([M + H]$^+$, 100) |
| YP-63 | 378 ([M]$^+$, 100) | YP-64 | 378 ([M]$^+$, 100) |
| YP-65 | 378 ([M]$^+$, 80) | YP-66 | 416 ([M]$^+$, 70) |
| YP-67 | 416 ([M]$^+$, 50) | YP-68 | 366 ([M]$^+$, 50) |
| YP-69 | 366 ([M]$^+$, 100) | YP-70 | 383 ([M]$^+$, 80) |
| YP-71 | 383 ([M]$^+$, 100) | YP-72 | 417 ([M]$^+$, 50) |
| YP-73 | 427 ([M]$^+$, 50) | YP-74 | 427 ([M]$^+$, 70) |
| YP-75 | 427 ([M]$^+$, 100) | YP-76 | 393 ([M]$^+$, 100) |
| YJ-77 | 362 ([M]$^+$, 20) | YP-78 | 376 ([M]$^+$, 60) |
| YP-79 | 390 ([M]$^+$, 60) | YP-80 | 418 ([M]$^+$, 50) |
| YP-81 | 404 ([M]$^+$, 50) | YP-82 | 392 ([M]$^+$, 50) |
| YP-83 | 392 ([M]$^+$, 80) | YP-84 | 392 ([M]$^+$, 100) |
| YP-85 | 430 ([M]$^+$, 80) | YP-86 | 430 ([M]$^+$, 60) |
| YP-87 | 380 ([M]$^+$, 40) | YP-88 | 380 ([M]$^+$, 20) |
| YP-89 | 397 ([M]$^+$, 70) | YP-90 | 397 ([M]$^+$, 90) |
| YP-91 | 431 ([M]$^+$, 80) | YP-92 | 441 ([M]$^+$, 100) |
| YP-93 | 441 ([M]$^+$, 100) | YP-94 | 441 ([M]$^+$, 80) |
| YP-95 | 407 ([M]$^+$, 100) | YP-96 | 372 ([M]$^+$, 100) |
| YP-97 | 386 ([M]$^+$, 100) | YP-98 | 401 ([M + H]$^+$, 100) |
| YP-99 | 428 ([M]$^+$, 70) | YP-100 | 414 ([M]$^+$, 50) |
| YP-101 | 402 ([M]$^+$, 100) | YP-102 | 402 ([M]$^+$, 80) |
| YP-103 | 402 ([M]$^+$, 50) | YP-104 | 440 ([M]$^+$, 50) |
| YP-105 | 440 ([M]$^+$, 80) | YP-106 | 390 ([M]$^+$, 70) |
| YP-107 | 390 ([M]$^+$, 90) | YP-108 | 407 ([M]$^+$, 80) |
| YP-109 | 407 ([M]$^+$, 80) | YP-110 | 441 ([M]$^+$, 100) |
| YP-111 | 451 ([M]$^+$, 80) | YP-112 | 451 ([M]$^+$, 60) |
| YP-113 | 451 ([M]$^+$, 70) | YP-114 | 417 ([M]$^+$, 100) |
| YP-115 | 280 ([M + H]$^+$, 70) | YP-116 | 294 ([M + H]$^+$, 100) |
| YP-117 | 308 ([M + H]$^+$, 50) | YP-118 | 336 ([M + H]$^+$, 16) |
| YP-119 | 344 ([M + 23]$^+$, 48) | YP-120 | 310 ([M + H]$^+$, 80) |
| YP-121 | 310 ([M + H]$^+$, 80) | YP-122 | 309 ([M]$^+$, 50) |
| YP-123 | 347 ([M]$^+$, 70) | YP-124 | 348 ([M + H]$^+$, 45) |
| YP-125 | 298 ([M + H]$^+$, 80) | YP-126 | 298 ([M + H]$^+$, 60) |
| YP-127 | 314 ([M + H]$^+$, 80) | YP-128 | 314 ([M + H]$^+$, 60) |
| YP-129 | 350 ([M + 2]$^+$, 80) | YP-130 | 359 ([M + H]$^+$, 70) |
| YP-131 | 359 ([M + H]$^+$, 50) | YP-132 | 359 ([M + H]$^+$, 20) |
| YP-133 | 325 ([M + H]$^+$, 100) | YP-134 | 349 ([M + H]$^+$, 89) |
| YP-135 | 362 ([M]$^+$, 25) | YP-136 | 377 ([M + H]$^+$, 70) |
| YP-137 | 405 ([M + H]$^+$, 100) | YP-138 | 391 ([M + H]$^+$, 80) |
| YP-139 | 380 ([M + H]$^+$, 100) | YP-140 | 379 ([M + H]$^+$, 100) |
| YP-141 | 379 ([M + H]$^+$, 80) | YP-142 | 417 ([M + H]$^+$, 50) |
| YP-143 | 417 ([M + H]$^+$, 76) | YP-144 | 367 ([M + H]$^+$, 100) |
| YP-145 | 367 ([M + H]$^+$, 80) | YP-146 | 406 ([M + H]$^+$, 70) |
| YP-147 | 383 ([M + H]$^+$, 5) | YP-148 | 418 ([M + H]$^+$, 70) |
| YP-149 | 428 ([M + H]$^+$, 50) | YP-150 | 428 ([M + H]$^+$, 70) |
| YP-151 | 428 ([M + H]$^+$, 60) | YP-152 | 394 ([M + H]$^+$, 100) |
| YP-153 | 348 ([M + H]$^+$, 80) | YP-154 | 361 ([M + H]$^+$, 60) |
| YP-155 | 376 ([M + H]$^+$, 70) | YP-156 | 404 ([M + H]$^+$, 80) |
| YP-157 | 390 ([M + H]$^+$, 100) | YP-158 | 378 ([M + H]$^+$, 70) |
| YP-159 | 416 ([M + H]$^+$, 100) | YP-160 | 416 ([M + H]$^+$, 80) |
| YP-161 | 366 ([M + H]$^+$, 100) | YP-162 | 366 ([M + H]$^+$, 70) |
| YP-163 | 382 ([M + H]$^+$, 10) | YP-164 | 382 ([M + H]$^+$, 30) |
| YP-165 | 417 ([M + H]$^+$, 90) | YP-166 | 427 ([M + H]$^+$, 5) |
| YP-167 | 427 ([M + H]$^+$, 80) | YP-168 | 427 ([M + H]$^+$, 75) |
| YP-169 | 427 ([M]$^+$, 90) | YP-170 | 427 ([M]$^+$, 50) |
| YP-171 | 393 ([M]$^+$, 60) | YP-172 | 348 ([M + 1]$^+$, 60) |
| YP-173 | 361 ([M]$^+$, 60) | YP-174 | 375 ([M]$^+$, 70) |
| YP-175 | 403 ([M]$^+$, 60) | YP-176 | 389 ([M]$^+$, 100) |
| YP-177 | 377 ([M]$^+$, 100) | YP-178 | 377 ([M]$^+$, 100) |
| YP-179 | 377 ([M]$^+$, 100) | YP-180 | 415 ([M]$^+$, 100) |
| YP-181 | 415 ([M]$^+$, 70) | YP-182 | 365 ([M]$^+$, 70) |
| YP-183 | 365 ([M]$^+$, 50) | YP-184 | 381 ([M]$^+$, 20) |
| YP-185 | 381 ([M]$^+$, 100) | YP-186 | 416 ([M]$^+$, 100) |
| YP-187 | 427 ([M + 1]$^+$, 100) | YP-188 | 426 ([M]$^+$, 100) |
| YP-189 | 426 ([M]$^+$, 100) | YP-190 | 393 ([M + 1]$^+$, 100) |
| YP-191 | 363 ([M + 1]$^+$, 80) | YP-192 | 376 ([M + 1]$^+$, 90) |
| YP-193 | 389 ([M]$^+$, 100) | YP-194 | 417 ([M]$^+$, 100) |
| YP-195 | 404 ([M + 1]$^+$, 100) | YP-196 | 391 ([M]$^+$, 80) |
| YP-197 | 391 ([M]$^+$, 100) | YP-198 | 391 ([M]$^+$, 100) |
| YP-199 | 430 ([M + 1]$^+$, 100) | YP-200 | 429 ([M]$^+$, 70) |
| YP-201 | 379 ([M]$^+$, 100) | YP-202 | 379 ([M]$^+$, 100) |
| YP-203 | 395 ([M]$^+$, 100) | YP-204 | 395 ([M]$^+$, 100) |
| YP-205 | 430 ([M]$^+$, 100) | YP-206 | 440 ([M]$^+$, 100) |
| YP-207 | 440 ([M]$^+$, 100) | YP-208 | 440 ([M]$^+$, 100) |
| YP-209 | 406 ([M]$^+$, 100) | YP-210 | 371 ([M]$^+$, 100) |
| YP-211 | 385 ([M]$^+$, 100) | YP-212 | 400 ([M + 1]$^+$, 90) |
| YP-213 | 427 ([M]$^+$, 100) | YP-214 | 414 ([M + 1]$^+$, 90) |
| YP-215 | 401 ([M]$^+$, 100) | YP-216 | 401 ([M]$^+$, 100) |
| YP-217 | 401 ([M]$^+$, 100) | YP-218 | 439 ([M]$^+$, 100) |
| YP-219 | 439 ([M]$^+$, 100) | YP-220 | 389 ([M]$^+$, 70) |
| YP-221 | 389 ([M]$^+$, 90) | YP-222 | 405 ([M]$^+$, 90) |
| YP-223 | 405 ([M]$^+$, 100) | YP-224 | 440 ([M]$^+$, 60) |
| YP-225 | 450 ([M]$^+$, 60) | YP-226 | 450 ([M]$^+$, 100) |
| YP-227 | 450 ([M]$^+$, 100) | YP-228 | 417 ([M + 1]$^+$, 100) |

TABLE 2

$^1$H NMR data of compounds in Table 1

| No. | $^1$H NMR (400 MHz, DMSO-d$_6$) |
|---|---|
| YP-1 | 5.60 (s, 2H, isoxazole-CH$_2$), 7.26 (s, 1H, H of isoxazole), 7.52-7.54 (m, 3H), 7.59 (dd, 1H, J = 8.8, 4.8 Hz), 7.89-7.92 (m, 2H), 8.17-8.20 (m, 1H), 8.83 (dd, 1H, J = 1.6, 1.6 Hz), 8.97 (d, 1H, J = 2.0 Hz). |
| YP-2 | 2.42 (s, 3H, CH$_3$), 5.60 (s, 2H, isoxazole-CH$_2$), 7.26 (s, 1H, H of isoxazole), 7.28 (2H, d, J = 4.8 Hz), 7.59 (dd, 1H, J = 8.8, 4.8 Hz), 7.74 (2H, d, J = 8.0 Hz), 8.17-8.20 (m, 1H), 8.83 (dd, 1H, J = 1.6, 1.6 Hz), 8.97 (d, 1H, J = 2.0 Hz). |
| YP-3 | 1.29 (t, 3H, CH$_3$, J = 7.6 Hz), 2.72 (q, 2H, CH$_2$, J = 7.6 Hz), 5.40 (s, 2H, CH$_2$ of isoxazole-CH$_2$), 7.26 (s, 1H, H of isoxazole), 7.32 (d, 2H, J = 8.0 Hz), 7.59 (dd, 1H, J = 8.8, |

TABLE 2-continued

¹H NMR data of compounds in Table 1

| No. | ¹H NMR (400 MHz, DMSO-d₆) |
|---|---|
|  | 4.8 Hz), 7.74 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-4 | 1.35 (s, 9H, 3CH₃), 5.37 (s, 2H, isoxazole-CH₂), 7.26 (s, 1H, H of isoxazole), 7.48 (d, 2H, J = 8.4 Hz), 7.59 (dd, 1H, J = 8.8, 4.8 Hz), 7.76 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-5 | 2.15 (s, 6H, 2CH₃), 2.31 (s, 3H, CH₃), 5.40 (s, 2H, isoxazole-CH₂), 6.33 (s, 1H, H of isoxazole), 6.93 (s, 2H), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-6 | 3.88 (s, 3H, OCH₃), 5.39 (s, 2H, CH₂ of isoxazole-CH₂), 6.67 (s, 1H, 1H of isoxazole), 7.00 (d, 2H, J = 5.2 Hz), 7.59 (dd, 1H, J = 8.8, 4.8 Hz), 7.79 (d, 2H, J = 9.2 Hz), 8.17-8.20 (m, 1H), 8.83 (dd, 1H, J = 1.6, 1.6 Hz), 8.97 (d, 1H, J = 2.0 Hz). |
| YP-7 | 3.92 (s, 3H, OCH₃), 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-8 | 3.89 (s, 3H, OCH₃), 5.40 (s, 2H, CH₂ of isoxazole-CH₂), 6.71 (s, 1H, H of isoxazole), 7.00-7.04 (m, 1H), 7.38-7.41 (m, 3H), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-9 | 5.42 (s, 2H, CH₂ of isoxazole-CH₂), 6.71 (s, 1H, 1H of isoxazole), 7.00-7.04 (m, 1H), 7.76 (d, 2H, J = 8.4 Hz), 7.98 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-10 | 5.42 (s, 2H, CH₂ of isoxazole-CH₂), 6.87 (s, 1H, 1H of isoxazole), 7.18-7.26 (m, 2H), 7.42-7.46 (m, 1H), 7.43-7.49 (m, 1H), 7.99-8.04 (m, 1H), 8.17-8.20 (m, 1H), 8.83 (dd, 1H, J = 1.6, 1.6 Hz), 8.97 (d, 1H, J = 2.0 Hz). |
| YP-11 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.85 (d, 2H, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-12 | 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.91 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-13 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.85 (d, 2H, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-14 | 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-15 | 5.42 (s, 2H, CH₂ of isoxazole-CH₂), 6.89 (s, 1H, 1H of isoxazole), 7.37 (dd, 1H, J = 2.0, 2.0 Hz), 7.42-7.46 (m, 1H), 7.54 (d, 1H, J = 2.0 Hz), 7.73 (d, 1H, J = 8.4 Hz), 8.17-8.20 (m, 1H), 8.83 (dd, 1H, J = 1.6, 1.6 Hz), 8.97 (d, 1H, J = 2.0 Hz). |
| YP-16 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.85 (d, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-17 | 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-18 | 5.40 (s, 2H, CH₂ of isoxazole-CH₂), 6.71 (s, 1H, 1H of isoxazole), 7.00-7.04 (m, 1H), 7.38-7.41 (m, 3H), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-19 | 5.43 (s, 2H, CH₂ of isoxazole-CH₂), 6.80 (s, 1H, 1H of isoxazole), 8.04 (d, 2H, J = 8.8 Hz), 7.59 (dd, 1H, J = 8.8, 4.8 Hz), 7.79 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-20 | 5.60 (s, 2H, isoxazole-CH₂), 7.26 (s, 1H, H of isoxazole), 7.52-7.54 (m, 3H), 7.59-7.63 (m, 1H), 7.89-7.92 (m, 2H), 8.37 (dd, J = 1.6, 1.6 Hz, 1H), 8.64 (dd, J = 1.6, 1.6 Hz, 1H). |
| YP-21 | 2.37 (s, 3H, CH₃), 5.60 (s, 2H, isoxazole-CH₂), 7.21 (s, 1H, H of isoxazole), 7.35 (d, J = 8.0 Hz, 2H), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-22 | 1.29 (t, 3H, CH₃, J = 7.6 Hz), 2.72 (q, 2H, CH₂, J = 7.6 Hz), 5.60 (s, 2H, CH₂ of isoxazole-CH₂), 7.21 (s, 1H, H of isoxazole), 7.35 (d, J = 8.0 Hz, 2H), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-23 | 1.35 (s, 9H, 3CH₃), 5.37 (s, 2H, CH₂ of isoxazole-CH₂), 7.26 (s, 1H, H of isoxazole), 7.35 (d, J = 8.0 Hz, 2H), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-24 | 2.15 (s, 6H, 2CH₃), 2.31 (s, 3H, CH₃), 5.40 (s, 2H, isoxazole-CH₂), 6.33 (s, 1H, H of isoxazole), 6.93 (s, 2H), 7.59-7.63 (m, 1H), 8.37 (dd, J = 1.6, 2.0 Hz, 1H), 8.65 (dd, J = 2.0, 2.0 Hz, 1H). |
| YP-25 | 3.83 (s, 3H, OCH₃), 5.58 (s, 2H, isoxazole-CH₂), 7.08 (d, J = 8.8 Hz, 2H), 7.18 (s, 1H, H of isoxazole), 7.59-7.62 (m, 1H), 7.84 (d, J = 8.8 Hz, 2H), 8.36 (dd, J = 2.0, 2.0 Hz, 1H), 8.64 (dd, J = 2.0, 2.0 Hz, 1H). |
| YP-26 | 3.83 (s, 3H, OCH₃), 5.58 (s, 2H, isoxazole-CH₂), 7.18 (s, 1H, H of isoxazole), 7.01-7.08 (m, 2H), 7.59-7.62 (m, 1H), 7.91 (dd, 1H, J = 1.6, 2.0 Hz), 8.36 (dd, J = 2.0, 2.0 Hz, 1H), 8.64 (dd, J = 2.0, 2.0 Hz, 1H). |
| YP-27 | 3.89 (s, 3H, OCH₃), 5.40 (s, 2H, CH₂ of isoxazole-CH₂), 6.71 (s, 1H, H of isoxazole), 7.38-7.41 (m, 3H), 7.59 (dd, 1H, J = 8.8, 4.8 Hz), 7.84 (d, J = 8.8 Hz, 2H), 8.36 (dd, J = 2.0, 2.0 Hz, 1H), 8.64 (dd, J = 2.0, 2.0 Hz, 1H). |

TABLE 2-continued

¹H NMR data of compounds in Table 1

| No. | ¹H NMR (400 MHz, DMSO-d₆) |
|---|---|
| YP-28 | 5.42 (s, 2H, CH₂ of isoxazole-CH₂), 6.71 (s, 1H, 1H of isoxazole), 7.76 (d, 2H, J = 8.4 Hz), 7.84 (d, J = 8.8 Hz, 2H), 7.98 (d, 2H, J = 8.4 Hz), 8.36 (dd, J = 2.0, 2.0 Hz, 1H), 8.64 (dd, J = 2.0, 2.0 Hz, 1H). |
| YP-29 | 5.42 (s, 2H, CH₂ of isoxazole-CH₂), 6.87 (s, 1H, 1H of isoxazole), 7.18-7.26 (m, 2H), 7.43-7.49 (m, 1H), 7.84 (d, J = 8.8 Hz, 2H), 8.36 (dd, J = 2.0, 2.0 Hz, 1H), 8.64 (dd, J = 2.0, 2.0 Hz, 1H). |
| YP-30 | 5.40 (s, 2H, CH₂ of isoxazole-CH₂), 6.69 (s, 1H, 1H of isoxazole), 7.20 (d, 2H, J = 8.8 Hz), 7.84 (d, J = 8.8 Hz, 2H), 7.85 (d, 2H, 2H, J = 8.8 Hz), 8.36 (dd, J = 2.0, 2.0 Hz, 1H), 8.64 (dd, J = 2.0, 2.0 Hz, 1H). |
| YP-31 | 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.8 Hz), 7.85 (d, 2H, 2H, J = 8.8 Hz), 8.36 (dd, J = 2.0, 2.0 Hz, 1H), 8.64 (dd, J = 2.0, 2.0 Hz, 1H). |
| YP-32 | 5.60 (s, 2H, isoxazole-CH₂), 7.29 (s, 1H, H of isoxazole), 7.59-7.62 (m, 3H), 7.94 (d, J = 8.8 Hz, 2H), 8.37 (dd, J = 1.6, 2.0 Hz, 1H), 8.64 (dd, J = 2.0, 2.0 Hz, 1H). |
| YP-33 | 5.63 (s, 2H, isoxazole-CH₂), 7.13 (s, 1H, H of isoxazole), 7.48-7.67 (m, 4H), 7.73 (dd, J = 2.0, 1.6 Hz, 1H), 8.37 (dd, J = 1.6, 2.0 Hz, 1H), 8.63-8.64 (m, 1H). |
| YP-34 | 5.63 (s, 2H, isoxazole-CH₂), 7.16 (s, 1H, H of isoxazole), 7.57-7.62 (m, 2H), 7.77 (d, J = 8.4 Hz, 1H), 7.86 (d, J = 2.0 Hz, 1H), 8.36 (dd, J = 2.0, 2.0 Hz, 1H), 8.64 (dd, J = 2.0, 2.0 Hz, 1H). |
| YP-35 | 5.60 (s, 2H, isoxazole-CH₂), 7.29 (s, 1H, H of isoxazole), 7.61 (dd, J = 4.8, 4.8 Hz, 1H), 7.76 (d, J = 8.4 Hz, 2H), 7.87 (d, J = 8.8 Hz, 2H), 8.37 (dd, J = 2.0, 1.6 Hz, 1H), 8.64 (dd, J = 1.6, 1.6 Hz, 1H). |
| YP-36 | 5.63 (s, 2H, isoxazole-CH₂), 7.13 (s, 1H, H of isoxazole), 7.48-7.67 (m, 4H), 7.73 (dd, J = 2.0, 1.6 Hz, 1H), 8.37 (dd, J = 1.6, 2.0 Hz, 1H), 8.63-8.64 (m, 1H). |
| YP-37 | 5.40 (s, 2H, CH₂ of isoxazole-CH₂), 6.71 (s, 1H, H of isoxazole), 7.38-7.41 (m, 3H), 7.59 (dd, 1H, J = 8.8, 4.8 Hz), 7.84 (d, J = 8.8 Hz, 2H), 8.3 (dd, J = 2.0, 2.0 Hz, 1H), 8.64 (dd, J = 2.0, 2.0 Hz, 1H). |
| YP-38 | 5.60 (s, 2H, isoxazole-CH₂), 7.29 (s, 1H, H of isoxazole), 7.61 (dd, J = 4.8, 4.8 Hz, 1H), 7.76 (d, J = 8.4 Hz, 2H), 7.87 (d, J = 8.8 Hz, 2H), 8.37 (dd, J = 2.0, 1.6 Hz, 1H), 8.64 (dd, J = 1.6, 1.6 Hz, 1H). |
| YP-39 | 5.60 (s, 2H, isoxazole-CH₂), 7.27 (s, 1H, H of isoxazole), 7.52-7.55 (m, 3H), 7.89-7.91 (m, 2H), 8.47 (d, J = 2.8 Hz, 1H), 8.75 (d, J = 2.8 Hz, 1H). |
| YP-40 | 2.37 (s, 3H, CH₃), 5.59 (s, 2H, isoxazole-CH₂), 7.22 (s, 1H, H of isoxazole), 7.35 (d, J = 8.0 Hz, 2H), 7.79 (d, J = 8.0 Hz, 2H), 8.46 (d, J = 2.8 Hz, 1H), 8.74 (d, J = 2.4 Hz, 1H). |
| YP-41 | 1.29 (t, 3H, CH₃, J = 7.6 Hz), 2.72 (q, 2H, CH₂, J = 7.6 Hz), 7.22 (s, 1H, H of isoxazole), 7.35 (d, J = 8.0 Hz, 2H), 7.79 (d, J = 8.0 Hz, 2H), 8.46 (d, J = 2.8 Hz, 1H), 8.74 (d, J = 2.4 Hz, 1H). |
| YP-42 | 1.35 (s, 9H, 3CH₃), 7.22 (s, 1H, H of isoxazole), 7.35 (d, J = 8.0 Hz, 2H), 7.79 (d, J = 8.0 Hz, 2H), 8.46 (d, J = 2.8 Hz, 1H), 8.74 (d, J = 2.4 Hz, 1H). |
| YP-43 | 2.15 (s, 6H, 2CH₃), 2.31 (s, 3H, CH₃), 7.22 (s, 1H, H of isoxazole), 7.35 (d, J = 8.0 Hz, 2H), 7.79 (d, J = 8.0 Hz, 2H), 8.46 (d, J = 2.8 Hz, 1H), 8.74 (d, J = 2.4 Hz, 1H). |
| YP-44 | 3.82 (s, 3H, OCH₃), 5.57 (s, 2H, isoxazole-CH₂), 7.08 (d, J = 9.2 Hz, 2H), 7.20 (s, 1H, H of isoxazole), 7.84 (d, J = 8.8 Hz, 2H), 8.46 (d, J = 2.4 Hz, 1H), 8.75 (d, J = 2.4 Hz, 1H). |
| YP-45 | 3.82 (s, 3H, OCH₃), 5.57 (s, 2H, isoxazole-CH2), 7.01-7.08 (m, 2H), 7.42-7.46 (m, 1H), 7.59 (dd, 1H, J = 8.8, 4.8 Hz), 8.46 (d, J = 2.4 Hz, 1H), 8.75 (d, J = 2.4 Hz, 1H). |
| YP-46 | 3.89 (s, 3H, OCH₃), 5.40 (s, 2H, CH₂ of isoxazole-CH₂), 6.71 (s, 1H, H of isoxazole), 7.00-7.04 (m, 1H), 7.38-7.41 (m, 3H), 8.46 (d, J = 2.4 Hz, 1H), 8.75 (d, J = 2.4 Hz, 1H). |
| YP-47 | 5.42 (s, 2H, CH₂ of isoxazole-CH₂), 6.71 (s, 1H, 1H of isoxazole), 7.76 (d, 2H, J = 8.4 Hz), 7.98 (d, 2H, J = 8.4 Hz), 8.46 (d, J = 2.4 Hz, 1H), 8.75 (d, J = 2.4 Hz, 1H). |
| YP-48 | 5.42 (s, 2H, CH₂ of isoxazole-CH₂), 6.87 (s, 1H, 1H of isoxazole), 7.18-7.26 (m, 2H), 7.42-7.46 (m, 1H), 7.43-7.49 (m, 1H), 8.46 (d, J = 2.4 Hz, 1H), 8.75 (d, J = 2.4 Hz, 1H). |
| YP-49 | 5.60 (s, 2H, isoxazole-CH₂), 7.30 (s, 1H, H of isoxazole), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-50 | 5.63 (s, 2H, isoxazole-CH₂), 7.15 (s, 1H, H of isoxazole), 7.48-7.52 (m, 1H), 7.54-7.58 (m, 1H), 7.67 (dd, J = 1.2, 1.2 Hz, 1H), 7.72 (dd, J = 1.6, 2.0 Hz, 1H), 8.46 (d, J = 2.8 Hz, 1H), 8.75 (d, J = 2.4 Hz, 1H). |
| YP-51 | 5.60 (s, 2H, isoxazole-CH₂), 7.30 (s, 1H, H of isoxazole), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-52 | 5.63 (s, 2H, isoxazole-CH₂), 7.15 (s, 1H, H of isoxazole), 7.48-7.52 (m, 1H), 7.54-7.58 (m, 1H), 7.67 (dd, J = 1.2, 1.2 Hz, 1H), 7.72 (dd, J = 1.6, 2.0 Hz, 1H), 8.46 (d, J = 2.8 Hz, 1H), 8.75 (d, J = 2.4 Hz, 1H). |
| YP-53 | 5.60 (s, 2H, isoxazole-CH₂), 7.30 (s, 1H, H of isoxazole), 7.75 (d, J = 8.4 Hz, 2H), 7.87 (d, J = 8.8 Hz, 2H), 8.47 (d, J = 2.8 Hz, 1H), 8.75 (d, J = 2.4 Hz, 1H). |
| YP-54 | 5.60 (s, 2H, isoxazole-CH₂), 7.30 (s, 1H, H of isoxazole), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-55 | 5.63 (s, 2H, isoxazole-CH₂), 7.15 (s, 1H, H of isoxazole), 7.48-7.52 (m, 1H), 7.54-7.58 (m, 1H), 7.67 (dd, J = 1.2, 1.2 Hz, 1H), 7.72 (dd, J = 1.6, 2.0 Hz, 1H), 8.46 (d, J = 2.8 Hz, 1H), 8.75 (d, J = 2.4 Hz, 1H). |
| YP-56 | 5.40 (s, 2H, CH₂ of isoxazole-CH₂), 6.71 (s, 1H, 1H of isoxazole), 7.00-7.04 (m, 1H), 7.38-7.41 (m, 3H), 8.46 (d, J = 2.8 Hz, 1H), 8.75 (d, J = 2.4 Hz, 1H). |
| YP-57 | 5.60 (s, 2H, isoxazole-CH₂), 7.30 (s, 1H, H of isoxazole), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-58 | 5.65 (s, 2H, isoxazole-CH₂), 7.32 (s, 1H, H of isoxazole), 7.51-7.55 (m, 3H), 7.89-7.92 (m, 2H), 8.12 (d, J = 8.0 Hz, 1H), 8.65 (dd, J = 1.6, 1.6 Hz, 1H), 9.33 (d, J = 1.6 Hz, 1H). |

TABLE 2-continued

¹H NMR data of compounds in Table 1

| No. | ¹H NMR (400 MHz, DMSO-d₆) |
|---|---|
| YP-59 | 2.37 (s, 3H, CH₃), 5.63 (s, 2H, isoxazole-CH₂), 7.25 (s, 1H, H of isoxazole), 7.35 (d, J = 8.0 Hz, 2H), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-60 | 1.29 (t, 3H, CH₃, J = 7.6 Hz), 2.72 (q, 2H, CH₂, J = 7.6 Hz), 5.63 (s, 2H, isoxazole-CH₂), 7.25 (s, 1H, H of isoxazole), 7.35 (d, J = 8.0 Hz, 2H), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-61 | 1.35 (s, 9H, 3CH₃), 5.63 (s, 2H, isoxazole-CH₂), 7.25 (s, 1H, H of isoxazole), 7.35 (d, J = 8.0 Hz, 2H), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-62 | 2.15 (s, 6H, 2CH₃), 2.31 (s, 3H, CH₃), 5.63 (s, 2H, isoxazole-CH₂), 7.25 (s, 1H, H of isoxazole), 7.35 (d, J = 8.0 Hz, 2H), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-63 | 2.91 (s, 3H, CH₃), 5.62 (s, 2H, isoxazole-CH₂), 7.08 (d, J = 8.0 Hz, 2H), 7.23 (s, 1H, H of isoxazole), 7.84 (d, J = 6.8 Hz, 2H), 8.12 (d, J = 8.0 Hz, 1H), 8.63 (t, J = 8.4 Hz, 1H), 9.32 (d, J = 1.2 Hz, 1H). |
| YP-64 | 3.92 (s, 3H, OCH₃), 5.62 (s, 2H, isoxazole-CH₂), 7.23 (s, 1H, H of isoxazole), 7.01-7.08 (m, 2H), 7.42-7.46 (m, 1H), 7.59 (dd, 1H, J = 8.8, 4.8 Hz), 8.12 (d, J = 8.0 Hz, 1H), 8.63 (t, J = 8.4 Hz, 1H), 9.32 (d, J = 1.2 Hz, 1H). |
| YP-65 | 3.92 (s, 3H, OCH₃), 5.62 (s, 2H, isoxazole-CH₂), 7.23 (s, 1H, H of isoxazole), 7.00-7.04 (m, 1H), 7.38-7.41 (m, 3H), 8.12 (d, J = 8.0 Hz, 1H), 8.63 (t, J = 8.4 Hz, 1H), 9.32 (d, J = 1.2 Hz, 1H). |
| YP-66 | 5.42 (s, 2H, CH₂ of isoxazole-CH₂), 6.71 (s, 1H, 1H of isoxazole), 7.76 (d, 2H, J = 8.4 Hz), 7.98 (d, 2H, J = 8.4 Hz), 8.12 (d, J = 8.0 Hz, 1H), 8.63 (t, J = 8.4 Hz, 1H), 9.32 (d, J = 1.2 Hz, 1H). |
| YP-67 | 5.42 (s, 2H, CH₂ of isoxazole-CH2), 6.87 (s, 1H, 1H of isoxazole), 7.18-7.26 (m, 2H), 7.42-7.46 (m, 1H), 7.43-7.49 (m, 1H), 8.12 (d, J = 8.0 Hz, 1H), 8.63 (t, J = 8.4 Hz, 1H), 9.32 (d, J = 1.2 Hz, 1H). |
| YP-68 | 5.40 (s, 2H, CH₂ of isoxazole-CH₂), 6.69 (s, 1H, 1H of isoxazole), 7.20 (d, 2H, 2H, J = 8.8 Hz), 7.85 (d, 2H, 2H, J = 8.8 Hz), 8.12 (d, J = 8.0 Hz, 1H), 8.63 (t, J = 8.4 Hz, 1H), 9.32 (d, J = 1.2 Hz, 1H). |
| YP-69 | 5.41 (s, 2H, CH₂ of isoxazole-CH₂), 6.92 (s, 1H, 1H of isoxazole), 7.01-7.08 (m, 2H), 7.42-7.46 (m, 1H), 7.59 (dd, 1H, J = 8.8, 4.8 Hz), 8.12 (d, J = 8.0 Hz, 1H), 8.63 (t, J = 8.4 Hz, 1H), 9.32 (d, J = 1.2 Hz, 1H). |
| YP-70 | 5.65 (s, 2H, isoxazole-CH₂), 7.34 (s, 1H, H of isoxazole), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-71 | 5.68 (s, 2H, isoxazole-CH₂), 7.18 (s, 1H, H of isoxazole), 7.48-7.52 (m, 1H), 7.54-7.59 (m, 2H), 7.68 (dd, J = 1.6, 0.8 Hz, 1H), 7.30 (dd, J = 1.6, 2.0 Hz, 1H), 8.11 (d, J = 8.0 Hz, 1H), 8.63 (dt, J = 2.4, 0.4 Hz, 1H), 9.31 (d, J = 2.0 Hz, 1H). |
| YP-72 | 5.65 (s, 2H, isoxazole-CH₂), 7.33 (s, 1H, H of isoxazole), 7.75 (d, J = 8.8 Hz, 2H), 7.87 (d, J = 8.4 Hz, 2H), 8.12 (d, J = 8.0 Hz, 2H), 8.65 (dd, J = 1.6, 1.6 Hz, 1H), 9.32 (d, J = 1.6 Hz, 1H). |
| YP-73 | 5.65 (s, 2H, isoxazole-CH₂), 7.34 (s, 1H, H of isoxazole), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-74 | 5.68 (s, 2H, isoxazole-CH₂), 7.18 (s, 1H, H of isoxazole), 7.48-7.52 (m, 1H), 7.54-7.59 (m, 2H), 7.68 (dd, J = 1.6, 0.8 Hz, 1H), 7.30 (dd, J = 1.6, 2.0 Hz, 1H), 8.11 (d, J = 8.0 Hz, 1H), 8.63 (dt, J = 2.4, 0.4 Hz, 1H), 9.31 (d, J = 2.0 Hz, 1H). |
| YP-75 | 5.62 (s, 2H, isoxazole-CH₂), 7.23 (s, 1H, H of isoxazole), 7.00-7.04 (m, 1H), 7.38-7.41 (m, 3H), 8.12 (d, J = 8.0 Hz, 1H), 8.63 (t, J = 8.4 Hz, 1H), 9.32 (d, J = 1.2 Hz, 1H). |
| YP-76 | 5.65 (s, 2H, isoxazole-CH₂), 7.34 (s, 1H, H of isoxazole), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-77 | 2.81 (s, 3H, CH₃), 5.61 (s, 2H, isoxazole-CH₂), 7.28 (s, 1H, H of isoxazole), 7.52-7.55 (m, 3H), 7.90-7.92 (m, 3H), 8.53 (d, J = 8.0 Hz, 1H). |
| YP-78 | 2.42 (s, 3H, CH₃), 2.86 (s, 3H, CH₃), 5.64 (s, 2H, isoxazole-CH₂), 7.27 (s, 1H, H of isoxazole), 7.39 (d, J = 8.0 Hz, 2H), 7.85 (d, J = 8.0 Hz, 2H), 7.86 (d, J = 8.0 Hz, 1H), 8.57 (d, J = 8.0 Hz, 1H) |
| YP-79 | 1.29 (t, 3H, CH₃, J = 7.6 Hz), 2.72 (q, 2H, CH₂, J = 7.6 Hz), 2.86 (s, 3H, CH₃), 5.64 (s, 2H, isoxazole-CH₂), 7.27 (s, 1H, H of isoxazole), 7.39 (d, J = 8.0 Hz, 2H), 7.85 (d, J = 8.0 Hz, 2H), 7.86 (d, J = 8.0 Hz, 1H), 8.57 (d, J = 8.0 Hz, 1H). |
| YP-80 | 1.35 (s, 9H, 3CH₃), 2.86 (s, 3H, CH₃), 5.64 (s, 2H, isoxazole-CH₂), 7.27 (s, 1H, H of isoxazole), 7.39 (d, J = 8.0 Hz, 2H), 7.85 (d, J = 8.0 Hz, 2H), 7.86 (d, J = 8.0 Hz, 1H), 8.57 (d, J = 8.0 Hz, 1H). |
| YP-81 | 2.15 (s, 6H, 2CH₃), 2.31 (s, 3H, CH₃), 2.86 (s, 3H, CH₃), 5.40 (s, 2H, isoxazole-CH₂), 6.33 (s, 1H, H of isoxazole), 6.93 (s, 2H), 7.86 (d, J = 8.0 Hz, 1H), 8.57 (d, J = 8.0 Hz, 1H). |
| YP-82 | 2.80 (s, 3H, CH₃), 3.82 (s, 3H, OCH₃), 5.58 (s, 2H, isoxazole-CH₂), 7.08 (d, J = 8.8 Hz, 2H), 7.19 (s, 1H, H of isoxazole), 7.85 (d, J = 8.8 Hz, 2H), 7.91 (d, J = 8.4 Hz, 1H), 8.52 (d, J = 8.4 Hz, 1H). |
| YP-83 | 2.80 (s, 3H, CH₃), 3.82 (s, 3H, OCH₃), 5.58 (s, 2H, isoxazole-CH₂), 7.01-7.08 (m, 2H), 7.19 (s, 1H, H of isoxazole), 7.42-7.46 (m, 1H), 7.59 (dd, 1H, J = 8.8, 4.8 Hz), 7.91 (d, J = 8.4 Hz, 1H), 8.52 (d, J = 8.4 Hz, 1H). |
| YP-84 | 2.80 (s, 3H, CH₃), 3.82 (s, 3H, OCH₃), 5.58 (s, 2H, isoxazole-CH₂), 6.71 (s, 1H, H of isoxazole), 7.38-7.41 (m, 3H), 7.59 (dd, 1H, J = 8.8, 4.8 Hz), 7.91 (d, J = 8.4 Hz, 1H), 8.52 (d, J = 8.4 Hz, 1H). |

TABLE 2-continued

¹H NMR data of compounds in Table 1

| No. | ¹H NMR (400 MHz, DMSO-d₆) |
|---|---|
| YP-85 | 2.80 (s, 3H, CH₃), 5.42 (s, 2H, CH₂ of isoxazole-CH₂), 6.71 (s, 1H, 1H of isoxazole), 7.76 (d, 2H, J = 8.4 Hz), 7.98 (d, 2H, J = 8.4 Hz), 7.91 (d, J = 8.4 Hz, 1H), 8.52 (d, J = 8.4 Hz, 1H). |
| YP-86 | 2.80 (s, 3H, CH₃), 5.42 (s, 2H, CH₂ of isoxazole-CH₂), 6.87 (s, 1H, 1H of isoxazole), 7.18-7.26 (m, 2H), 7.43-7.49 (m, 1H), 7.91 (d, J = 8.4 Hz, 1H), 7.99-8.04 (m, 1H), 8.52 (d, J = 8.4 Hz, 1H). |
| YP-87 | 2.80 (s, 3H, CH₃), 5.61 (s, 2H, isoxazole-CH₂), 7.29 (s, 1H, H of isoxazole), 7.59-7.62 (m, 2H), 7.89-7.95 (m, 3H), 8.52 (d, J = 8.0 Hz, 1H). |
| YP-88 | 2.81 (s, 3H, CH₃), 5.64 (s, 2H, isoxazole-CH₂), 7.15 (s, 1H, H of isoxazole), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-89 | 2.80 (s, 3H, CH₃), 5.61 (s, 2H, isoxazole-CH₂), 7.29 (s, 1H, H of isoxazole), 7.59-7.62 (m, 2H), 7.89-7.95 (m, 3H), 8.52 (d, J = 8.0 Hz, 1H). |
| YP-90 | 2.81 (s, 3H, CH₃), 5.64 (s, 2H, isoxazole-CH₂), 7.15 (s, 1H, H of isoxazole), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-91 | 2.81 (s, 3H, CH₃), 5.61 (s, 2H, isoxazole-CH₂), 7.30 (s, 1H, H of isoxazole), 7.74 (d, J = 6.8 Hz, 2H), 7.87 (d, J = 6.8 Hz, 2H), 7.91 (d, J = 8.4 Hz, 1H), 8.52 (d, J = 8.0 Hz, 1H). |
| YP-92 | 2.80 (s, 3H, CH₃), 5.61 (s, 2H, isoxazole-CH₂), 7.29 (s, 1H, H of isoxazole), 7.59-7.62 (m, 2H), 7.89-7.95 (m, 3H), 8.52 (d, J = 8.0 Hz, 1H). |
| YP-93 | 2.81 (s, 3H, CH₃), 5.64 (s, 2H, isoxazole-CH₂), 7.15 (s, 1H, H of isoxazole), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-94 | 2.81 (s, 3H, CH₃), 5.40 (s, 2H, CH₂ of isoxazole-CH₂), 6.71 (s, 1H, 1H of isoxazole), 7.00-7.04 (m, 1H), 7.38-7.41 (m, 3H), 7.91 (d, J = 8.0 Hz, 1H), 8.52 (d, J = 8.0 Hz, 1H). |
| YP-95 | 2.81 (s, 3H, CH₃), 5.43 (s, 2H, CH₂ of isoxazole-CH₂), 6.80 (s, 1H, 1H of isoxazole), 8.04 (d, 2H, J = 8.8 Hz), 7.79 (d, 2H, J = 8.4 Hz), 7.91 (d, J = 8.0 Hz, 1H), 8.52 (d, J = 8.0 Hz, 1H). |
| YP-96 | 5.56 (s, 2H, isoxazole-CH₂), 7.15-7.21 (m, 3H), 7.26 (s, 1H, H of isoxazole), 7.28-7.30 (m, 1H), 7.44-7.54 (m, 5H), 7.89-7.91 (m, 2H), 8.37 (dd, J = 2.4, 2.4 Hz, 1H), 8.80 (d, J = 2.4 Hz, 1H). |
| YP-97 | 2.36 (s, 3H, CH₃), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.79 (d, J = 8.0 Hz, 2H), 8.39 (dd, J = 2.4, 2.4 Hz, 1H), 8.79-8.80 (m, 1H). |
| YP-98 | 1.29 (t, 3H, CH₃, J = 7.6 Hz), 2.72 (q, 2H, CH₂, J = 7.6 Hz), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.79 (d, J = 8.0 Hz, 2H), 8.39 (dd, J = 2.4, 2.4 Hz, 1H), 8.79-8.80 (m, 1H). |
| YP-99 | 1.35 (s, 9H, 3CH₃), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.79 (d, J = 8.0 Hz, 2H), 8.39 (dd, J = 2.4, 2.4 Hz, 1H), 8.79-8.80 (m, 1H). |
| YP-100 | 2.15 (s, 6H, 2CH₃), 2.31 (s, 3H, CH₃), 5.54 (s, 2H, isoxazole-CH₂), 6.93 (s, 2H), 7.15-7.20 (m, 3H), 7.21 (s, 1H, H of isoxazole), 7.44-7.48 (m, 2H), 8.39 (dd, J = 2.4, 2.4 Hz, 1H), 8.79-8.80 (m, 1H). |
| YP-101 | 3.82 (s, 3H, OCH₃), 5.54 (s, 2H, isoxazole-CH₂), 7.05-7.07 (m, 2H), 7.14-7.21 (m, 3H), 7.22 (s, 1H, H of isoxazole), 7.26-7.30 (m, 1H), 7.44-7.48 (m, 2H), 7.82-7.84 (m, 2H), 8.38 (dd, J = 2.4, 2.4 Hz, 1H), 8.79 (d, J = 2.4 Hz, 1H). |
| YP-102 | 3.92 (s, 3H, OCH₃), 5.54 (s, 2H, isoxazole-CH₂), 7.01-7.08 (m, 2H), 7.05-7.07 (m, 2H), 7.14-7.21 (m, 3H), 7.22 (s, 1H, H of isoxazole), 7.42-7.46 (m, 1H), 7.59 (dd, 1H, J = 8.8, 4.8 Hz), 8.38 (dd, J = 2.4, 2.4 Hz, 1H), 8.79 (d, J = 2.4 Hz, 1H). |
| YP-103 | 3.89 (s, 3H, OCH₃), 5.40 (s, 2H, CH₂ of isoxazole-CH₂), 6.71 (s, 1H, H of isoxazole), 7.00-7.04 (m, 1H), 7.05-7.07 (m, 2H), 7.14-7.21 (m, 3H), 7.38-7.41 (m, 3H), 8.38 (dd, J = 2.4, 2.4 Hz, 1H), 8.79 (d, J = 2.4 Hz, 1H). |
| YP-104 | 5.54 (s, 2H, isoxazole-CH2), 7.21 (s, 1H, H of isoxazole), 7.28-7.34 (m, 3H), 7.44-7.48 (m, 2H), 7.76 (d, 2H, J = 8.4 Hz), 7.98 (d, 2H, J = 8.4 Hz), 8.39 (dd, J = 2.4, 2.4 Hz, 1H), 8.79-8.80 (m, 1H). |
| YP-105 | 5.54 (s, 2H, isoxazole-CH₂), 7.21 (s, 1H, H of isoxazole), 7.18-7.26 (m, 2H), 7.28-7.34 (m, 3H), 7.44-7.48 (m, 3H), 8.39 (dd, J = 2.4, 2.4 Hz, 1H), 7.99-8.04 (m, 1H), 8.79-8.80 (m, 1H). |
| YP-106 | 5.57 (s, 2H, isoxazole-CH₂), 7.15-7.28 (m, 4H), 7.29 (s, 1H, H of isoxazole), 7.46 (d, J = 8.0 Hz, 2H), 7.60 (d, J = 6.4 Hz, 2H), 7.92-7.94 (m, 2H), 8.37-8.39 (m, 1H), 8.79 (d, J = 2.4 Hz, 1H). |
| YP-107 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-108 | 5.57 (s, 2H, isoxazole-CH₂), 7.15-7.28 (m, 4H), 7.29 (s, 1H, H of isoxazole), 7.46 (d, J = 8.0 Hz, 2H), 7.60 (d, J = 6.4 Hz, 2H), 7.92-7.94 (m, 2H), 8.37-8.39 (m, 1H), 8.79 (d, J = 2.4 Hz, 1H). |
| YP-109 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-110 | 5.56 (s, 2H, isoxazole-CH₂), 7.15-7.20 (m, 2H), 7.21 (s, 1H, H of isoxazole), 7.26-7.29 (m, 2H), 7.44-7.48 (m, 2H), 7.72-7.75 (m, 2H), 7.85-7.87 (m, 2H), 8.38 (dd, J = 2.4, 2.4 Hz, 1H), 8.79 (d, J = 2.8 Hz, 1H). |

TABLE 2-continued

¹H NMR data of compounds in Table 1

| No. | ¹H NMR (400 MHz, DMSO-d₆) |
|---|---|
| YP-111 | 5.57 (s, 2H, isoxazole-CH₂), 7.15-7.28 (m, 4H), 7.29 (s, 1H, H of isoxazole), 7.46 (d, J = 8.0 Hz, 2H), 7.60 (d, J = 6.4 Hz, 2H), 7.92-7.94 (m, 2H), 8.37-8.39 (m, 1H), 8.79 (d, J = 2.4 Hz, 1H). |
| YP-112 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-113 | 5.40 (s, 2H, CH₂ of isoxazole-CH₂), 6.71 (s, 1H, H of isoxazole), 7.00-7.04 (m, 1H), 7.05-7.07 (m, 2H), 7.14-7.21 (m, 3H), 7.38-7.41 (m, 3H), 8.38 (dd, J = 2.4, 2.4 Hz, 1H), 8.79 (d, J = 2.4 Hz, 1H). |
| YP-114 | 5.57 (s, 2H, isoxazole-CH₂), 7.15-7.28 (m, 4H), 7.29 (s, 1H, H of isoxazole), 7.79 (d, 2H, J = 8.4 Hz), 7.92-7.94 (m, 2H), 8.04 (d, J = 6.4 Hz, 2H), 8.37-8.39 (m, 1H), 8.79 (d, J = 2.4 Hz, 1H). |
| YP-115 | 5.60 (s, 2H, isoxazole-CH₂), 7.26 (s, 1H, H of isoxazole), 7.48 (t, 1H, J = 4.8 Hz, NHC=O), 7.52-7.54 (m, 3H), 7.59 (dd, 1H, J = 8.8, 4.8 Hz), 7.89-7.92 (m, 2H), 8.17-8.20 (m, 1H), 8.83 (dd, 1H, J = 1.6, 1.6 Hz), 8.97 (d, 1H, J = 2.0 Hz). |
| YP-116 | 2.42 (s, 3H, CH₃), 5.60 (s, 2H, isoxazole-CH₂), 7.26 (s, 1H, H of isoxazole), 7.28 (2H, d, J = 4.8 Hz), 7.48 (t, 1H, J = 4.8 Hz, NHC=O), 7.59 (dd, 1H, J = 8.8, 4.8 Hz), 7.74 (2H, d, J = 8.0 Hz), 8.17-8.20 (m, 1H), 8.83 (dd, 1H, J = 1.6, 1.6 Hz), 8.97 (d, 1H, J = 2.0 Hz). |
| YP-117 | 1.29 (t, 3H, CH₃, J = 7.6 Hz), 2.72 (q, 2H, CH₂, J = 7.6 Hz), 5.40 (s, 2H, CH₂ of isoxazole-CH₂), 7.26 (s, 1H, H of isoxazole), 7.32 (d, 2H, J = 8.0 Hz), 7.48 (t, 1H, J = 4.8 Hz, NHC=O), 7.59 (dd, 1H, J = 8.8, 4.8 Hz), 7.74 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-118 | 1.35 (s, 9H, 3CH₃), 5.37 (s, 2H, isoxazole-CH₂), 7.26 (s, 1H, H of isoxazole), 7.48 (d, 2H, J = 8.4 Hz), 7.59 (dd, 1H, J = 8.8, 4.8 Hz), 7.76 (d, 2H, J = 8.4 Hz), 7.87 (t, 1H, J = 4.8 Hz, NHC=O), 8.17-8.20 (m, 1H), 8.83 (dd, 1H, J = 1.6, 1.6 Hz), 8.97 (d, 1H, J = 2.0 Hz). |
| YP-119 | 2.15 (s, 6H, 2CH₃), 2.31 (s, 3H, CH₃), 5.40 (s, 2H, isoxazole-CH₂), 6.33 (s, 1H, H of isoxazole), 6.93 (s, 2H), 7.48 (t, 1H, J = 4.8 Hz, NHC=O), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-120 | 3.88 (s, 3H, OCH₃), 5.39 (s, 2H, CH₂ of isoxazole-CH₂), 6.67 (s, 1H, 1H of isoxazole), 7.00 (d, 2H, J = 5.2 Hz), 7.48 (t, 1H, J = 4.8 Hz, NHC=O), 7.59 (dd, 1H, J = 8.8, 4.8 Hz), 7.79 (d, 2H, J = 9.2 Hz), 8.17-8.20 (m, 1H), 8.83 (dd, 1H, J = 1.6, 1.6 Hz), 8.97 (d, 1H, J = 2.0 Hz). |
| YP-121 | 3.92 (s, 3H, OCH₃), 5.41 (s, 2H, CH₂ of isoxazole-CH₂), 6.92 (s, 1H, 1H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-122 | 3.89 (s, 3H, OCH₃), 5.40 (s, 2H, CH₂ of isoxazole-CH₂), 6.71 (s, 1H, 1H of isoxazole), 7.00-7.04 (m, 1H), 7.38-7.41 (m, 3H), 7.48 (t, 1H, J = 4.8 Hz, NHC=O), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-123 | 5.42 (s, 2H, CH₂ of isoxazole-CH₂), 6.71 (s, 1H, 1H of isoxazole), 7.00-7.04 (m, 1H), 7.49 (t, 1H, J = 4.8 Hz, NHC=O), 7.76 (d, 2H, J = 8.4 Hz), 7.98 (d, 2H, J = 8.4 Hz), 8.17-8.20 (m, 1H), 8.83 (dd, 1H, J = 1.6, 1.6 Hz), 8.97 (d, 1H, J = 2.0 Hz). |
| YP-124 | 5.42 (s, 2H, CH₂ of isoxazole-CH₂), 6.87 (s, 1H, 1H of isoxazole), 7.18-7.26 (m, 2H), 7.42-7.46 (m, 1H), 7.43-7.49 (m, 1H), 7.53 (t, 1H, J = 4.8 Hz, NHC=O), 7.99-8.04 (m, 1H), 8.17-8.20 (m, 1H), 8.83 (dd, 1H, J = 1.6, 1.6 Hz), 8.97 (d, 1H, J = 2.0 Hz). |
| YP-125 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.48 (t, 1H, J = 4.8 Hz, NHC=O), 7.85 (d, 2H, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-126 | 5.41 (s, 2H, CH₂ of isoxazole-CH₂), 6.92 (s, 1H, 1H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-127 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.50 (t, 1H, J = 4.8 Hz, NHC=O), 7.85 (d, 2H, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-128 | 5.41 (s, 2H, CH₂ of isoxazole-CH₂), 6.92 (s, 1H, 1H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-129 | 5.42 (s, 2H, CH₂ of isoxazole-CH₂), 6.89 (s, 1H, 1H of isoxazole), 7.37 (dd, 1H, J = 2.0, 2.0 Hz), 7.42-7.46 (m, 1H), 7.48 (t, 1H, J = 4.8 Hz, NHC=O), 7.54 (d, 1H, J = 2.0 Hz), 7.73 (d, 1H, J = 8.4 Hz), 8.17-8.20 (m, 1H), 8.83 (dd, 1H, J = 1.6, 1.6 Hz), 8.97 (d, 1H, J = 2.0 Hz). |
| YP-130 | 5.40 (s, 2H, CH₂ of isoxazole-CH₂), 6.69 (s, 1H, 1H of isoxazole), 7.20 (d, 2H, 2H, J = 8.8 Hz), 7.42-7.46 (m, 1H), 7.48 (t, 1H, J = 4.8 Hz, NHC=O), 7.85 (d, 2H, 2H, J = 8.8 Hz), 8.17-8.20 (m, 1H), 8.83 (dd, 1H, J = 1.6, 1.6 Hz), 8.97 (d, 1H, J = 2.0 Hz). |
| YP-131 | 5.41 (s, 2H, CH₂ of isoxazole-CH₂), 6.92 (s, 1H, 1H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 7.79 (d, 2H, J = 9.2 Hz), 7.91 (dd, 1H, J = 1.6, 2.0 Hz), 8.17-8.20 (m, 1H), 8.83 (dd, 1H, J = 1.6, 1.6 Hz), 8.97 (d, 1H, J = 2.0 Hz). |
| YP-132 | 5.40 (s, 2H, CH₂ of isoxazole-CH₂), 6.71 (s, 1H, 1H of isoxazole), 7.00-7.04 (m, 1H), 7.38-7.41 (m, 3H), 7.48 (t, 1H, J = 4.8 Hz, NHC=O), 7.59 (dd, 1H, J = 8.8, 4.8 Hz), 8.17-8.20 (m, 1H), 8.83 (dd, 1H, J = 1.6, 1.6 Hz), 8.97 (d, 1H, J = 2.0 Hz). |
| YP-133 | 5.43 (s, 2H, CH₂ of isoxazole-CH₂), 6.80 (s, 1H, 1H of isoxazole), 7.48 (t, 1H, J = 4.8 Hz, NHC=O), 8.04 (d, 2H, J = 8.8 Hz), 7.59 (dd, 1H, J = 8.8, 4.8 Hz), 7.79 (d, 2H, J = 8.4 Hz), 8.17-8.20 (m, 1H), 8.83 (dd, 1H, J = 1.6, 1.6 Hz), 8.97 (d, 1H, J = 2.0 Hz). |

TABLE 2-continued

¹H NMR data of compounds in Table 1

| No. | ¹H NMR (400 MHz, DMSO-d₆) |
|---|---|
| YP-134 | 5.60 (s, 2H, isoxazole-CH₂), 7.26 (s, 1H, H of isoxazole), 7.55 (t, 1H, J = 4.8 Hz, NHC=O), 7.52-7.54 (m, 3H), 7.59-7.63 (m, 1H), 7.89-7.92 (m, 2H), 8.37 (dd, J = 1.6, 1.6 Hz, 1H), 8.64 (dd, J = 1.6, 1.6 Hz, 1H). |
| YP-135 | 2.37 (s, 3H, CH₃), 5.60 (s, 2H, isoxazole-CH₂), 7.21 (s, 1H, H of isoxazole), 7.35 (d, J = 8.0 Hz, 2H), 7.55 (t, 1H, J = 4.8 Hz, NHC=O), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-136 | 1.29 (t, 3H, CH₃, J = 7.6 Hz), 2.72 (q, 2H, CH₂, J = 7.6 Hz), 5.60 (s, 2H, CH₂ of isoxazole-CH₂), 7.21 (s, 1H, H of isoxazole), 7.35 (d, J = 8.0 Hz, 2H), 7.54 (t, 1H, J = 4.8 Hz, NHC=O), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-137 | 1.35 (s, 9H, 3CH₃), 5.37 (s, 2H, CH₂ of isoxazole-CH₂), 7.26 (s, 1H, H of isoxazole), 7.35 (d, J = 8.0 Hz, 2H), 7.56 (t, 1H, J = 4.8 Hz, NHC=O), 7.59-7.63 (m, 1H), 7.80 (d, J = 8.4 Hz, 2H), 8.37 (dd, J = 1.6, 2.0 Hz, 1H), 8.65 (dd, J = 2.0, 2.0 Hz, 1H). |
| YP-138 | 2.15 (s, 6H, 2CH₃), 2.31 (s, 3H, CH₃), 5.40 (s, 2H, isoxazole-CH₂), 6.33 (s, 1H, H of isoxazole), 6.93 (s, 2H), 7.52 (t, 1H, J = 4.8 Hz, NHC=O), 7.59-7.63 (m, 1H), 8.37 (dd, J = 1.6, 2.0 Hz, 1H), 8.65 (dd, J = 2.0, 2.0 Hz, 1H). |
| YP-139 | 3.83 (s, 3H, OCH₃), 5.58 (s, 2H, isoxazole-CH₂), 7.08 (d, J = 8.8 Hz, 2H), 7.18 (s, 1H, H of isoxazole), 7.50 (t, 1H, J = 4.8 Hz, NHC=O), 7.59-7.62 (m, 1H), 7.84 (d, J = 8.8 Hz, 2H), 8.36 (dd, J = 2.0, 2.0 Hz, 1H), 8.64 (dd, J = 2.0, 2.0 Hz, 1H). |
| YP-140 | 3.83 (s, 3H, OCH₃), 5.58 (s, 2H, isoxazole-CH₂), 7.18 (s, 1H, H of isoxazole), 7.01-7.08 (m, 2H), 7.48 (t, 1H, J = 4.8 Hz, NHC=O), 7.59-7.62 (m, 1H), 7.91 (dd, 1H, J = 1.6, 2.0 Hz), 8.36 (dd, J = 2.0, 2.0 Hz, 1H), 8.64 (dd, J = 2.0, 2.0 Hz, 1H). |
| YP-141 | 3.89 (s, 3H, OCH₃), 5.40 (s, 2H, CH₂ of isoxazole-CH₂), 6.71 (s, 1H, H of isoxazole), 7.38-7.41 (m, 3H), 7.48 (t, 1H, J = 4.8 Hz, NHC=O), 7.59 (dd, 1H, J = 8.8, 4.8 Hz), 7.84 (d, J = 8.8 Hz, 2H), 8.36 (dd, J = 2.0, 2.0 Hz, 1H), 8.64 (dd, J = 2.0, 2.0 Hz, 1H). |
| YP-142 | 5.42 (s, 2H, CH₂ of isoxazole-CH₂), 6.71 (s, 1H, 1H of isoxazole), 7.50 (t, 1H, J = 4.8 Hz, NHC=O), 7.76 (d, 2H, J = 8.4 Hz), 7.84 (d, J = 8.8 Hz, 2H), 7.98 (d, 2H, J = 8.4 Hz), 8.36 (dd, J = 2.0, 2.0 Hz, 1H), 8.64 (dd, J = 2.0, 2.0 Hz, 1H). |
| YP-143 | 5.42 (s, 2H, CH₂ of isoxazole-CH₂), 6.87 (s, 1H, 1H of isoxazole), 7.18-7.26 (m, 2H), 7.43-7.49 (m, 1H), 7.54 (t, 1H, J = 4.8 Hz, NHC=O), 7.84 (d, J = 8.8 Hz, 2H), 8.36 (dd, J = 2.0, 2.0 Hz, 1H), 8.64 (dd, J = 2.0, 2.0 Hz, 1H). |
| YP-144 | 5.40 (s, 2H, CH₂ of isoxazole-CH₂), 6.69 (s, 1H, 1H of isoxazole), 7.20 (d, 2H, J = 8.8 Hz), 7.56 (t, 1H, J = 4.8 Hz, NHC=O), 7.84 (d, J = 8.8 Hz, 2H), 7.85 (d, 2H, 2H, J = 8.8 Hz), 8.36 (dd, J = 2.0, 2.0 Hz, 1H), 8.64 (dd, J = 2.0, 2.0 Hz, 1H). |
| YP-145 | 5.41 (s, 2H, CH₂ of isoxazole-CH₂), 6.92 (s, 1H, 1H of isoxazole), 7.01-7.08 (m, 2H), 7.42-7.46 (m, 1H), 7.52 (t, 1H, J = 4.8 Hz, NHC=O), 7.59 (dd, 1H, J = 8.8, 4.8 Hz), 7.85 (d, 2H, 2H, J = 8.8 Hz), 8.36 (dd, J = 2.0, 2.0 Hz, 1H), 8.64 (dd, J = 2.0, 2.0 Hz, 1H). |
| YP-146 | 5.60 (s, 2H, isoxazole-CH₂), 7.29 (s, 1H, H of isoxazole), 7.51 (t, 1H, J = 4.8 Hz, NHC=O), 7.59-7.62 (m, 3H), 7.94 (d, J = 8.8 Hz, 2H), 8.37 (dd, J = 1.6, 2.0 Hz, 1H), 8.64 (dd, J = 2.0, 2.0 Hz, 1H). |
| YP-147 | 5.63 (s, 2H, isoxazole-CH₂), 7.13 (s, 1H, H of isoxazole), 7.45 (t, 1H, J = 4.8 Hz, NHC=O), 7.48-7.67 (m, 4H), 7.73 (dd, J = 2.0, 1.6 Hz, 1H), 8.37 (dd, J = 1.6, 2.0 Hz, 1H), 8.63-8.64 (m, 1H). |
| YP-148 | 5.63 (s, 2H, isoxazole-CH₂), 7.16 (s, 1H, H of isoxazole), 7.48 (t, 1H, J = 4.8 Hz, NHC=O), 7.57-7.62 (m, 2H), 7.77 (d, J = 8.4 Hz, 1H), 7.86 (d, J = 2.0 Hz, 1H), 8.36 (dd, J = 2.0, 2.0 Hz, 1H), 8.64 (dd, J = 2.0, 2.0 Hz, 1H). |
| YP-149 | 5.60 (s, 2H, isoxazole-CH₂), 7.29 (s, 1H, H of isoxazole), 7.56 (t, 1H, J = 4.8 Hz, NHC=O), 7.61 (dd, J = 4.8, 4.8 Hz, 1H), 7.76 (d, J = 8.4 Hz, 2H), 7.87 (d, J = 8.8 Hz, 2H), 8.37 (dd, J = 2.0, 1.6 Hz, 1H), 8.64 (dd, J = 1.6, 1.6 Hz, 1H). |
| YP-150 | 5.63 (s, 2H, isoxazole-CH₂), 7.13 (s, 1H, H of isoxazole), 7.45 (t, 1H, J = 4.8 Hz, NHC=O), 7.48-7.67 (m, 4H), 7.73 (dd, J = 2.0, 1.6 Hz, 1H), 8.37 (dd, J = 1.6, 2.0 Hz, 1H), 8.63-8.64 (m, 1H). |
| YP-151 | 5.40 (s, 2H, CH₂ of isoxazole-CH₂), 6.71 (s, 1H, H of isoxazole), 7.38-7.41 (m, 3H), 7.48 (t, 1H, J = 4.8 Hz, NHC=O), 7.59 (dd, 1H, J = 8.8, 4.8 Hz), 7.84 (d, J = 8.8 Hz, 2H), 8.36 (dd, J = 2.0, 2.0 Hz, 1H), 8.64 (dd, J = 2.0, 2.0 Hz, 1H). |
| YP-152 | 5.60 (s, 2H, isoxazole-CH₂), 7.29 (s, 1H, H of isoxazole), 7.48 (t, 1H, J = 4.8 Hz, NHC=O), 7.61 (dd, J = 4.8, 4.8 Hz, 1H), 7.76 (d, J = 8.4 Hz, 2H), 7.87 (d, J = 8.8 Hz, 2H), 8.37 (dd, J = 2.0, 1.6 Hz, 1H), 8.64 (dd, J = 1.6, 1.6 Hz, 1H). |
| YP-153 | 5.60 (s, 2H, isoxazole-CH₂), 7.27 (s, 1H, H of isoxazole), 7.48 (t, 1H, J = 4.8 Hz, NHC=O), 7.52-7.55 (m, 3H), 7.89-7.91 (m, 2H), 8.47 (d, J = 2.8 Hz, 1H), 8.75 (d, J = 2.8 Hz, 1H). |
| YP-154 | 2.37 (s, 3H, CH₃), 5.59 (s, 2H, isoxazole-CH₂), 7.22 (s, 1H, H of isoxazole), 7.35 (d, J = 8.0 Hz, 2H), 7.48 (t, 1H, J = 4.8 Hz, NHC=O), 7.79 (d, J = 8.0 Hz, 2H), 8.46 (d, J = 2.8 Hz, 1H), 8.74 (d, J = 2.4 Hz, 1H). |
| YP-155 | 1.29 (t, 3H, CH₃, J = 7.6 Hz), 2.72 (q, 2H, CH₂, J = 7.6 Hz), 7.22 (s, 1H, H of isoxazole), 7.35 (d, J = 8.0 Hz, 2H), 7.48 (t, 1H, J = 4.8 Hz, NHC=O), 7.79 (d, J = 8.0 Hz, 2H), 8.46 (d, J = 2.8 Hz, 1H), 8.74 (d, J = 2.4 Hz, 1H). |
| YP-156 | 1.35 (s, 9H, 3CH₃), 7.22 (s, 1H, H of isoxazole), 7.35 (d, J = 8.0 Hz, 2H), 7.48 (t, 1H, J = 4.8 Hz, NHC=O), 7.79 (d, J = 8.0 Hz, 2H), 8.46 (d, J = 2.8 Hz, 1H), 8.74 (d, J = 2.4 Hz, 1H). |
| YP-157 | 2.15 (s, 6H, 2CH₃), 2.31 (s, 3H, CH₃), 7.22 (s, 1H, H of isoxazole), 7.35 (d, J = 8.0 Hz, 2H), 7.48 (t, 1H, J = 4.8 Hz, NHC=O), 7.79 (d, J = 8.0 Hz, 2H), 8.46 (d, J = 2.8 Hz, 1H), 8.74 (d, J = 2.4 Hz, 1H). |
| YP-158 | 3.82 (s, 3H, OCH₃), 5.57 (s, 2H, isoxazole-CH₂), 7.08 (d, J = 9.2 Hz, 2H), 7.20 (s, 1H, H of isoxazole), 7.48 (t, 1H, J = 4.8 Hz, NHC=O), 7.84 (d, J = 8.8 Hz, 2H), 8.46 (d, J = 2.4 Hz, 1H), 8.75 (d, J = 2.4 Hz, 1H). |

TABLE 2-continued

¹H NMR data of compounds in Table 1

| No. | ¹H NMR (400 MHz, DMSO-d$_6$) |
|---|---|
| YP-159 | 3.82 (s, 3H, OCH$_3$), 5.57 (s, 2H, isoxazole-CH$_2$), 7.01-7.08 (m, 2H), 7.42-7.46 (m, 1H), 7.51 (t, 1H, J = 4.8 Hz, NHC=O), 7.59 (dd, 1H, J = 8.8, 4.8 Hz), 8.46 (d, J = 2.4 Hz, 1H), 8.75 (d, J = 2.4 Hz, 1H). |
| YP-160 | 3.89 (s, 3H, OCH$_3$), 5.40 (s, 2H, CH$_2$ of isoxazole-CH$_2$), 6.71 (s, 1H, H of isoxazole), 7.00-7.04 (m, 1H), 7.38-7.41 (m, 3H), 7.48 (t, 1H, J = 4.8 Hz, NHC=O), 8.46 (d, J = 2.4 Hz, 1H), 8.75 (d, J = 2.4 Hz, 1H). |
| YP-161 | 5.42 (s, 2H, CH$_2$ of isoxazole-CH$_2$), 6.71 (s, 1H, 1H of isoxazole), 7.48 (t, 1H, J = 4.8 Hz, NHC=O), 7.76 (d, 2H, J = 8.4 Hz), 7.98 (d, 2H, J = 8.4 Hz), 8.46 (d, J = 2.4 Hz, 1H), 8.75 (d, J = 2.4 Hz, 1H). |
| YP-162 | 5.42 (s, 2H, CH$_2$ of isoxazole-CH$_2$), 6.87 (s, 1H, 1H of isoxazole), 7.18-7.26 (m, 2H), 7.42-7.46 (m, 1H), 7.43-7.49 (m, 1H), 7.50 (t, 1H, J = 4.8 Hz, NHC=O), 8.46 (d, J = 2.4 Hz, 1H), 8.75 (d, J = 2.4 Hz, 1H). |
| YP-163 | 5.60 (s, 2H, isoxazole-CH$_2$), 7.30 (s, 1H, H of isoxazole), 7.48 (t, 1H, J = 4.8 Hz, NHC=O), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-164 | 5.63 (s, 2H, isoxazole-CH$_2$), 7.15 (s, 1H, H of isoxazole), 7.48-7.52 (m, 1H), 7.53 (t, 1H, J = 4.8 Hz, NHC=O), 7.54-7.58 (m, 1H), 7.67 (dd, J = 1.2, 1.2 Hz, 1H), 7.72 (dd, J = 1.6, 2.0 Hz, 1H), 8.46 (d, J = 2.8 Hz, 1H), 8.75 (d, J = 2.4 Hz, 1H). |
| YP-165 | 5.60 (s, 2H, isoxazole-CH$_2$), 7.30 (s, 1H, H of isoxazole), 7.48 (t, 1H, J = 4.8 Hz, NHC=O), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-166 | 5.60 (s, 2H, isoxazole-CH$_2$), 7.30 (s, 1H, H of isoxazole), 7.48 (t, 1H, J = 4.8 Hz, NHC=O), 7.75 (d, J = 8.4 Hz, 2H), 7.87 (d, J = 8.8 Hz, 2H), 8.47 (d, J = 2.8 Hz, 1H), 8.75 (d, J = 2.4 Hz, 1H). |
| YP-167 | 5.60 (s, 2H, isoxazole-CH$_2$), 7.30 (s, 1H, H of isoxazole), 7.48 (t, 1H, J = 4.8 Hz, NHC=O), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-168 | 5.63 (s, 2H, isoxazole-CH$_2$), 7.15 (s, 1H, H of isoxazole), 7.48-7.52 (m, 1H), 7.56 (t, 1H, J = 4.8 Hz, NHC=O), 7.54-7.58 (m, 1H), 7.67 (dd, J = 1.2, 1.2 Hz, 1H), 7.72 (dd, J = 1.6, 2.0 Hz, 1H), 8.46 (d, J = 2.8 Hz, 1H), 8.75 (d, J = 2.4 Hz, 1H). |
| YP-169 | 5.40 (s, 2H, CH$_2$ of isoxazole-CH$_2$), 6.71 (s, 1H, 1H of isoxazole), 7.00-7.04 (m, 1H), 7.38-7.41 (m, 3H), 7.48 (t, 1H, J = 4.8 Hz, NHC=O), 8.46 (d, J = 2.8 Hz, 1H), 8.75 (d, J = 2.4 Hz, 1H). |
| YP-170 | 5.60 (s, 2H, isoxazole-CH$_2$), 7.30 (s, 1H, H of isoxazole), 7.48 (t, 1H, J = 4.8 Hz, NHC=O), 7.62 (d, J = 8.8 Hz, 2H), 7.94 (d, J = 8.8 Hz, 2H), 8.46 (d, J = 2.4 Hz, 1H), 8.74 (d, J = 2.8 Hz, 1H). |
| YP-171 | 5.65 (s, 2H, isoxazole-CH$_2$), 7.32 (s, 1H, H of isoxazole), 7.48 (t, 1H, J = 4.8 Hz, NHC=O), 7.51-7.55 (m, 3H), 7.89-7.92 (m, 2H), 8.12 (d, J = 8.0 Hz, 1H), 8.65 (dd, J = 1.6, 1.6 Hz, 1H), 9.33 (d, J = 1.6 Hz, 1H). |
| YP-172 | 2.37 (s, 3H, CH$_3$), 5.63 (s, 2H, isoxazole-CH$_2$), 7.25 (s, 1H, H of isoxazole), 7.35 (d, J = 8.0 Hz, 2H), 7.48 (t, 1H, J = 4.8 Hz, NHC=O), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-173 | 1.29 (t, 3H, CH$_3$, J = 7.6 Hz), 2.72 (q, 2H, CH$_2$, J = 7.6 Hz), 5.63 (s, 2H, isoxazole-CH$_2$), 7.25 (s, 1H, H of isoxazole), 7.35 (d, J = 8.0 Hz, 2H), 7.48 (t, 1H, J = 4.8 Hz, NHC=O), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-174 | 1.35 (s, 9H, 3CH$_3$), 5.63 (s, 2H, isoxazole-CH$_2$), 7.25 (s, 1H, H of isoxazole), 7.35 (d, J = 8.0 Hz, 2H), 7.48 (t, 1H, J = 4.8 Hz, NHC=O), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-175 | 2.15 (s, 6H, 2CH$_3$), 2.31 (s, 3H, CH$_3$), 5.63 (s, 2H, isoxazole-CH$_2$), 7.25 (s, 1H, H of isoxazole), 7.35 (d, J = 8.0 Hz, 2H), 7.48 (t, 1H, J = 4.8 Hz, NHC=O), 7.80 (d, J = 8.4 Hz, 2H), 8.12 (d, J = 8.0 Hz, 1H), 8.65 (dd, J = 1.6, 1.6 Hz, 1H), 9.32 (d, J = 1.6 Hz, 1H). |
| YP-176 | 2.91 (s, 3H, CH$_3$), 5.62 (s, 2H, isoxazole-CH$_2$), 7.08 (d, J = 8.0 Hz, 2H), 7.23 (s, 1H, H of isoxazole), 7.48 (t, 1H, J = 4.8 Hz, NHC=O), 7.84 (d, J = 6.8 Hz, 2H), 8.12 (d, J = 8.0 Hz, 1H), 8.63 (t, J = 8.4 Hz, 1H), 9.32 (d, J = 1.2 Hz, 1H). |
| YP-177 | 3.92 (s, 3H, OCH$_3$), 5.62 (s, 2H, isoxazole-CH$_2$), 7.23 (s, 1H, H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 8.12 (d, J = 8.0 Hz, 1H), 8.63 (t, J = 8.4 Hz, 1H), 9.32 (d, J = 1.2 Hz, 1H). |
| YP-178 | 3.92 (s, 3H, OCH$_3$), 5.62 (s, 2H, isoxazole-CH$_2$), 7.23 (s, 1H, H of isoxazole), 7.00-7.04 (m, 1H), 7.38-7.41 (m, 3H), 7.48 (t, 1H, J = 4.8 Hz, NHC=O), 8.12 (d, J = 8.0 Hz, 1H), 8.63 (t, J = 8.4 Hz, 1H), 9.32 (d, J = 1.2 Hz, 1H). |
| YP-179 | 5.42 (s, 2H, CH$_2$ of isoxazole-CH$_2$), 6.71 (s, 1H, 1H of isoxazole), 7.48 (t, 1H, J = 4.8 Hz, NHC=O), 7.76 (d, 2H, J = 8.4 Hz), 7.98 (d, 2H, J = 8.4 Hz), 8.12 (d, J = 8.0 Hz, 1H), 8.63 (t, J = 8.4 Hz, 1H), 9.32 (d, J = 1.2 Hz, 1H). |
| YP-180 | 5.42 (s, 2H, CH$_2$ of isoxazole-CH$_2$), 6.87 (s, 1H, 1H of isoxazole), 7.18-7.26 (m, 2H), 7.42-7.46 (m, 1H), 7.43-7.49 (m, 1H), 7.51 (t, 1H, J = 4.8 Hz, NHC=O), 8.12 (d, J = 8.0 Hz, 1H), 8.63 (t, J = 8.4 Hz, 1H), 9.32 (d, J = 1.2 Hz, 1H). |
| YP-181 | 5.40 (s, 2H, CH$_2$ of isoxazole-CH$_2$), 6.69 (s, 1H, 1H of isoxazole), 7.20 (d, 2H, J = 8.8 Hz), 7.50 (t, 1H, J = 4.8 Hz, NHC=O), 7.85 (d, 2H, J = 8.8 Hz), 8.12 (d, J = 8.0 Hz, 1H), 8.63 (t, J = 8.4 Hz, 1H), 9.32 (d, J = 1.2 Hz, 1H). |
| YP-182 | 5.41 (s, 2H, CH$_2$ of isoxazole-CH$_2$), 6.92 (s, 1H, 1H of isoxazole), 7.01-7.08 (m, 2H), 7.42-7.46 (m, 1H), 7.48 (t, 1H, J = 4.8 Hz, NHC=O), 7.59 (dd, 1H, J = 8.8, 4.8 Hz), 8.12 (d, J = 8.0 Hz, 1H), 8.63 (t, J = 8.4 Hz, 1H), 9.32 (d, J = 1.2 Hz, 1H). |

TABLE 2-continued

¹H NMR data of compounds in Table 1

| No. | ¹H NMR (400 MHz, DMSO-d$_6$) |
|---|---|
| YP-183 | 5.65 (s, 2H, isoxazole-CH$_2$), 7.34 (s, 1H, H of isoxazole), 7.48 (t, 1H, J = 4.8 Hz, NHC=O), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-184 | 5.68 (s, 2H, isoxazole-CH$_2$), 7.18 (s, 1H, H of isoxazole), 7.48-7.52 (m, 1H), 7.55 (t, 1H, J = 4.8 Hz, NHC=O), 7.54-7.59 (m, 2H), 7.68 (dd, J = 1.6, 0.8 Hz, 1H), 7.30 (dd, J = 1.6, 2.0 Hz, 1H), 8.11 (d, J = 8.0 Hz, 1H), 8.63 (dt, J = 2.4, 0.4 Hz, 1H), 9.31 (d, J = 2.0 Hz, 1H). |
| YP-185 | 5.65 (s, 2H, isoxazole-CH$_2$), 7.33 (s, 1H, H of isoxazole), 7.56 (t, 1H, J = 4.8 Hz, NHC=O), 7.75 (d, J = 8.8 Hz, 2H), 7.87 (d, J = 8.4 Hz, 2H), 8.12 (d, J = 8.0 Hz, 2H), 8.65 (dd, J = 1.6, 1.6 Hz, 1H), 9.32 (d, J = 1.6 Hz, 1H). |
| YP-186 | 5.65 (s, 2H, isoxazole-CH$_2$), 7.34 (s, 1H, H of isoxazole), 7.48 (t, 1H, J = 4.8 Hz, NHC=O), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-187 | 5.68 (s, 2H, isoxazole-CH$_2$), 7.18 (s, 1H, H of isoxazole), 7.48-7.52 (m, 1H), 7.54 (t, 1H, J = 4.8 Hz, NHC=O), 7.54-7.59 (m, 2H), 7.68 (dd, J = 1.6, 0.8 Hz, 1H), 7.30 (dd, J = 1.6, 2.0 Hz, 1H), 8.11 (d, J = 8.0 Hz, 1H), 8.63 (dt, J = 2.4, 0.4 Hz, 1H), 9.31 (d, J = 2.0 Hz, 1H). |
| YP-188 | 5.62 (s, 2H, isoxazole-CH$_2$), 7.23 (s, 1H, H of isoxazole), 7.00-7.04 (m, 1H), 7.38-7.41 (m, 3H), 7.48 (t, 1H, J = 4.8 Hz, NHC=O), 8.12 (d, J = 8.0 Hz, 1H), 8.63 (t, J = 8.4 Hz, 1H), 9.32 (d, J = 1.2 Hz, 1H). |
| YP-189 | 5.65 (s, 2H, isoxazole-CH$_2$), 7.34 (s, 1H, H of isoxazole), 7.48 (t, 1H, J = 4.8 Hz, NHC=O), 7.59-7.62 (m, 2H), 7.91-7.95 (m, 2H), 8.12 (d, J = 8.4 Hz, 1H), 8.64 (dd, J = 1.6, 1.6 Hz, 1H), 9.32 (d, J = 1.6 Hz, 1H). |
| YP-190 | 2.81 (s, 3H, CH$_3$), 5.61 (s, 2H, isoxazole-CH$_2$), 7.28 (s, 1H, H of isoxazole), 7.48 (t, 1H, J = 4.8 Hz, NHC=O), 7.52-7.55 (m, 3H), 7.90-7.92 (m, 3H), 8.53 (d, J = 8.0 Hz, 1H). |
| YP-191 | 2.42 (s, 3H, CH$_3$), 2.86 (s, 3H, CH$_3$), 5.64 (s, 2H, isoxazole-CH$_2$), 7.27 (s, 1H, H of isoxazole), 7.39 (d, J = 8.0 Hz, 2H), 7.48 (t, 1H, J = 4.8 Hz, NHC=O), 7.85 (d, J = 8.0 Hz, 2H), 7.86 (d, J = 8.0 Hz, 1H), 8.57 (d, J = 8.0 Hz, 1H). |
| YP-192 | 1.29 (t, 3H, CH$_3$, J = 7.6 Hz), 2.72 (q, 2H, CH$_2$, J = 7.6 Hz), 2.86 (s, 3H, CH$_3$), 5.64 (s, 2H, isoxazole-CH$_2$), 7.27 (s, 1H, H of isoxazole), 7.39 (d, J = 8.0 Hz, 2H), 7.48 (t, 1H, J = 4.8 Hz, NHC=O), 7.85 (d, J = 8.0 Hz, 2H), 7.86 (d, J = 8.0 Hz, 1H), 8.57 (d, J = 8.0 Hz, 1H). |
| YP-193 | 1.35 (s, 9H, 3CH$_3$), 2.86 (s, 3H, CH$_3$), 5.64 (s, 2H, isoxazole-CH$_2$), 7.27 (s, 1H, H of isoxazole), 7.39 (d, J = 8.0 Hz, 2H), 7.48 (t, 1H, J = 4.8 Hz, NHC=O), 7.85 (d, J = 8.0 Hz, 2H), 7.86 (d, J = 8.0 Hz, 1H), 8.57 (d, J = 8.0 Hz, 1H). |
| YP-194 | 2.15 (s, 6H, 2CH$_3$), 2.31 (s, 3H, CH$_3$), 2.86 (s, 3H, CH$_3$), 5.40 (s, 2H, isoxazole-CH$_2$), 6.33 (s, 1H, H of isoxazole), 6.93 (s, 2H), 7.48 (t, 1H, J = 4.8 Hz, NHC=O), 7.86 (d, J = 8.0 Hz, 1H), 8.57 (d, J = 8.0 Hz, 1H). |
| YP-195 | 2.80 (s, 3H, CH$_3$), 3.82 (s, 3H, OCH$_3$), 5.58 (s, 2H, isoxazole-CH$_2$), 7.08 (d, J = 8.8 Hz, 2H), 7.19 (s, 1H, H of isoxazole), 7.48 (t, 1H, J = 4.8 Hz, NHC=O), 7.85 (d, J = 8.8 Hz, 2H), 7.91 (d, J = 8.4 Hz, 1H), 8.52 (d, J = 8.4 Hz, 1H). |
| YP-196 | 2.80 (s, 3H, CH$_3$), 3.82 (s, 3H, OCH$_3$), 5.58 (s, 2H, isoxazole-CH$_2$), 7.01-7.08 (m, 2H), 7.19 (s, 1H, H of isoxazole), 7.42-7.46 (m, 1H), 7.48 (t, 1H, J = 4.8 Hz, NHC=O), 7.59 (dd, 1H, J = 8.8, 4.8 Hz), 7.91 (d, J = 8.4 Hz, 1H), 8.52 (d, J = 8.4 Hz, 1H). |
| YP-197 | 2.80 (s, 3H, CH$_3$), 3.82 (s, 3H, OCH$_3$), 5.58 (s, 2H, isoxazole-CH$_2$), 7.01-7.08 (m, 2H), 7.19 (s, 1H, H of isoxazole), 7.42-7.46 (m, 1H), 7.48 (t, 1H, J = 4.8 Hz, NHC=O), 7.59 (dd, 1H, J = 8.8, 4.8 Hz), 7.91 (d, J = 8.4 Hz, 1H), 8.52 (d, J = 8.4 Hz, 1H). |
| YP-198 | 2.80 (s, 3H, CH$_3$), 3.82 (s, 3H, OCH$_3$), 5.58 (s, 2H, isoxazole-CH$_2$), 6.71 (s, 1H, H of isoxazole), 7.38-7.41 (m, 3H), 7.48 (t, 1H, J = 4.8 Hz, NHC=O), 7.59 (dd, 1H, J = 8.8, 4.8 Hz), 7.91 (d, J = 8.4 Hz, 1H), 8.52 (d, J = 8.4 Hz, 1H). |
| YP-199 | 2.80 (s, 3H, CH$_3$), 5.42 (s, 2H, CH$_2$ of isoxazole-CH$_2$), 6.71 (s, 1H, 1H of isoxazole), 7.48 (t, 1H, J = 4.8 Hz, NHC=O), 7.76 (d, 2H, J = 8.4 Hz), 7.98 (d, 2H, J = 8.4 Hz), 7.91 (d, J = 8.4 Hz, 1H), 8.52 (d, J = 8.4 Hz, 1H). |
| YP-200 | 2.80 (s, 3H, CH$_3$), 5.42 (s, 2H, CH$_2$ of isoxazole-CH$_2$), 6.87 (s, 1H, 1H of isoxazole), 7.18-7.26 (m, 2H), 7.43-7.49 (m, 1H), 7.52 (t, 1H, J = 4.8 Hz, NHC=O), 7.91 (d, J = 8.4 Hz, 1H), 7.99-8.04 (m, 1H), 8.52 (d, J = 8.4 Hz, 1H). |
| YP-201 | 2.80 (s, 3H, CH$_3$), 5.61 (s, 2H, isoxazole-CH$_2$), 7.29 (s, 1H, H of isoxazole), 7.48 (t, 1H, J = 4.8 Hz, NHC=O), 7.59-7.62 (m, 2H), 7.89-7.95 (m, 3H), 8.52 (d, J = 8.0 Hz, 1H). |
| YP-202 | 2.81 (s, 3H, CH$_3$), 5.64 (s, 2H, isoxazole-CH$_2$), 7.15 (s, 1H, H of isoxazole), 7.48 (t, 1H, J = 4.8 Hz, NHC=O), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-203 | 2.80 (s, 3H, CH$_3$), 5.61 (s, 2H, isoxazole-CH$_2$), 7.29 (s, 1H, H of isoxazole), 7.48 (t, 1H, J = 4.8 Hz, NHC=O), 7.59-7.62 (m, 2H), 7.89-7.95 (m, 3H), 8.52 (d, J = 8.0 Hz, 1H). |
| YP-204 | 2.81 (s, 3H, CH$_3$), 5.64 (s, 2H, isoxazole-CH$_2$), 7.15 (s, 1H, H of isoxazole), 7.48 (t, 1H, J = 4.8 Hz, NHC=O), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-205 | 2.81 (s, 3H, CH$_3$), 5.61 (s, 2H, isoxazole-CH$_2$), 7.30 (s, 1H, H of isoxazole), 7.48 (t, 1H, J = 4.8 Hz, NHC=O), 7.74 (d, J = 6.8 Hz, 2H), 7.87 (d, J = 6.8 Hz, 2H), 7.91 (d, J = 8.4 Hz, 1H), 8.52 (d, J = 8.0 Hz, 1H). |
| YP-206 | 2.80 (s, 3H, CH$_3$), 5.61 (s, 2H, isoxazole-CH$_2$), 7.29 (s, 1H, H of isoxazole), 7.48 (t, 1H, J = 4.8 Hz, NHC=O), 7.59-7.62 (m, 2H), 7.89-7.95 (m, 3H), 8.52 (d, J = 8.0 Hz, 1H). |

TABLE 2-continued

¹H NMR data of compounds in Table 1

| No. | ¹H NMR (400 MHz, DMSO-d₆) |
|---|---|
| YP-207 | 2.81 (s, 3H, CH₃), 5.64 (s, 2H, isoxazole-CH₂), 7.15 (s, 1H, H of isoxazole), 7.48 (t, 1H, J = 4.8 Hz, NHC═O), 7.50-7.53 (m, 1H), 7.55-7.59 (m, 1H), 7.67 (dd, J = 1.2, 1.2 Hz, 1H), 7.73 (dd, J = 2.0, 2.0 Hz, 1H), 7.91 (d, J = 8.0 Hz, 1H), 8.52 (d, J = 8.0 Hz, 1H). |
| YP-208 | 2.81 (s, 3H, CH₃), 5.40 (s, 2H, CH₂ of isoxazole-CH₂), 6.71 (s, 1H, 1H of isoxazole), 7.00-7.04 (m, 1H), 7.38-7.41 (m, 3H), 7.48 (t, 1H, J = 4.8 Hz, NHC═O), 7.91 (d, J = 8.0 Hz, 1H), 8.52 (d, J = 8.0 Hz, 1H). |
| YP-209 | 2.81 (s, 3H, CH₃), 5.43 (s, 2H, CH₂ of isoxazole-CH₂), 6.80 (s, 1H, 1H of isoxazole), 7.48 (t, 1H, J = 4.8 Hz, NHC═O), 8.04 (d, 2H, J = 8.8 Hz), 7.79 (d, 2H, J = 8.4 Hz), 7.91 (d, J = 8.0 Hz, 1H), 8.52 (d, J = 8.0 Hz, 1H). |
| YP-210 | 5.56 (s, 2H, isoxazole-CH₂), 7.15-7.21 (m, 3H), 7.26 (s, 1H, H of isoxazole), 7.28-7.30 (m, 1H), 7.44-7.54 (m, 5H), 7.56 (t, 1H, J = 4.8 Hz, NHC═O), 7.89-7.91 (m, 2H), 8.37 (dd, J = 2.4, 2.4 Hz, 1H), 8.80 (d, J = 2.4 Hz, 1H). |
| YP-211 | 2.36 (s, 3H, CH₃), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.53 (t, 1H, J = 4.8 Hz, NHC═O), 7.79 (d, J = 8.0 Hz, 2H), 8.39 (dd, J = 2.4, 2.4 Hz, 1H), 8.79-8.80 (m, 1H). |
| YP-212 | 1.29 (t, 3H, CH₃, J = 7.6 Hz), 2.72 (q, 2H, CH₂, J = 7.6 Hz), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.53 (t, 1H, J = 4.8 Hz, NHC═O), 7.79 (d, J = 8.0 Hz, 2H), 8.39 (dd, J = 2.4, 2.4 Hz, 1H), 8.79-8.80 (m, 1H). |
| YP-213 | 1.35 (s, 9H, 3CH₃), 5.54 (s, 2H, isoxazole-CH₂), 7.15-7.20 (m, 3H), 7.21 (s, 1H, H of isoxazole), 7.28-7.34 (m, 3H), 7.44-7.48 (m, 2H), 7.50 (t, 1H, J = 4.8 Hz, NHC═O), 7.79 (d, J = 8.0 Hz, 2H), 8.39 (dd, J = 2.4, 2.4 Hz, 1H), 8.79-8.80 (m, 1H). |
| YP-214 | 2.15 (s, 6H, 2CH₃), 2.31 (s, 3H, CH₃), 5.54 (s, 2H, isoxazole-CH₂), 6.93 (s, 2H), 7.15-7.20 (m, 3H), 7.21 (s, 1H, H of isoxazole), 7.44-7.48 (m, 2H), 7.51 (t, 1H, J = 4.8 Hz, NHC═O), 8.39 (dd, J = 2.4, 2.4 Hz, 1H), 8.79-8.80 (m, 1H). |
| YP-215 | 3.82 (s, 3H, OCH₃), 5.54 (s, 2H, isoxazole-CH₂), 7.05-7.07 (m, 2H), 7.14-7.21 (m, 3H), 7.22 (s, 1H, H of isoxazole), 7.26-7.30 (m, 1H), 7.44-7.48 (m, 2H), 7.55 (t, 1H, J = 4.8 Hz, NHC═O), 7.82-7.84 (m, 2H), 8.38 (dd, J = 2.4, 2.4 Hz, 1H), 8.79 (d, J = 2.4 Hz, 1H). |
| YP-216 | 3.92 (s, 3H, OCH₃), 5.54 (s, 2H, isoxazole-CH₂), 7.01-7.08 (m, 2H), 7.05-7.07 (m, 2H), 7.14-7.21 (m, 3H), 7.22 (s, 1H, H of isoxazole), 7.42-7.46 (m, 1H), 7.48 (t, 1H, J = 4.8 Hz, NHC═O), 7.59 (dd, 1H, J = 8.8, 4.8 Hz), 8.38 (dd, J = 2.4, 2.4 Hz, 1H), 8.79 (d, J = 2.4 Hz, 1H). |
| YP-217 | 3.89 (s, 3H, OCH₃), 5.40 (s, 2H, CH₂ of isoxazole-CH₂), 6.71 (s, 1H, H of isoxazole), 7.00-7.04 (m, 1H), 7.05-7.07 (m, 2H), 7.14-7.21 (m, 3H), 7.38-7.41 (m, 3H), 7.48 (t, 1H, J = 4.8 Hz, NHC═O), 8.38 (dd, J = 2.4, 2.4 Hz, 1H), 8.79 (d, J = 2.4 Hz, 1H). |
| YP-218 | 5.54 (s, 2H, isoxazole-CH₂), 7.21 (s, 1H, H of isoxazole), 7.28-7.34 (m, 3H), 7.44-7.48 (m, 2H), 7.51 (t, 1H, J = 4.8 Hz, NHC═O), 7.76 (d, 2H, J = 8.4 Hz), 7.98 (d, 2H, J = 8.4 Hz), 8.39 (dd, J = 2.4, 2.4 Hz, 1H), 8.79-8.80 (m, 1H). |
| YP-219 | 5.54 (s, 2H, isoxazole-CH₂), 7.21 (s, 1H, H of isoxazole), 7.18-7.26 (m, 2H), 7.28-7.34 (m, 3H), 7.44-7.48 (m, 3H), 7.53 (t, 1H, J = 4.8 Hz, NHC═O), 8.39 (dd, J = 2.4, 2.4 Hz, 1H), 7.99-8.04 (m, 1H), 8.79-8.80 (m, 1H). |
| YP-220 | 5.57 (s, 2H, isoxazole-CH₂), 7.15-7.28 (m, 4H), 7.29 (s, 1H, H of isoxazole), 7.46 (d, J = 8.0 Hz, 2H), 7.48 (t, 1H, J = 4.8 Hz, NHC═O), 7.60 (d, J = 6.4 Hz, 2H), 7.92-7.94 (m, 2H), 8.37-8.39 (m, 1H), 8.79 (d, J = 2.4 Hz, 1H). |
| YP-221 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.51 (t, 1H, J = 4.8 Hz, NHC═O), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-222 | 5.57 (s, 2H, isoxazole-CH₂), 7.15-7.28 (m, 4H), 7.29 (s, 1H, H of isoxazole), 7.46 (d, J = 8.0 Hz, 2H), 7.48 (t, 1H, J = 4.8 Hz, NHC═O), 7.60 (d, J = 6.4 Hz, 2H), 7.92-7.94 (m, 2H), 8.37-8.39 (m, 1H), 8.79 (d, J = 2.4 Hz, 1H). |
| YP-223 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.52 (t, 1H, J = 4.8 Hz, NHC═O), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-224 | 5.56 (s, 2H, isoxazole-CH₂), 7.15-7.20 (m, 2H), 7.21 (s, 1H, H of isoxazole), 7.26-7.29 (m, 2H), 7.44-7.48 (m, 2H), 7.53 (t, 1H, J = 4.8 Hz, NHC═O), 7.72-7.75 (m, 2H), 7.85-7.87 (m, 2H), 8.38 (dd, J = 2.4, 2.4 Hz, 1H), 8.79 (d, J = 2.8 Hz, 1H). |
| YP-225 | 5.57 (s, 2H, isoxazole-CH₂), 7.15-7.28 (m, 4H), 7.29 (s, 1H, H of isoxazole), 7.46 (d, J = 8.0 Hz, 2H), 7.48 (t, 1H, J = 4.8 Hz, NHC═O), 7.60 (d, J = 6.4 Hz, 2H), 7.92-7.94 (m, 2H), 8.37-8.39 (m, 1H), 8.79 (d, J = 2.4 Hz, 1H). |
| YP-226 | 5.59 (s, 2H, isoxazole-CH₂), 7.12 (s, 1H, H of isoxazole), 7.14-7.16 (m, 1H), 7.19-7.21 (m, 2H), 7.25-7.30 (m, 1H), 7.44-7.49 (m, 3H), 7.50 (t, 1H, J = 4.8 Hz, NHC═O), 7.53-7.57 (m, 1H), 7.64-7.66 (m, 1H), 7.70-7.72 (m, 1H), 8.38 (dd, J = 2.4, 2.4 Hz, 1H), 8.78 (d, J = 2.4 Hz, 1H). |
| YP-227 | 5.40 (s, 2H, CH₂ of isoxazole-CH₂), 6.71 (s, 1H, H of isoxazole), 7.00-7.04 (m, 1H), 7.05-7.07 (m, 2H), 7.14-7.21 (m, 3H), 7.38-7.41 (m, 3H), 7.48 (t, 1H, J = 4.8 Hz, NHC═O), 8.38 (dd, J = 2.4, 2.4 Hz, 1H), 8.79 (d, J = 2.4 Hz, 1H). |
| YP-228 | 5.57 (s, 2H, isoxazole-CH₂), 7.15-7.28 (m, 4H), 7.29 (s, 1H, H of isoxazole), 7.48 (t, 1H, J = 4.8 Hz, NHC═O), 7.79 (d, 2H, J = 8.4 Hz), 7.92-7.94 (m, 2H), 8.04 (d, J = 6.4 Hz, 2H), 8.37-8.39 (m, 1H), 8.79 (d, J = 2.4 Hz, 1H). |

EXAMPLE 3

Biological Activity Test

The exemplary example compounds were subjected to test of the activity of resisting colorectal cancer cell line HCT-116, human lung cancer cell line A549 and breast cancer cell line MCF-7 by MTT method. The specific test process was as follows:

(1) The lung cancer cell line A549 was plated in a 96-well plate and cultured in 100 μL medium. Until the cells were grown to 90%, 1 μL of the drug (i.e., the above example compounds) was added to the wells, each drug was tested for 8 different concentrations (the initial concentration of the drug, 50 μM, 5 μM, 500 nM, 50 nM, 5 nM, 500 μM, 50 μm, respectively), and each concentration of drug was experimented in 3 wells. After cultivation for 24 h, 20 μL of the already formulated 5 mg/mL MTT solution was added to each well, and the medium was aspirated after 4 hours, 150 μL DMSO was added to each well and its optical density (OD) value was measured at a wavelength of 595 nm. The negative control was DMSO.

The $IC_{50}$ value was calculated by GraphPad Prism5 software.

(2) Test procedure for colorectal cancer cell line HCT-116 and breast cancer cell line MCF-7 was the same as that for lung cancer cell line A549.

The activities of exemplary example compounds in inhibiting human lung cancer cell A549, colorectal cancer cell line HCT-116 and breast cancer cell line MCF-7 were shown in Table 3, Table 4 and Table 5 below.

TABLE 3

Test results of the activity of exemplary example compounds in inhibiting human lung cancer cell A549

| Compound No. | $IC_{50}$ (μM) | Compound No. | $IC_{50}$ (μM) |
|---|---|---|---|
| YP-44 | 171.9 | YP-51 | 187.2 |
| YP-63 | 153.8 | YP-89 | 896.3 |
| YP-78 | 197.6 | YP-108 | 240.7 |
| YP-73 | 207.2 | | |
| | | Gefitinib | 21.55 |

TABLE 4

Test results of the activity of exemplary example compounds in inhibiting colorectal cancer cell line HCT-116

| Compound No. | $IC_{50}$ (μM) | Compound No. | $IC_{50}$ (μM) |
|---|---|---|---|
| YP-44 | 1635.0 | YP-63 | 286.8 |
| YP-89 | 278.7 | YP-78 | 72.5 |
| | | Gefitinib | 17.9 |

TABLE 5

Test results of the activity of exemplary example compounds in inhibiting breast cancer cell line MCF-7

| Compound No. | $IC_{50}$ (μM) | Compound No. | $IC_{50}$ (μM) |
|---|---|---|---|
| YP-44 | 149.4 | YP-63 | 131.6 |
| YP-78 | 159.8 | YP-89 | 124.3 |
| YP-108 | 112.2 | YP-73 | 43.0 |
| | | Gefitinib | 20.68 |

The embodiments of the present invention have been described above. However, the present invention is not limited to the above-described embodiments. Any modifications, equivalent substitutions, improvements and the like within the spirit and principles of the present invention are intended to be included in the scope of the present invention.

The invention claimed is:

1. A compound having one of the following formulae and a pharmaceutically acceptable salt or solvate thereof:

YP-1

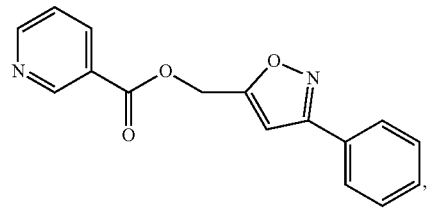

YP-2

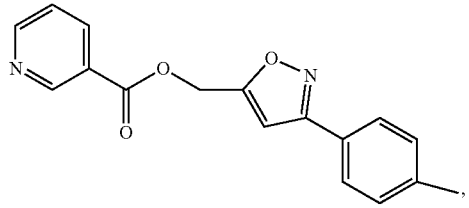

YP-3

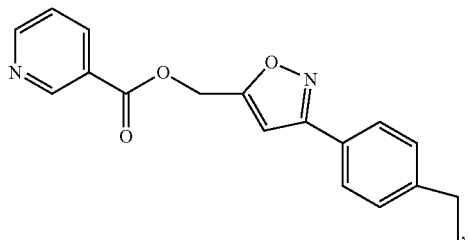

YP-4

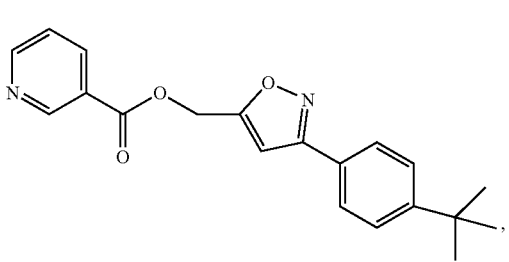

YP-5

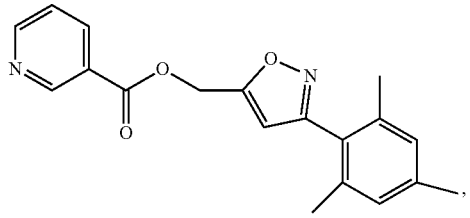

YP-6
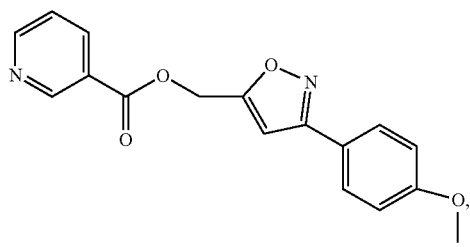
YP-7
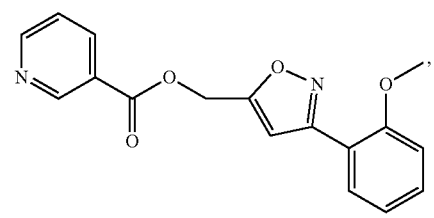
YP-8
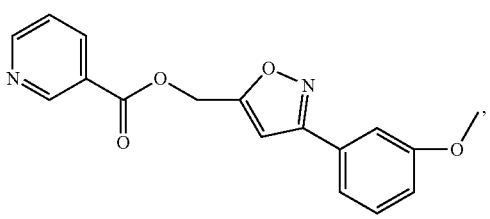
YP-9
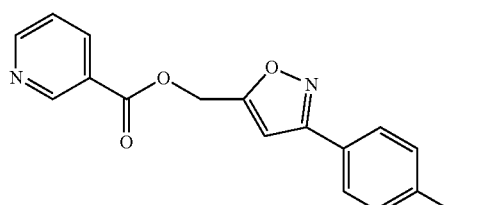
YP-10
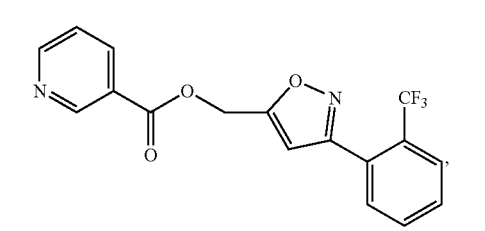
YP-11
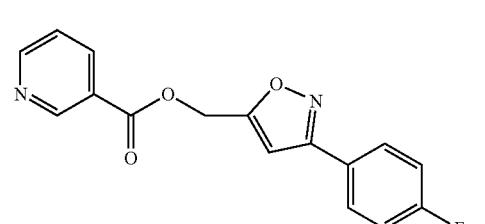
YP-12
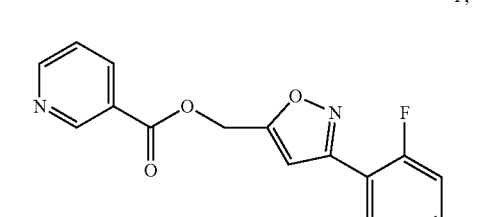
YP-13
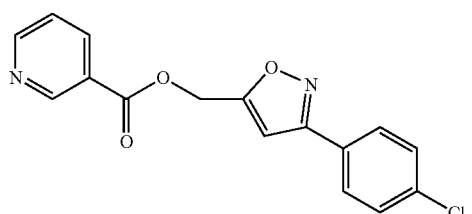
YP-14
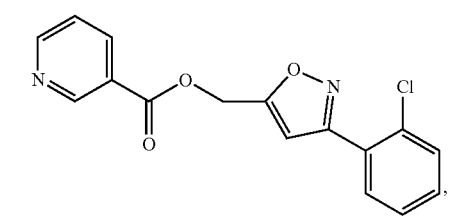
YP-15
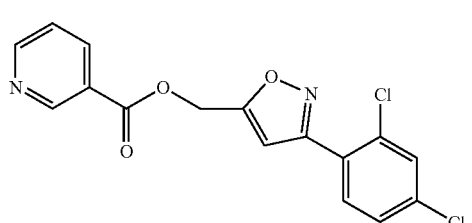
YP-16
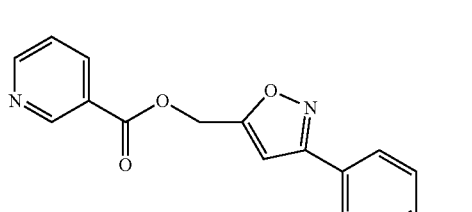
YP-17
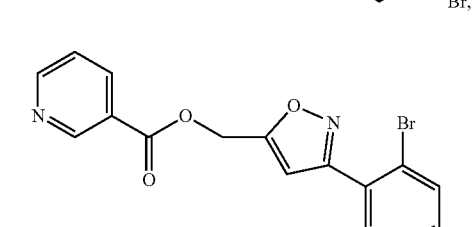
YP-18
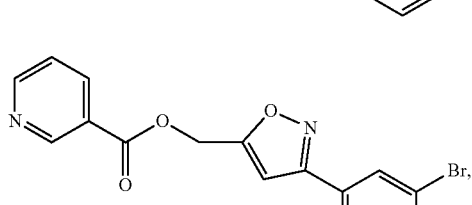
YP-19
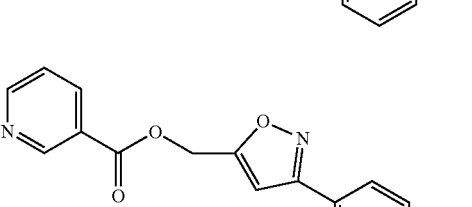

YP-20
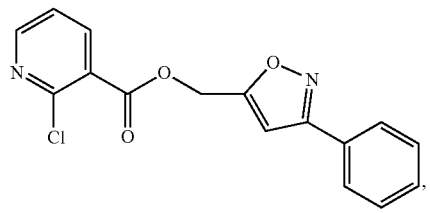
YP-21
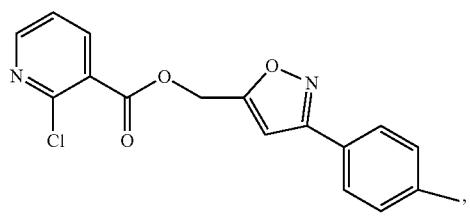
YP-22
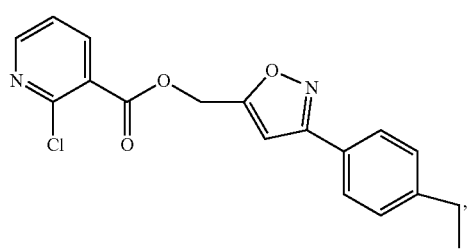
YP-23
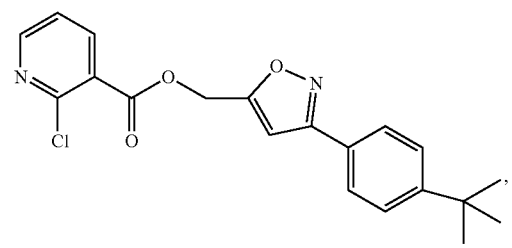
YP-24
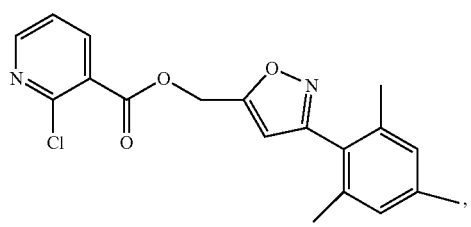
YP-25
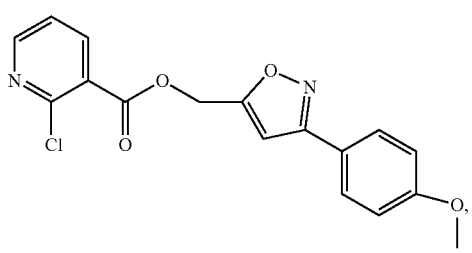
YP-26
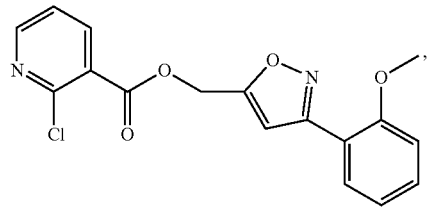
YP-27
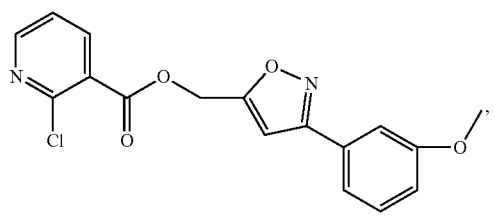
YP-28
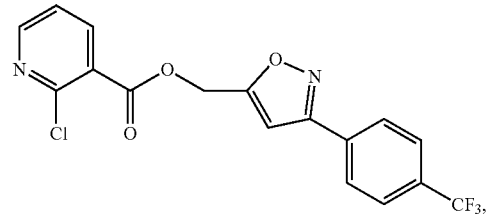
YP-29
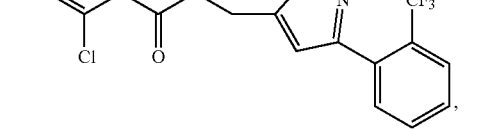
YP-30
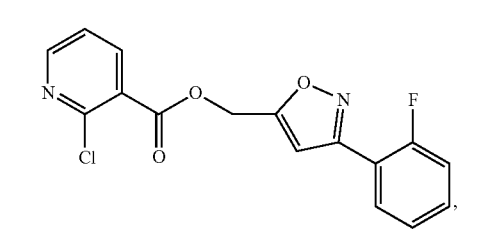
YP-31
YP-32
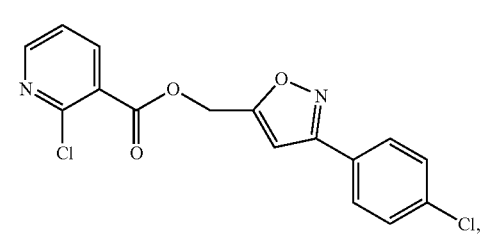

YP-33
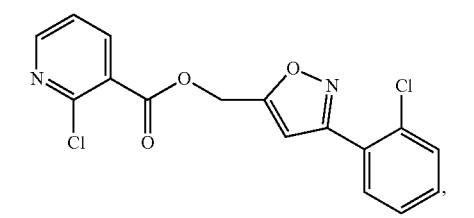
YP-34
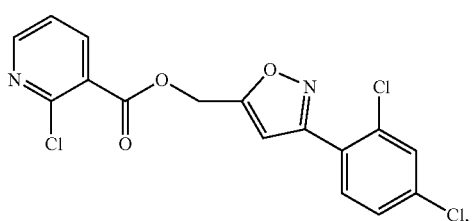
YP-35
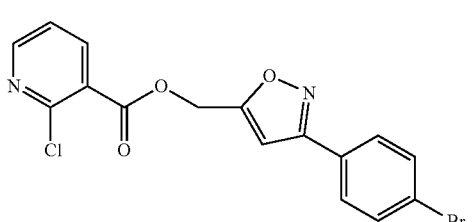
YP-36
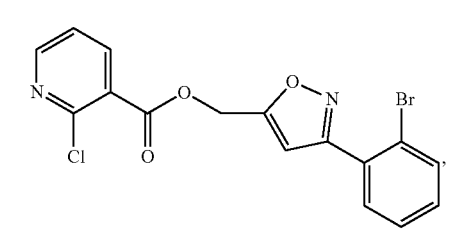
YP-37
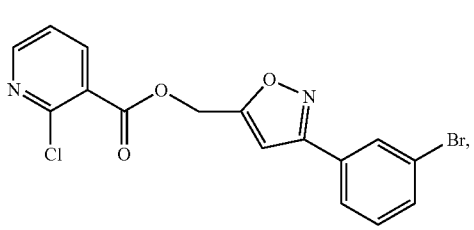
YP-38
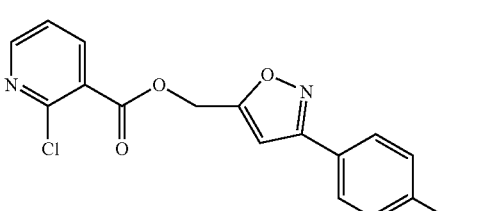
YP-39
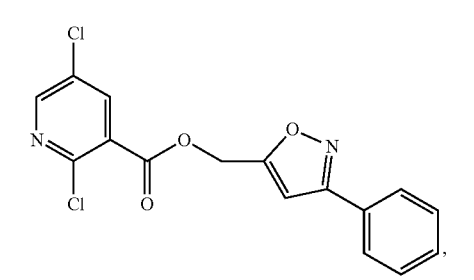
YP-40
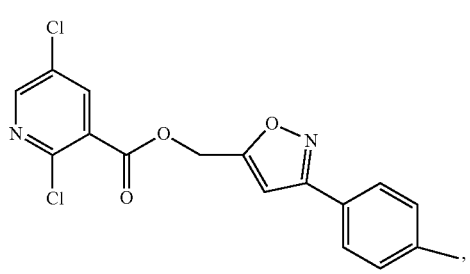
YP-41
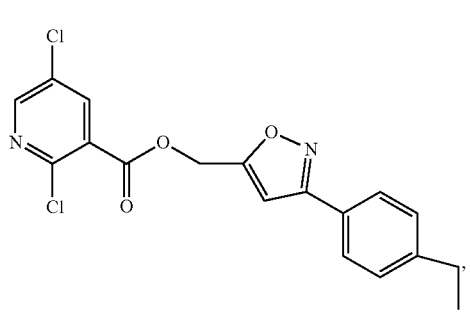
YP-42
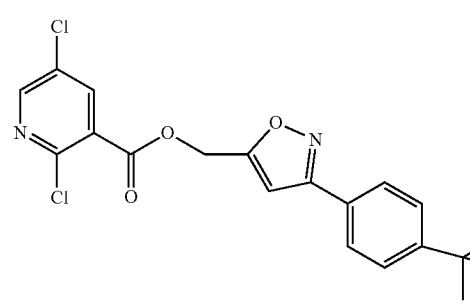
YP-43
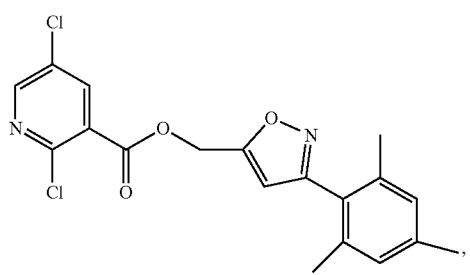
YP-44
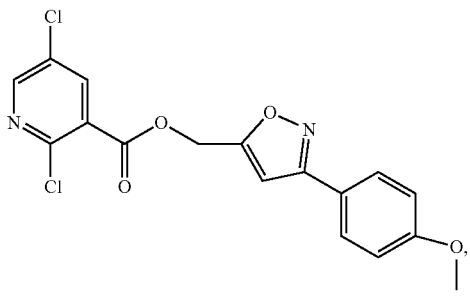

YP-45
YP-46
YP-47
YP-48
YP-49
YP-50
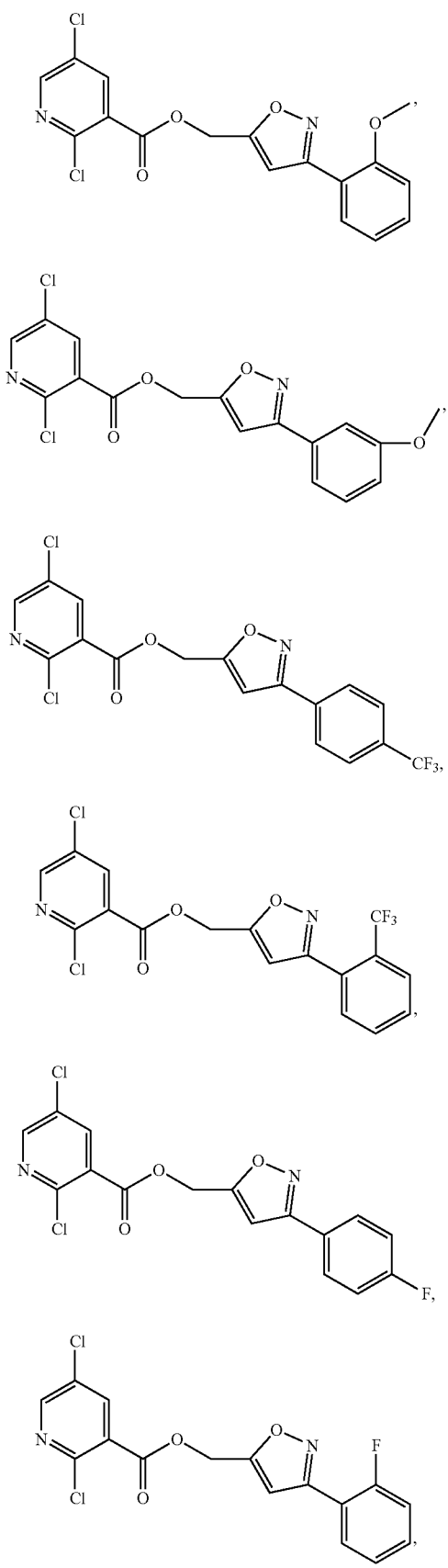
YP-51
YP-52
YP-53
YP-54
YP-55
YP-56
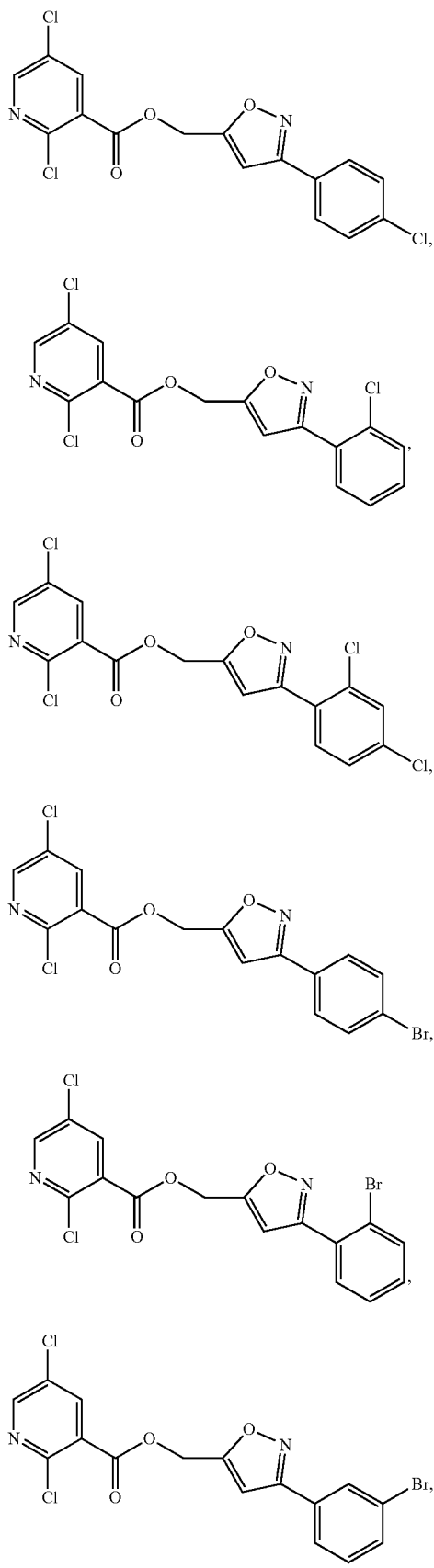

YP-57
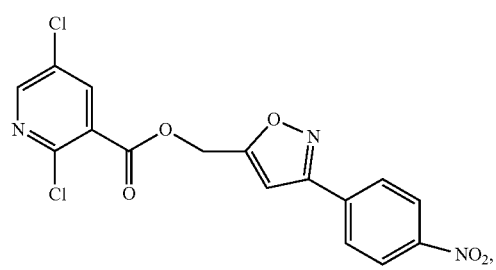
YP-58
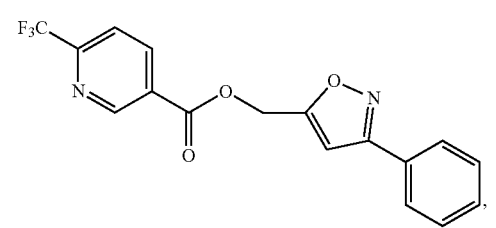
YP-59
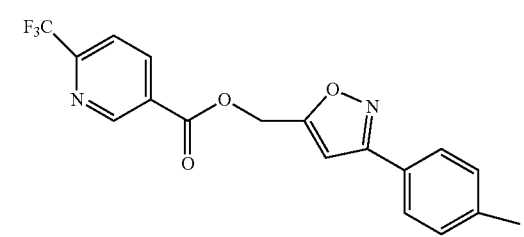
YP-60
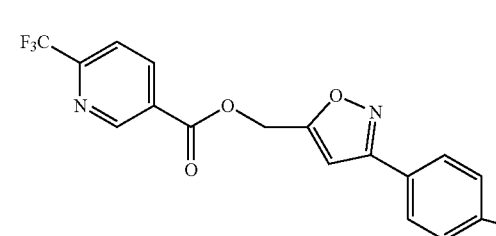
YP-61
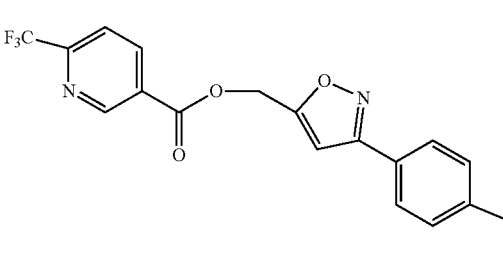
YP-62
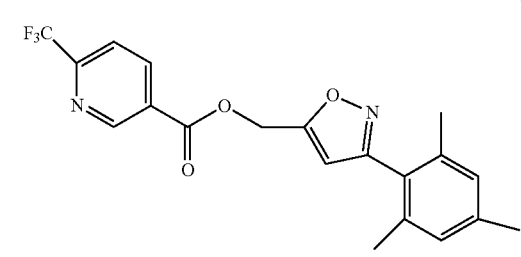
YP-63
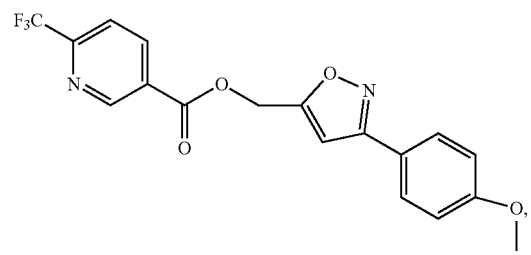
YP-64
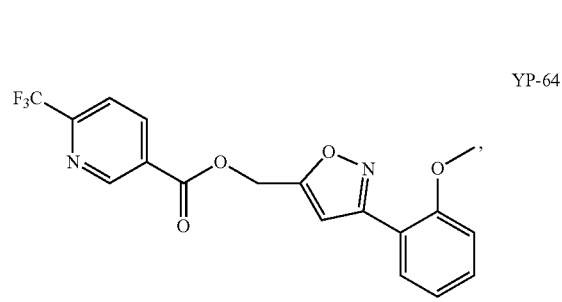
YP-65
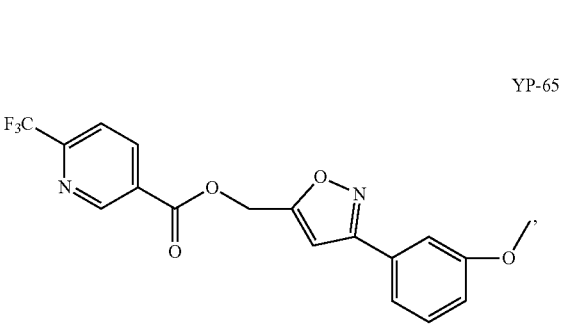
YP-66
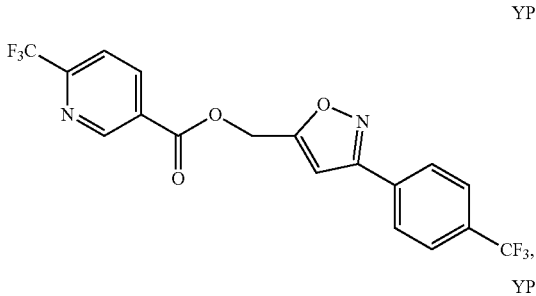
YP-67
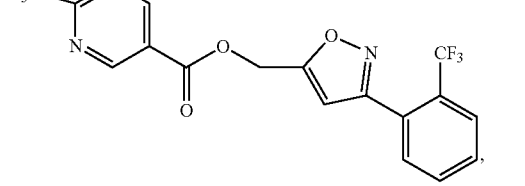
YP-68
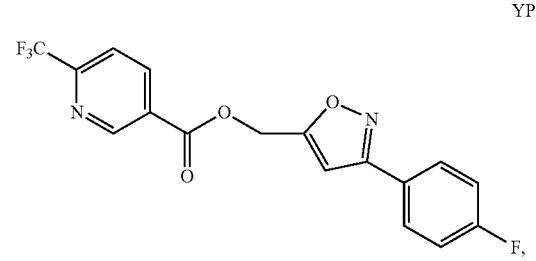

YP-69
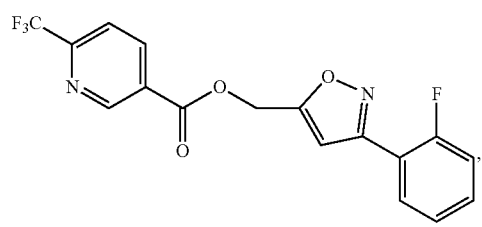
YP-70
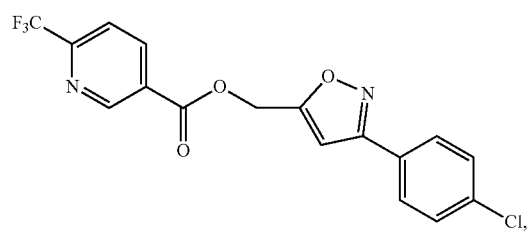
YP-71
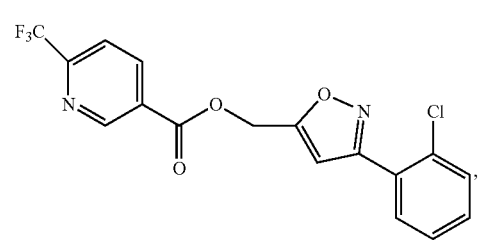
YP-72
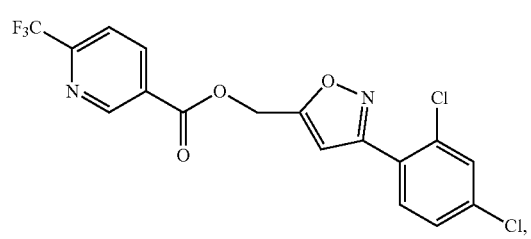
YP-73
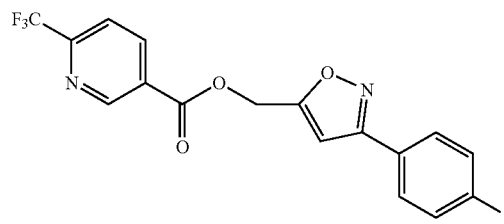
YP-74
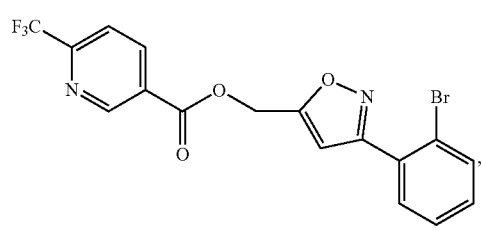
YP-75
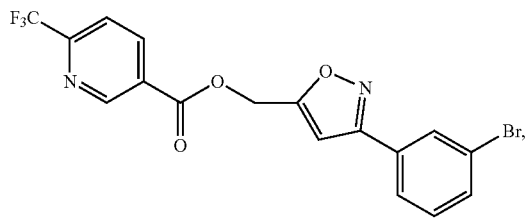
YP-76
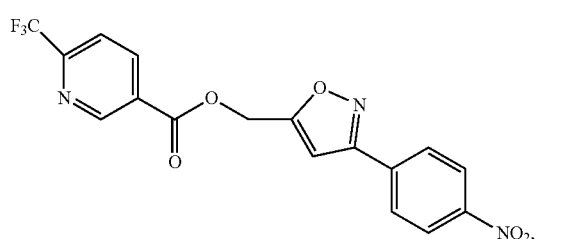
YP-78
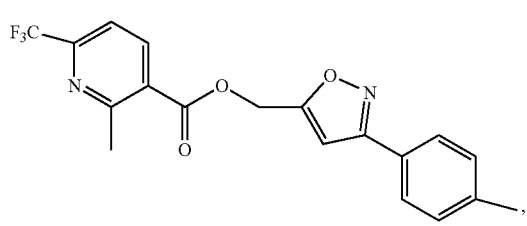
YP-79
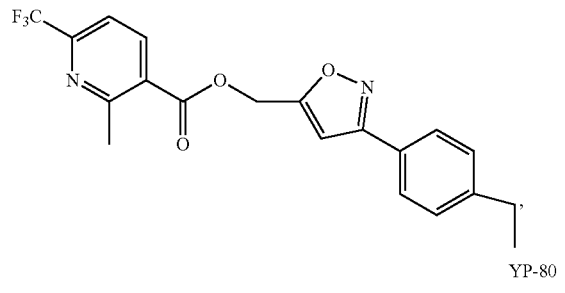
YP-80
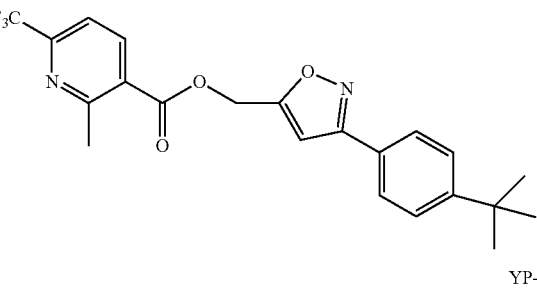
YP-81
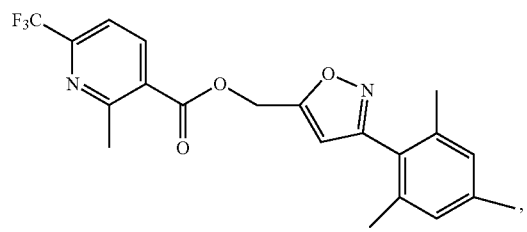

YP-82
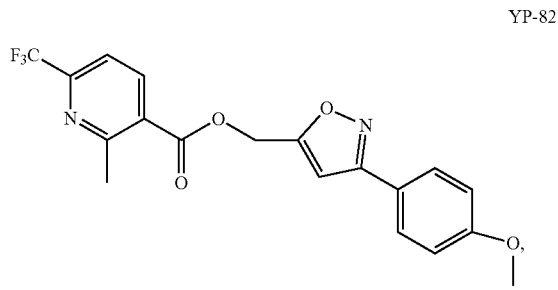
YP-88
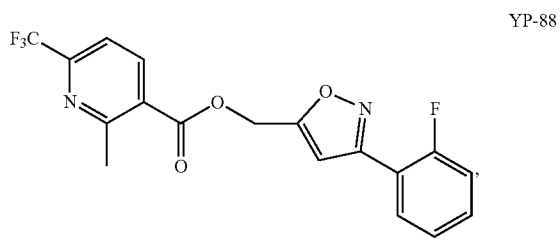
YP-83
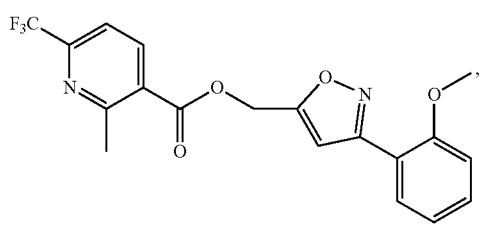
YP-89
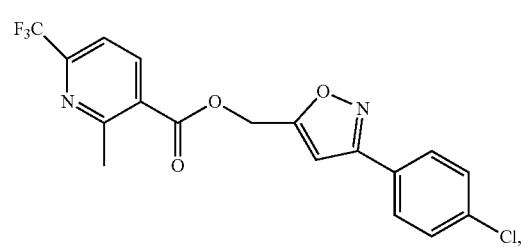
YP-84
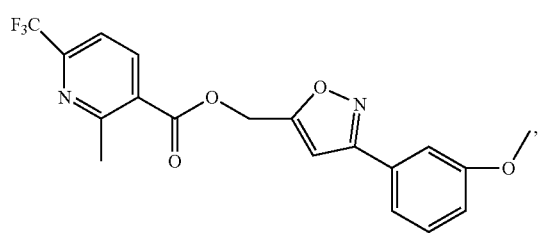
YP-90
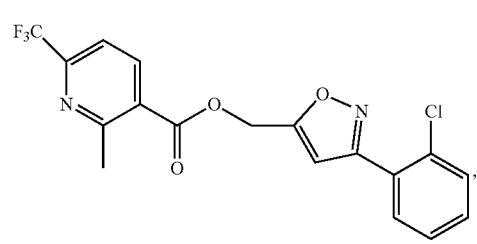
YP-85
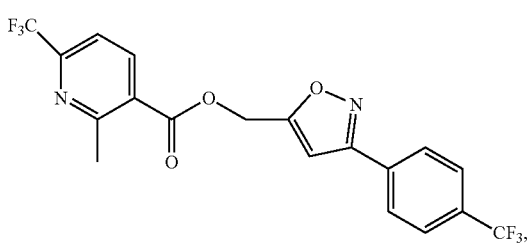
YP-91
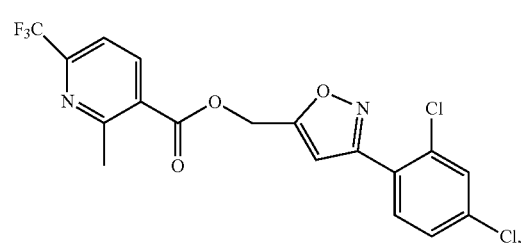
YP-86
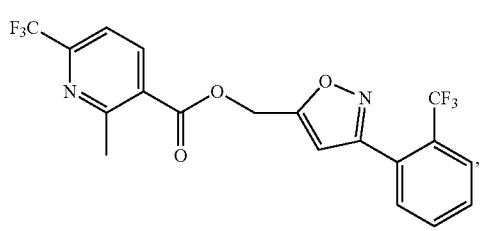
YP-92
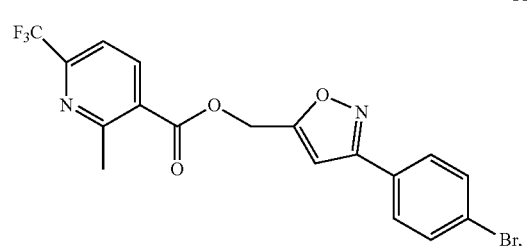
YP-87
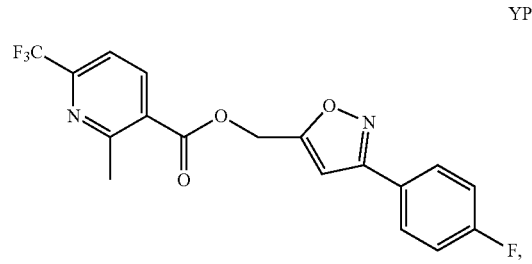
YP-93
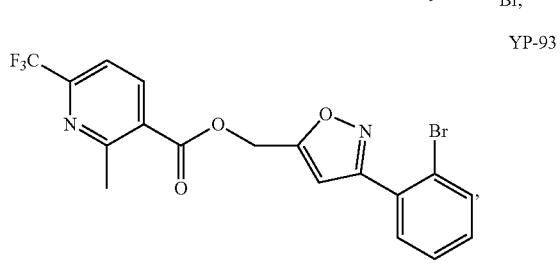

YP-94
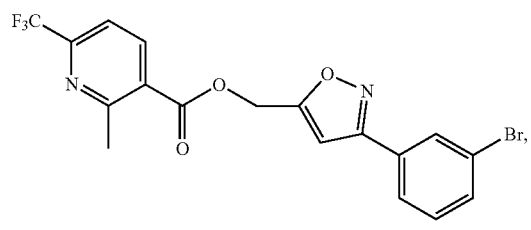
YP-95
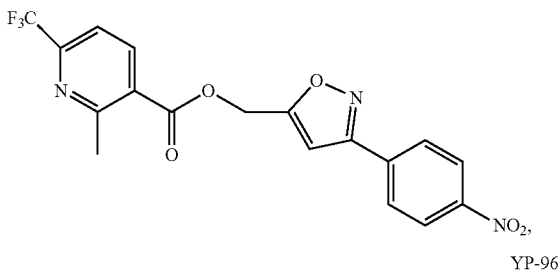
YP-96
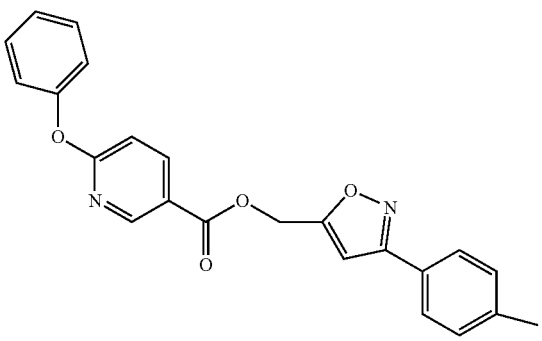
YP-97
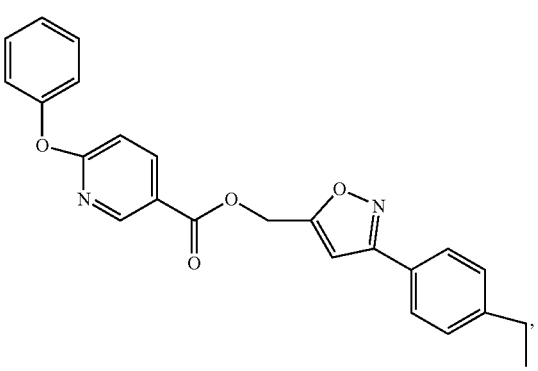
YP-98
YP-99
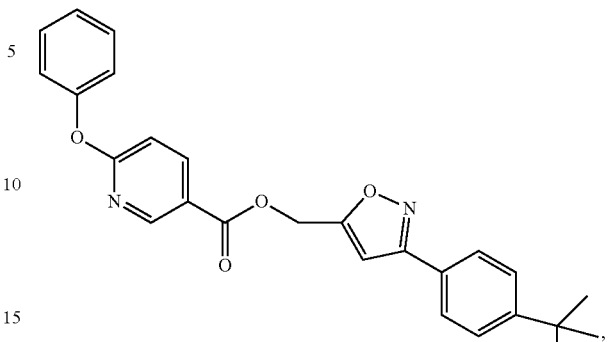
YP-100
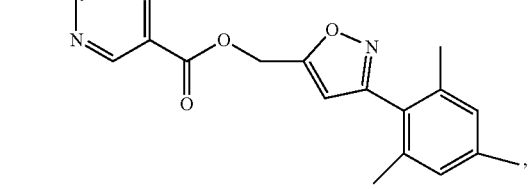
YP-101
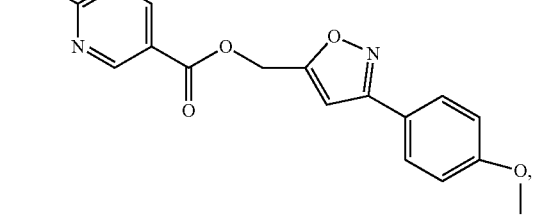
YP-102

YP-103
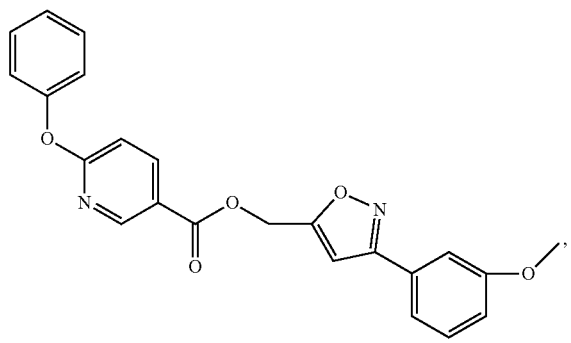
YP-107
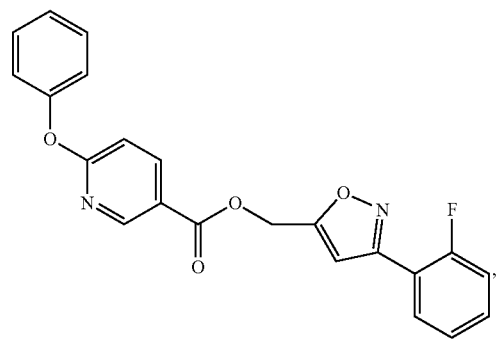
YP-104
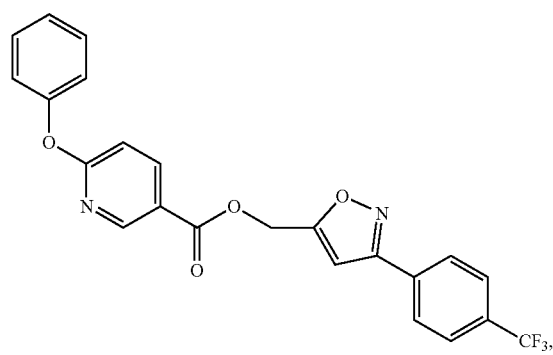
YP-108
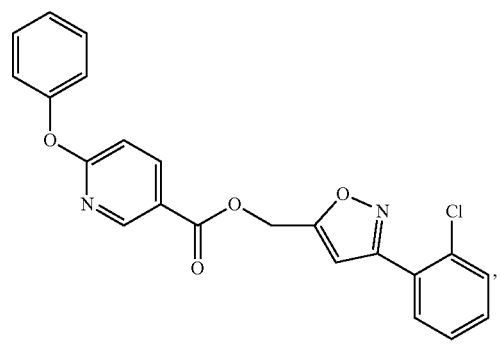
YP-105
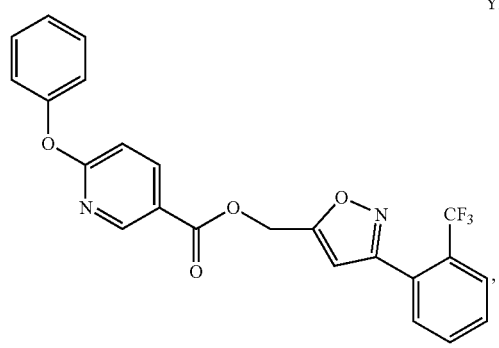
YP-109
YP-106
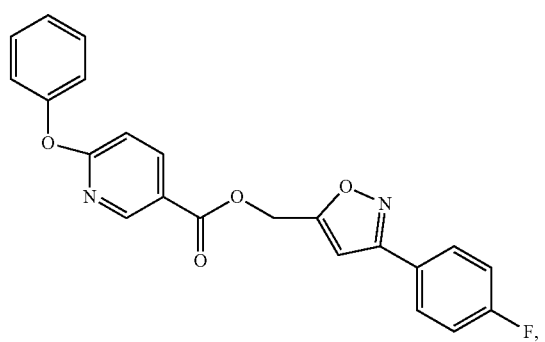
YP-110
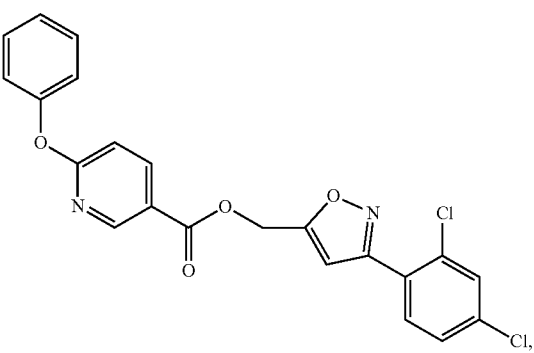

YP-111
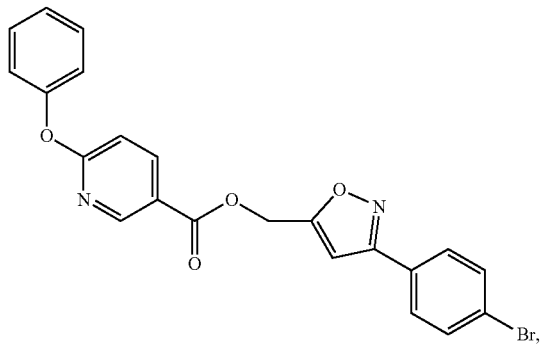
YP-112
YP-113
YP-114
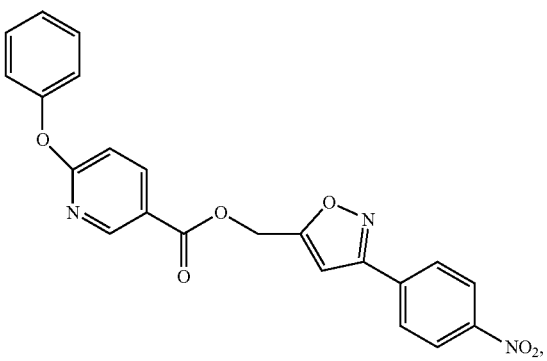
YP-117
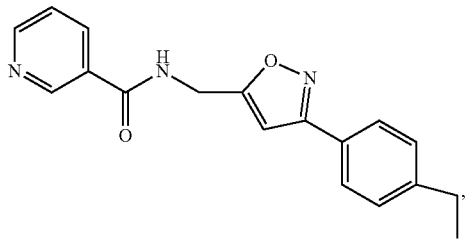
YP-118
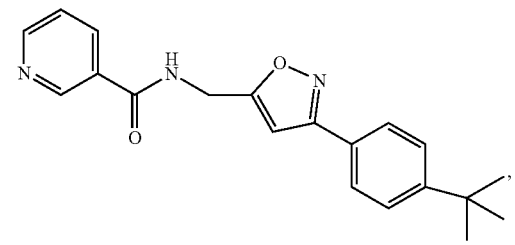
YP-119
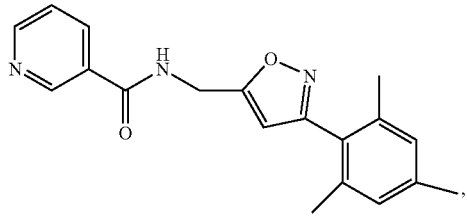
YP-120
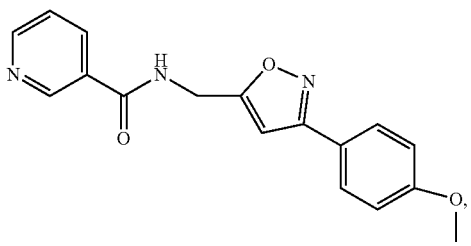
YP-121
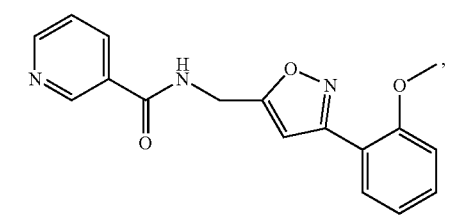
YP-122
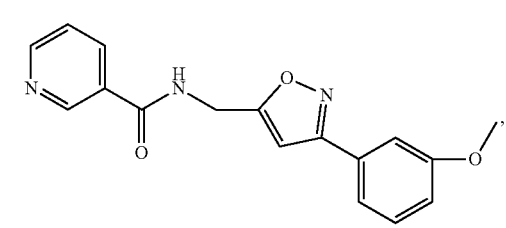

YP-123 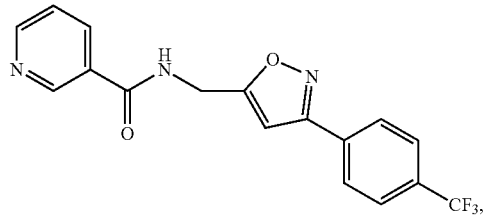
YP-124 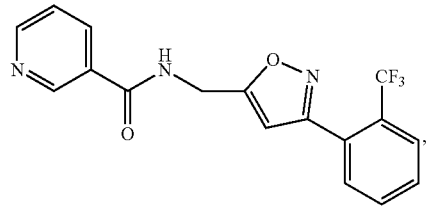
YP-125 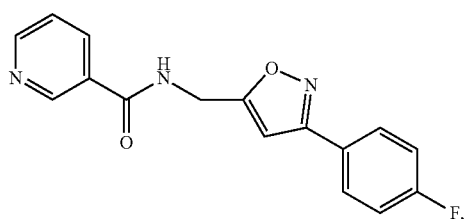
YP-126 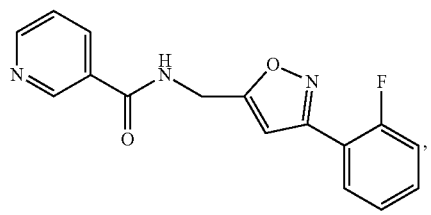
YP-127 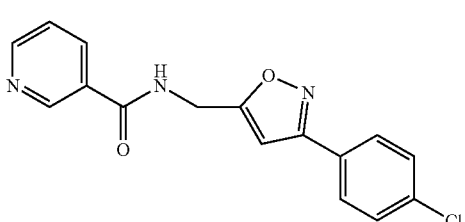
YP-128 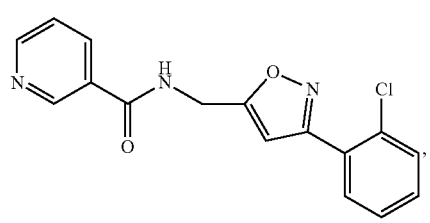
YP-129 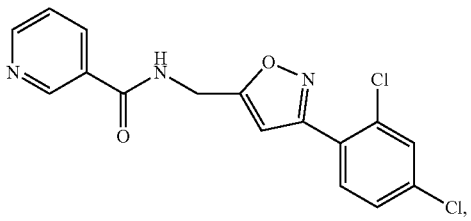
YP-130 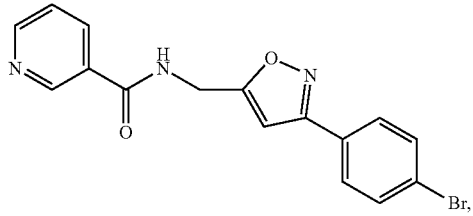
YP-131 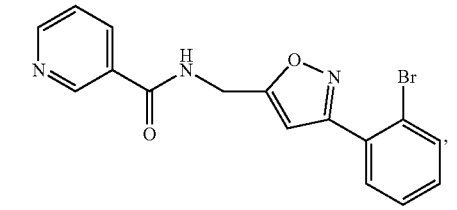
YP-132 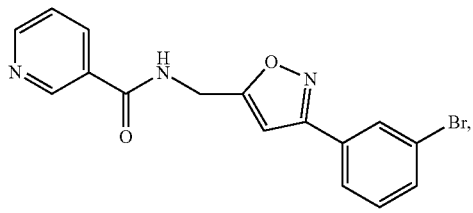
YP-133 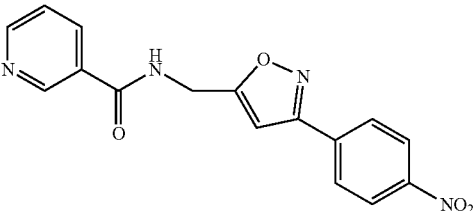
YP-139 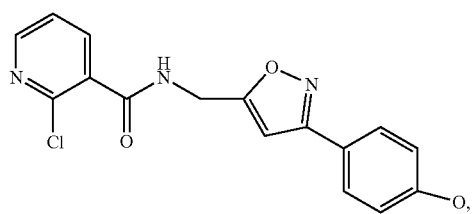
YP-140 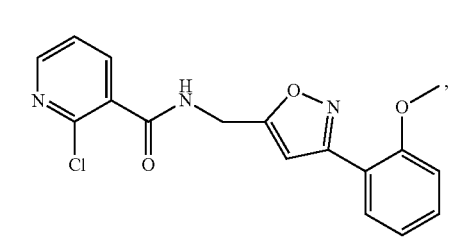
YP-141 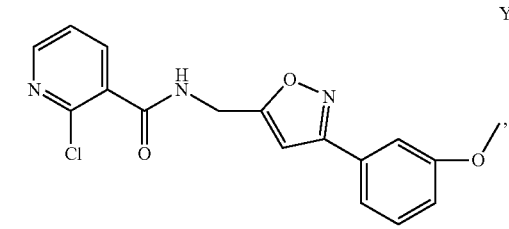

YP-142
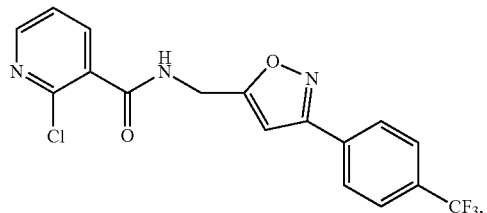
YP-143
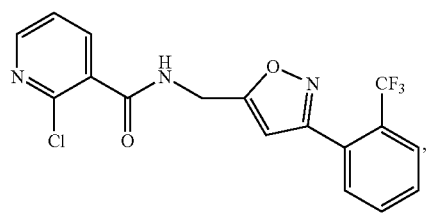
YP-144
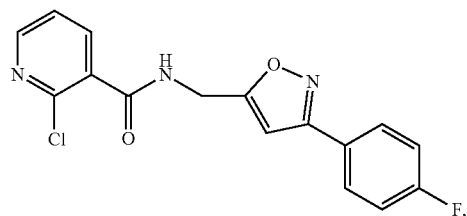
YP-145
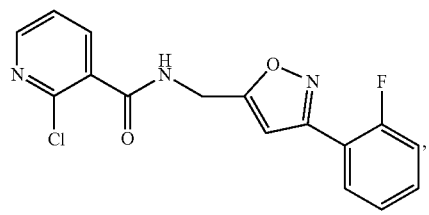
YP-146
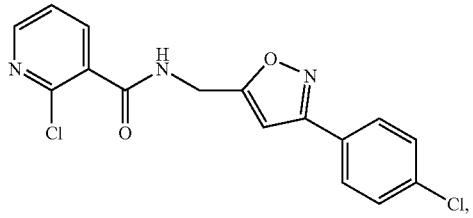
YP-147
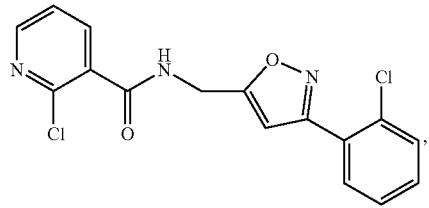
YP-148
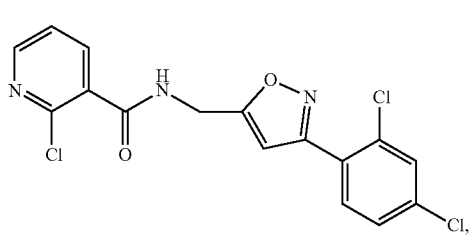
YP-149
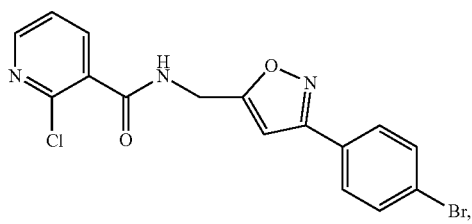
YP-150
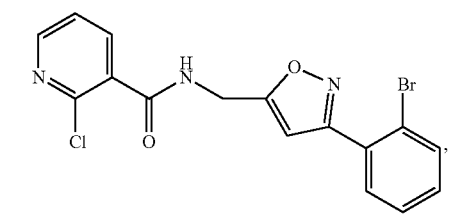
YP-151
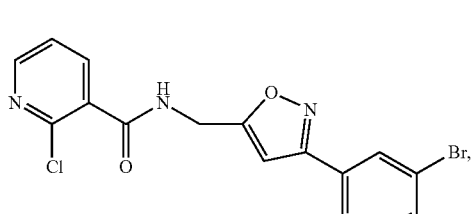
YP-152
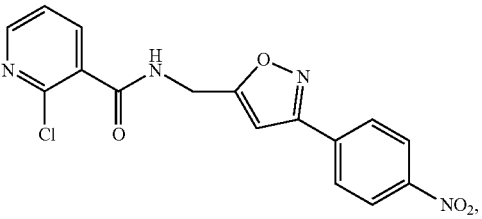
YP-155
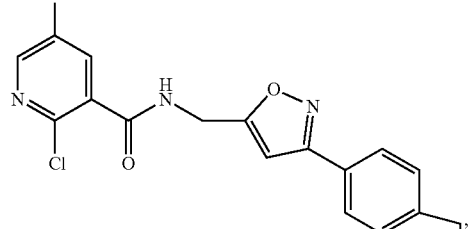
YP-156
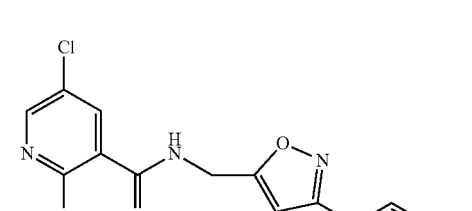

YP-157
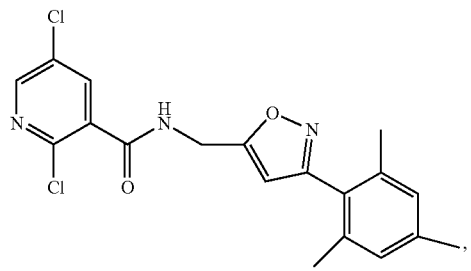
YP-158
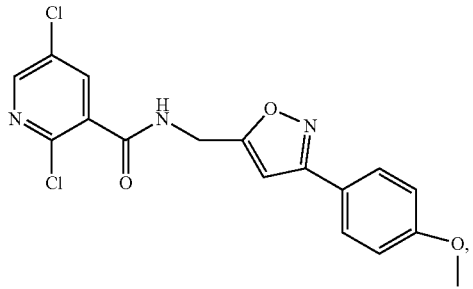
YP-159
YP-160
YP-161
YP-162
YP-163
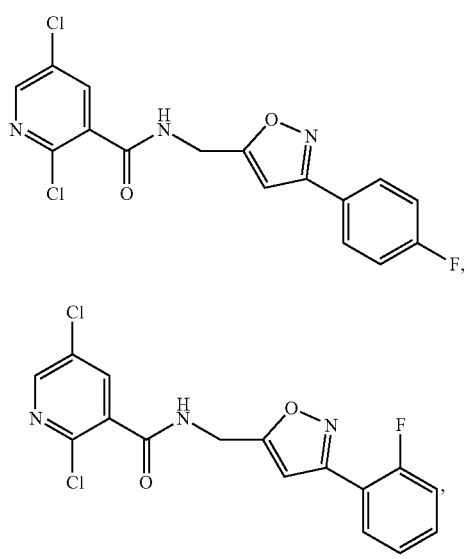
YP-164
YP-165
YP-166
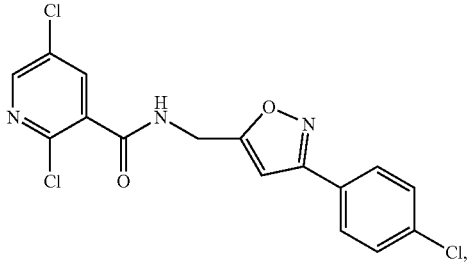
YP-167
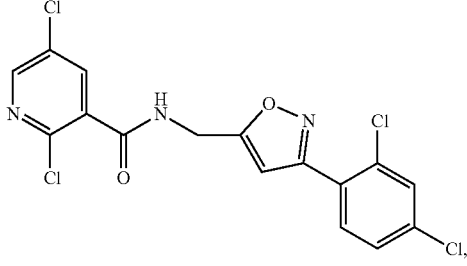
YP-168
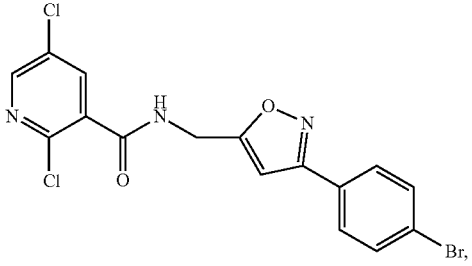

YP-169
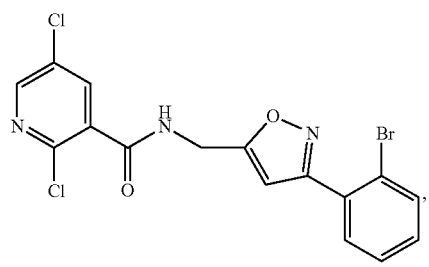
YP-175
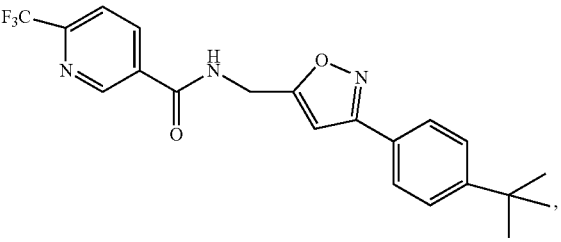
YP-170
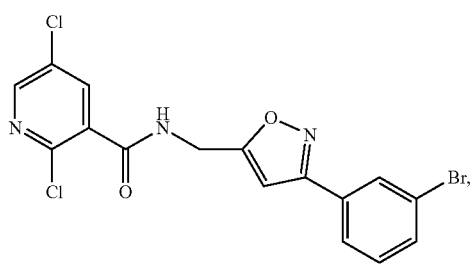
YP-176
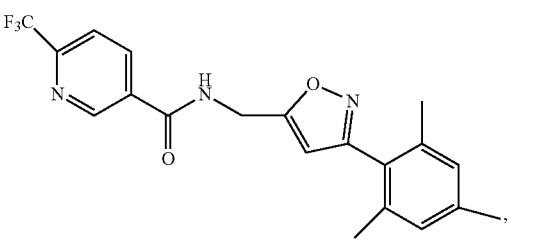
YP-171
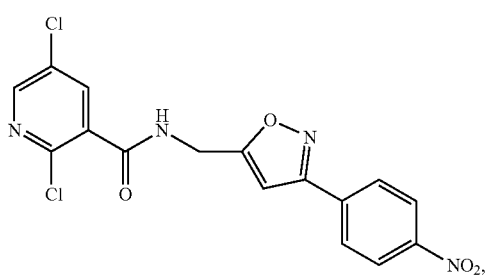
YP-177
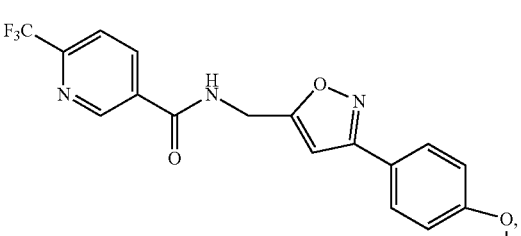
YP-172
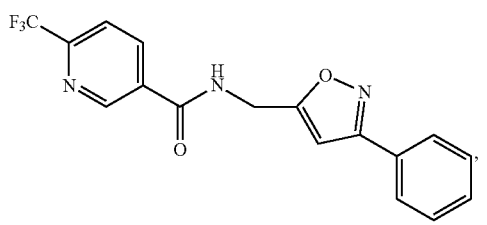
YP-178
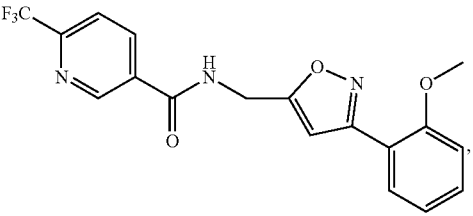
YP-173
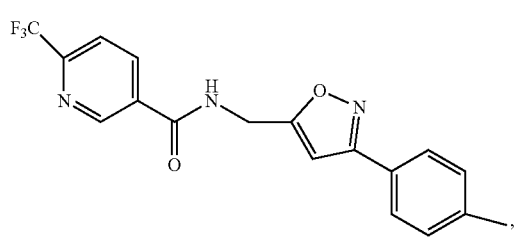
YP-179
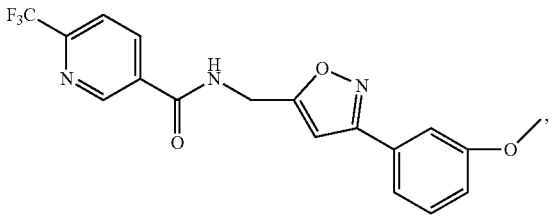
YP-174
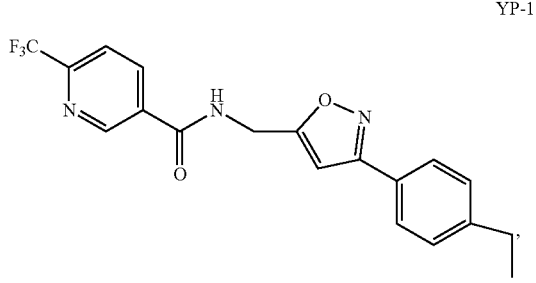
YP-180
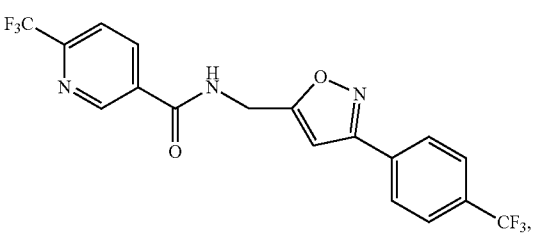

YP-181
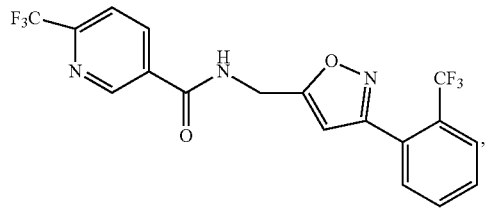
YP-182
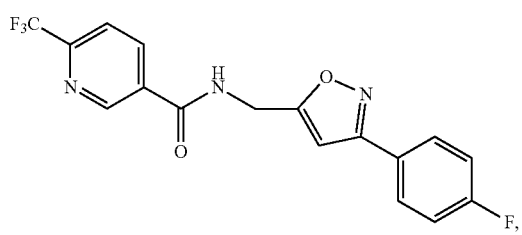
YP-183
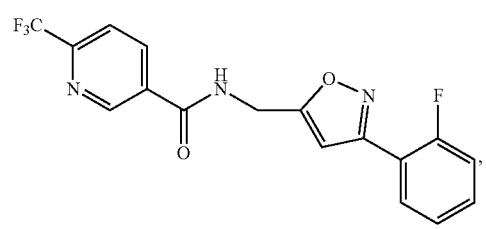
YP-184
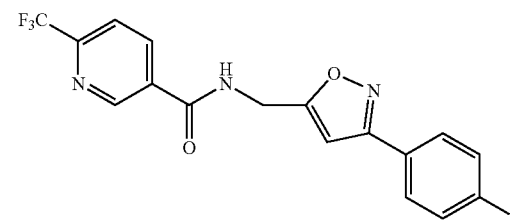
YP-185
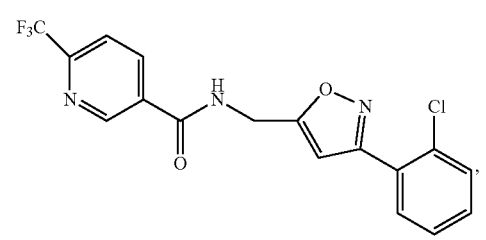
YP-186
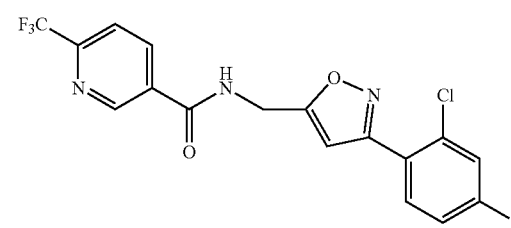
YP-187
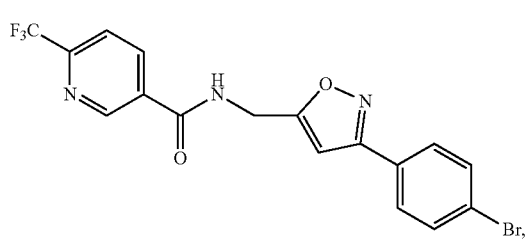
YP-188
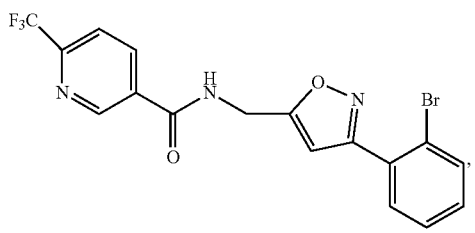
YP-189
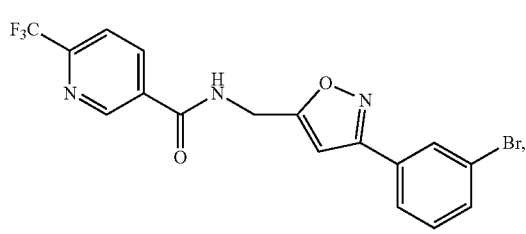
YP-190
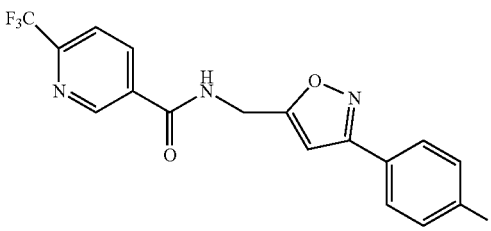
YP-192
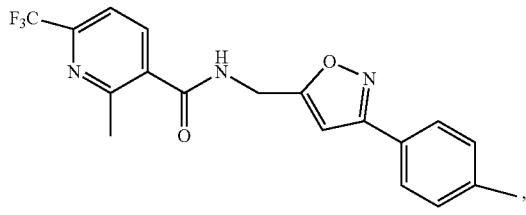
YP-193
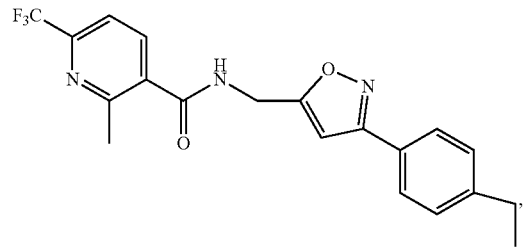

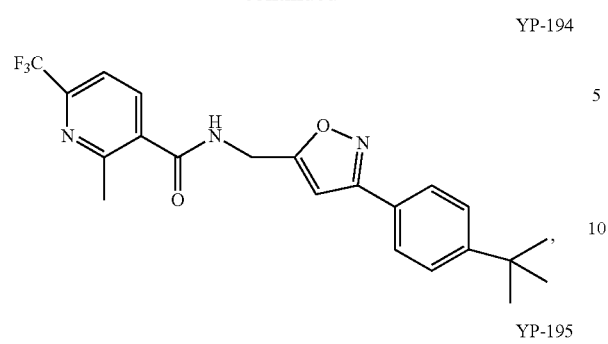

-continued
YP-206
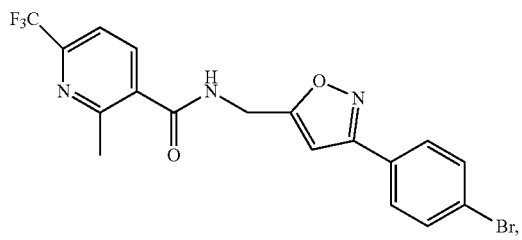
YP-207
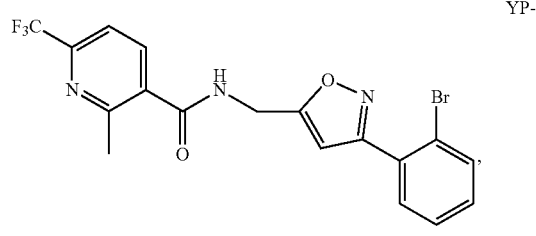
YP-208
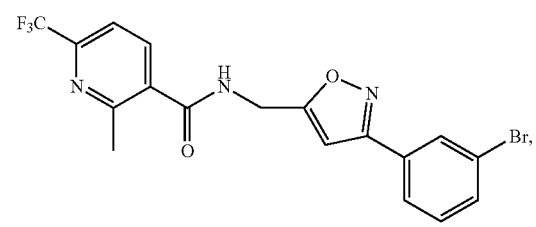
YP-209
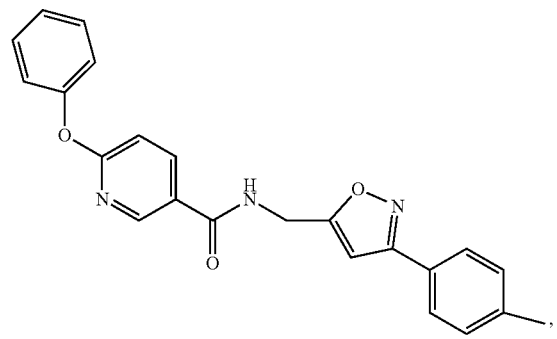
YP-210
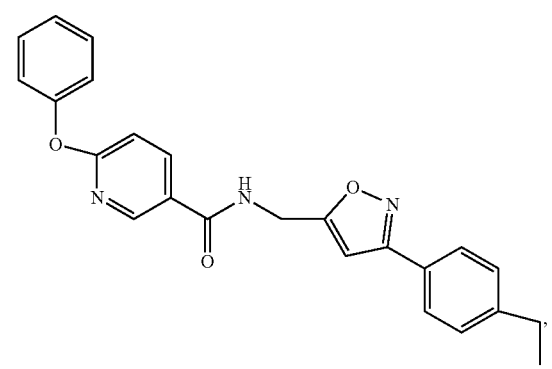
-continued
YP-211
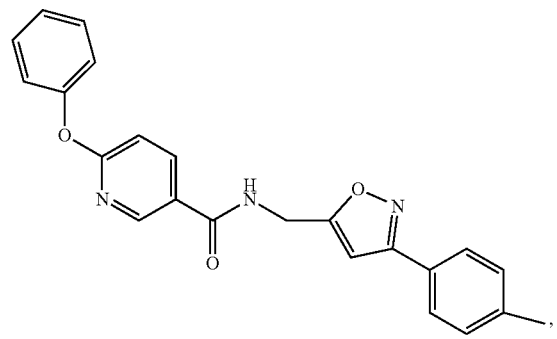
YP-212
YP-213
YP-214
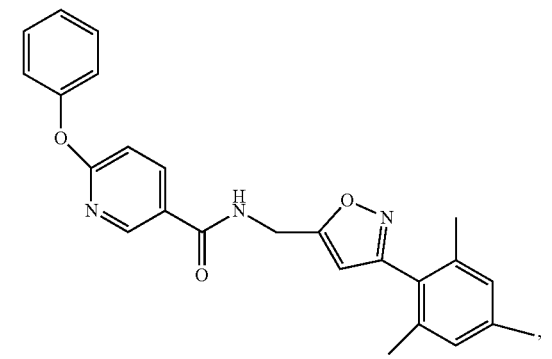

YP-215
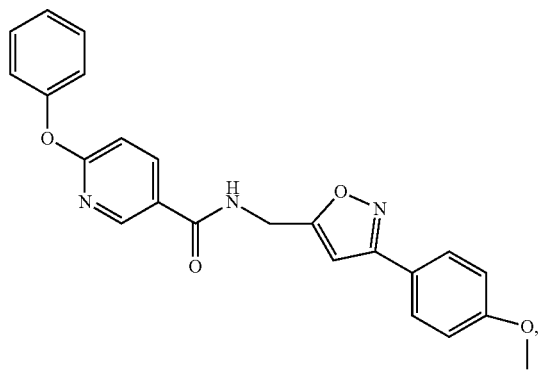
YP-216
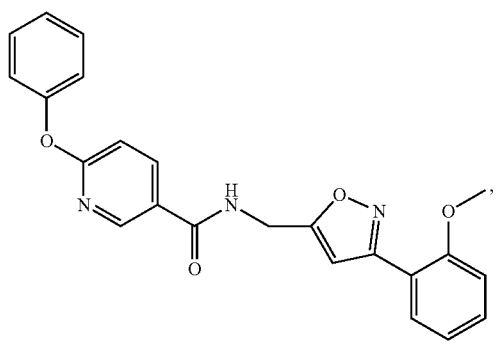
YP-217
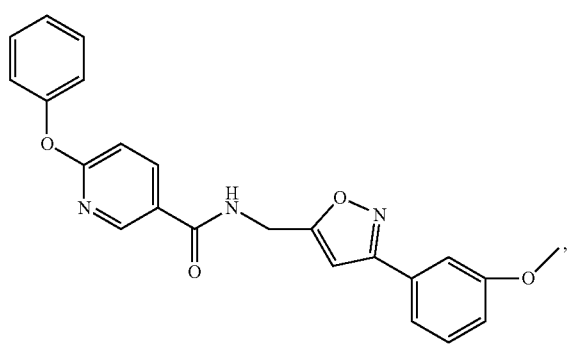
YP-218
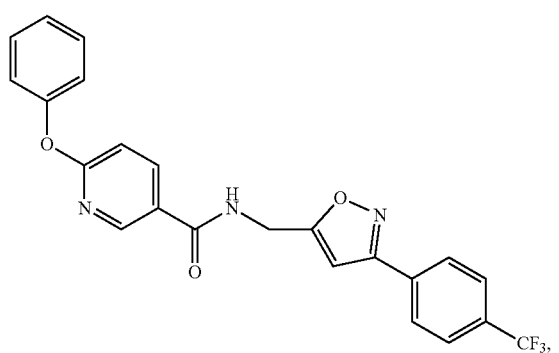
YP-219
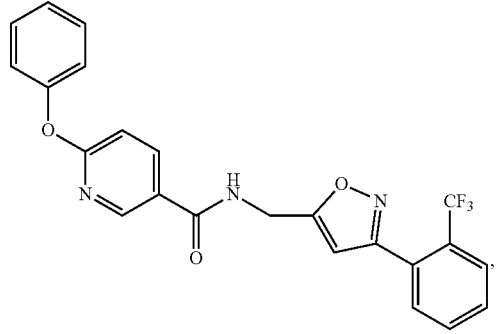
YP-220
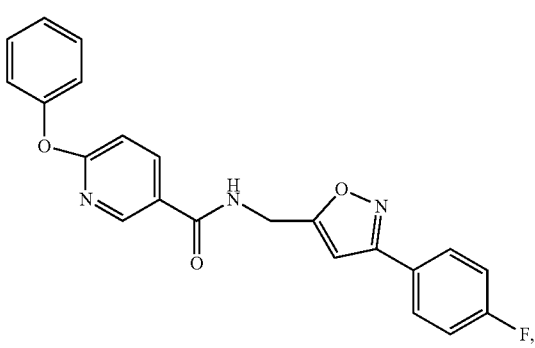
YP-221
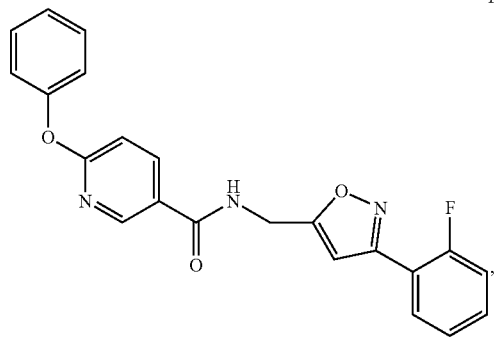
YP-222
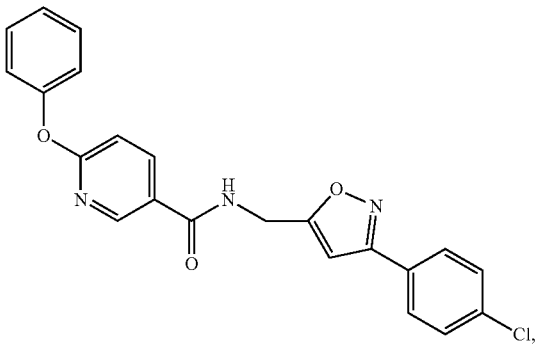

YP-223

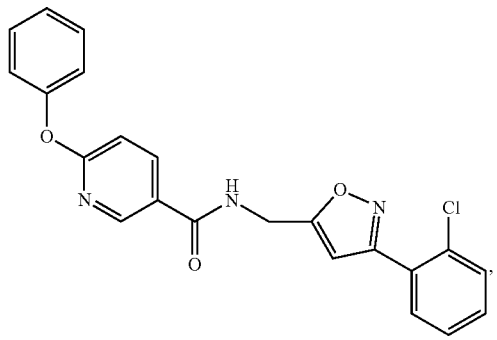

YP-224

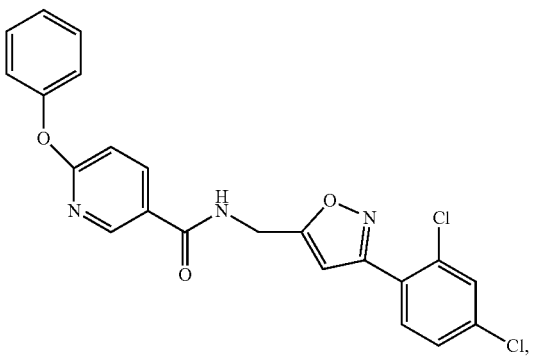

YP-225

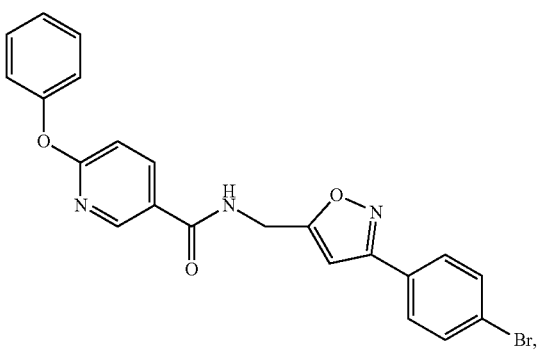

YP-226

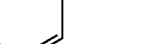

YP-227

YP-228

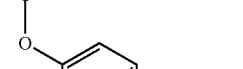

2. A pharmaceutical composition comprising a therapeutically effective amount of one or more of a compound, and/or a pharmaceutically acceptable salt or solvate thereof according to claim 1.

3. The pharmaceutical composition according to claim 2, wherein said pharmaceutical composition further comprises at least one pharmaceutically acceptable adjuvant; the adjuvant is chosen from excipients, carriers, or diluents.

4. The pharmaceutical composition according to claim 2, wherein said pharmaceutical composition is a solid oral preparation, a liquid oral preparation or an injection.

5. The compound according to claim 1 and the pharmaceutically acceptable salt or solvate thereof, wherein the compound having one of the following formulae:

YP-45

-continued
YP-46
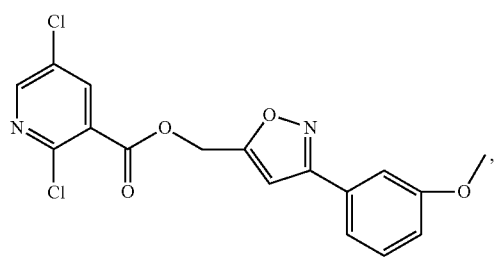
YP-52
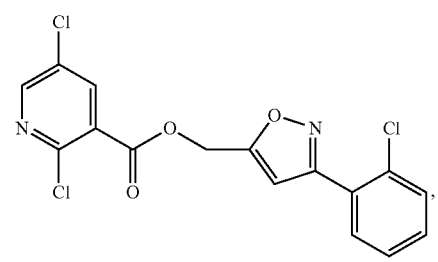
YP-53
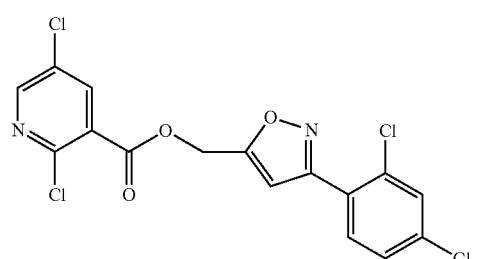
YP-54
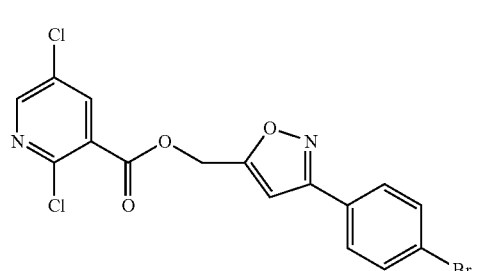
YP-55
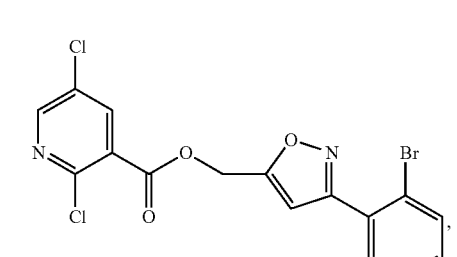
YP-56
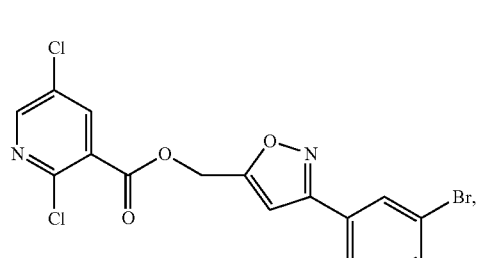
-continued
YP-64
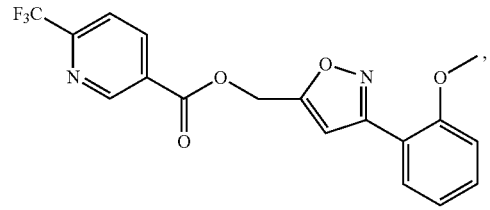
YP-65
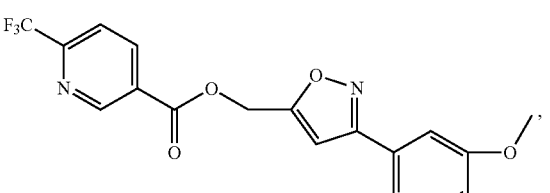
YP-70
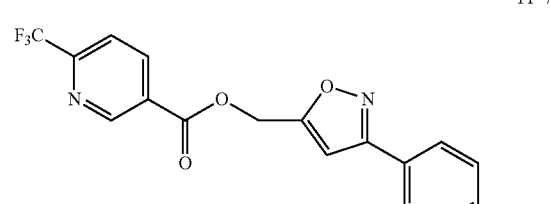
YP-71
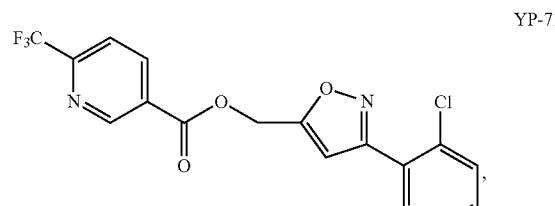
YP-72
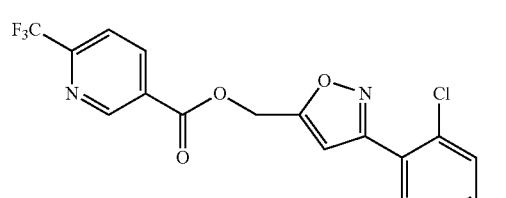
YP-74
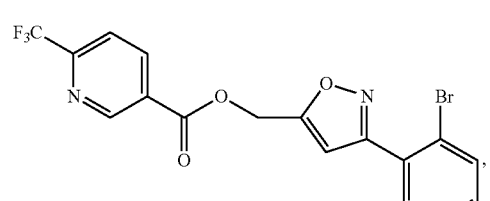
YP-75
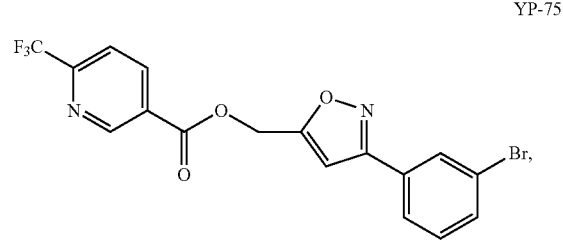

YP-82
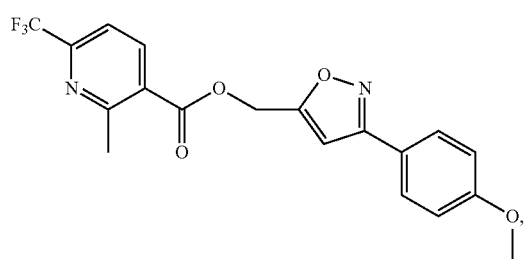
YP-83
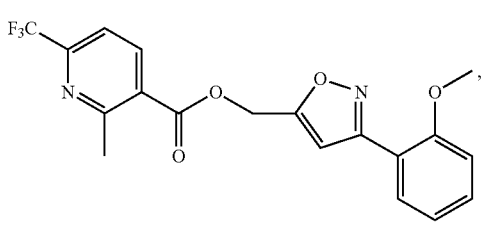
YP-84
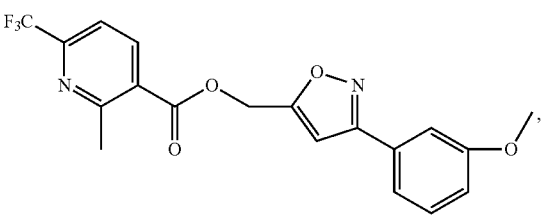
YP-90
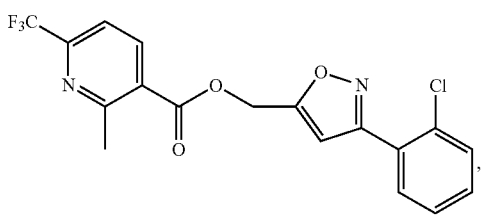
YP-91
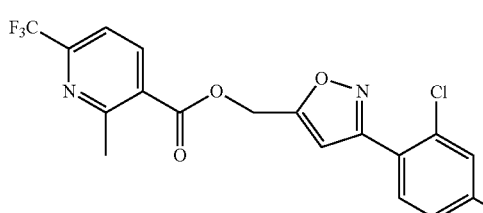
YP-92
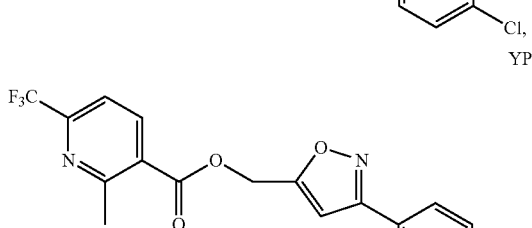
YP-93
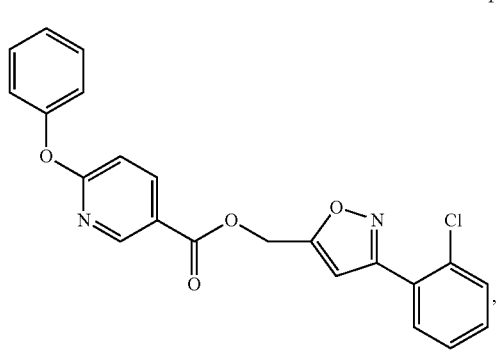
YP-94
YP-109
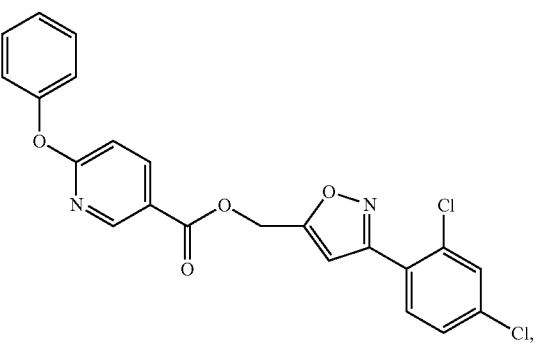
YP-110
YP-111
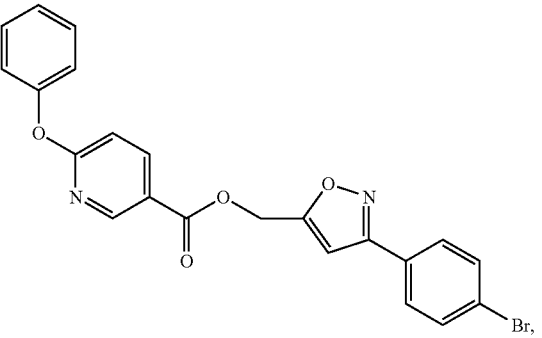

YP-112
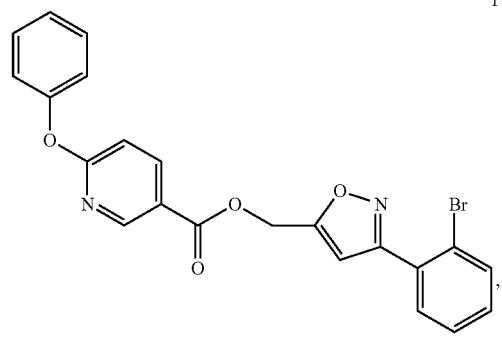
YP-113
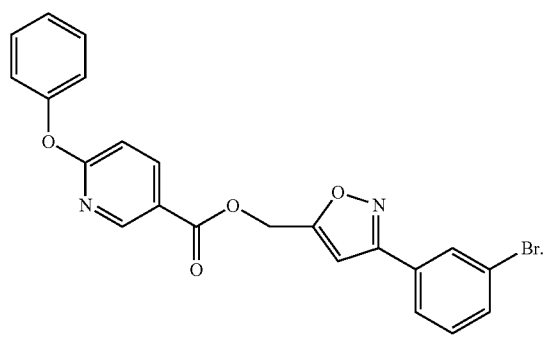
6. The compound according to claim 1 and the pharmaceutically acceptable salt or solvate thereof, wherein the compound having one of the following formulae:
YP-44
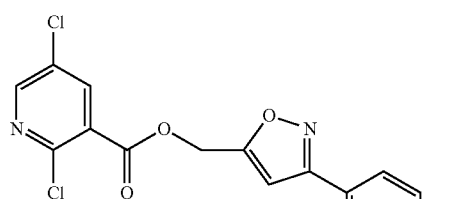
YP-51
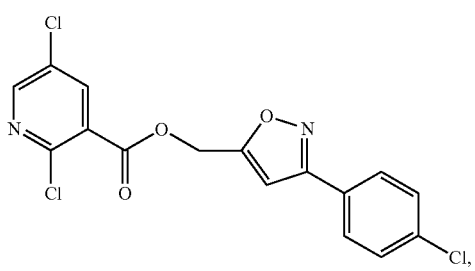
YP-63
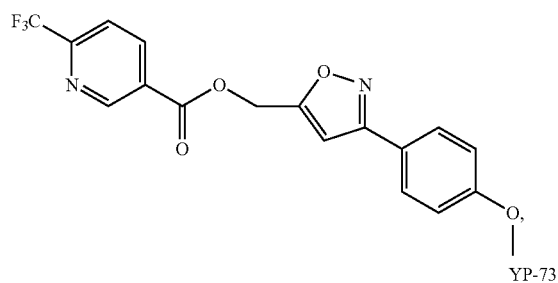
YP-73
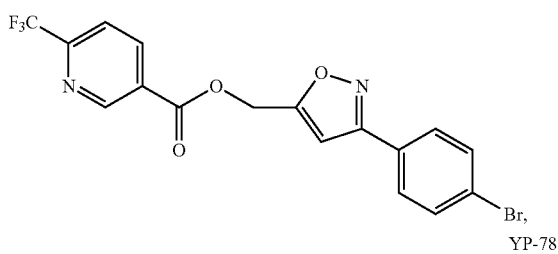
YP-78
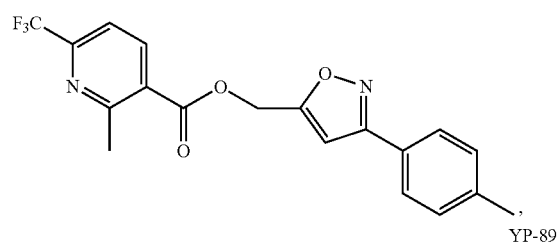
YP-89
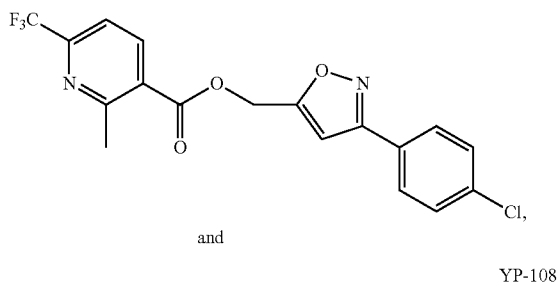
and
YP-108
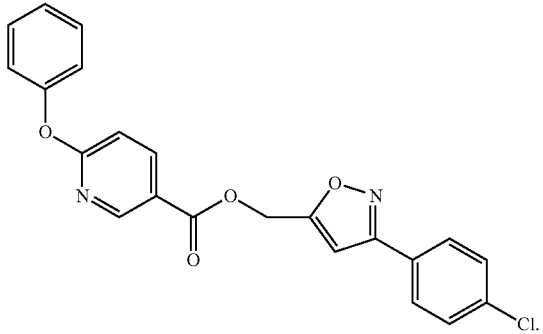
* * * * *